(12) United States Patent
De Morin et al.

(10) Patent No.: US 7,989,461 B2
(45) Date of Patent: *Aug. 2, 2011

(54) SUBSTITUTED QUINAZOLINAMINE COMPOUNDS FOR THE TREATMENT OF CANCER

(75) Inventors: Frenel F. De Morin, Thousand Oaks, CA (US); Jian J. Chen, Newbury Park, CA (US); Stephen Hitchcock, Westlake Village, CA (US); Gang Liu, Oak Park, CA (US); Nick A. Paras, Thousand Oaks, CA (US); Jeffrey Petkus, Reseda, CA (US); Adrian L. Smith, Simi Valley, CA (US); Andrew Tasker, Simi Valley, CA (US); Jiawang Zhu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/643,261

(22) Filed: Dec. 20, 2006

(65) Prior Publication Data

US 2007/0185324 A1   Aug. 9, 2007

Related U.S. Application Data

(60) Provisional application No. 60/753,705, filed on Dec. 23, 2005.

(51) Int. Cl.
*A61K 31/517* (2006.01)
(52) U.S. Cl. ............ 514/266.2; 544/284; 546/148; 546/268.1; 548/136; 548/159; 548/247; 548/361.1; 548/373.1; 548/469
(58) Field of Classification Search .......... 514/266.2; 544/284; 546/148, 268.1; 548/136, 159, 548/247, 361.1, 373.1, 469
See application file for complete search history.

(56) References Cited

U.S. PATENT DOCUMENTS 7,335,658 B2 * 2/2008 Chakka et al. .......... 514/252.02

FOREIGN PATENT DOCUMENTS

| WO | WO 98/35958 | * | 2/1998 |
| WO | 9835958 A1 | | 8/1998 |
| WO | 9932106 A1 | | 7/1999 |
| WO | 2005037285 A1 | | 4/2005 |
| WO | 2005049577 A1 | | 6/2005 |
| WO | 2006039718 A2 | | 4/2006 |
| WO | WO 2006/039718 | * | 4/2006 |
| WO | 2007076092 A2 | | 7/2007 |

* cited by examiner

*Primary Examiner* — James O. Wilson
*Assistant Examiner* — Douglas M Willis
(74) *Attorney, Agent, or Firm* — G. Prabhakar Reddy

(57) ABSTRACT

The present invention comprises a new class of compounds capable of modulating Raf kinase and, accordingly, useful for treatment of Raf kinase mediated diseases, including melanomas, tumors and other cancer-related conditions. The compounds have a general Formula I

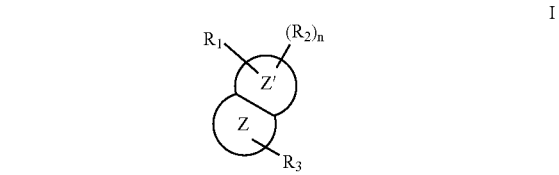

wherein $R^1$ is

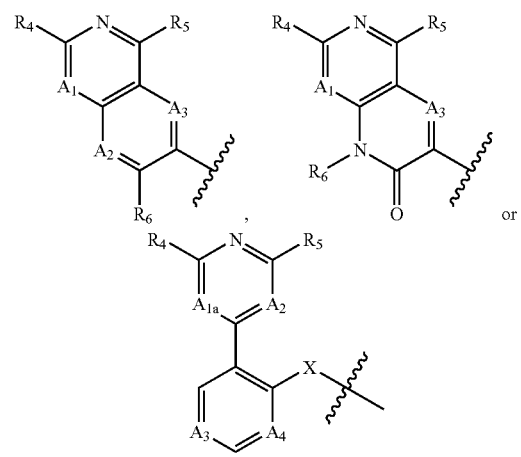

and $A^1$, $A^2$, $A^3$, $A^4$, X, Z, Z', $R^1$, $R^2$, $R^3$, $R^4$, $R^5$ and $R^6$ are defined herein. The invention further comprises pharmaceutical compositions, methods for treatment of Raf kinase mediated diseases, and intermediates and processes useful for the preparation of compounds of the invention.

14 Claims, No Drawings

SUBSTITUTED QUINAZOLINAMINE COMPOUNDS FOR THE TREATMENT OF CANCER

RELATED APPLICATIONS

This application claims the benefit of U.S. Provisional Application No. 60/753,705, filed Dec. 23, 2005, which is hereby incorporated herein by reference in its entirety.

FIELD OF THE INVENTION

The invention generally relates to the field of pharmaceutical agents and, specifically to compounds, intermediates and pharmaceutical compositions useful for treating raf protein kinase-mediated diseases, and methods for treating raf-mediated diseases.

BACKGROUND OF THE INVENTION

Cancer is one of the most widespread diseases of mankind and a major cause of death worldwide. In an effort to find an effective treatment or a cure for one or more of the many different types of cancers and cancer disease, over the last couple of decades, numerous groups have invested a tremendous amount of time, effort and financial resources. However, to date, of the available cancer treatments and therapies, only a few offer any considerable degree of success.

Cancer is caused in many cases by the effects of oncoproteins. These are proteins having different structures as compared to their counterpart proteins in normal, healthy organisms. These oncoproteins are capable of transforming a normal cell into an uncontrollable, proliferating cell i.e., a cancerous cell, leading to the formation and growth of cancerous tumors. Oncoproteins are formed and expressed in an organism as a product of onco-genes, whose nucleotides sequence encodes the oncoprotein. Oncogenes occur as a result of a mutation of a "normal", healthy gene, typically referred to as the "proto-oncogene." Such mutations in proto-oncogenes produce protein products, which alter the normal programs of cell proliferation, differentiation and death. In a human cancer cell, one cell-signaling pathway in in which a proto-oncogene is mutated is the RAS-RAF-MEK-ER MAP kinase-signaling pathway. This pathway has been found to mediate cellular responses to growth signals. (Peyssonnaux et al., Biol. Cell, 93:53-62 (2001)).

The cell-signaling pathway involves the binding of a RAS substrate to activate a Raf kinase enzyme, which in turn activates the MEK kinase and so forth. There are three cytoplasmic serine/threonine RAF kinase proteins, which are polypeptides encoded by the nucleotide sequence of three Raf genes. The three Raf proteins found in mammals are A-Raf, B-Raf and C-Raf (C-raf is also known as Raf-1). (Biol. Cell, 93:53-62 (2001)). One feature in common among the three proteins is that they all share highly conserved regions, called CR1, CR2 and CR3. The CR1 domain is rich in cysteine residues, while the CR2 region contains many serines and threonine residues. The CR3 domain contains the kinase activity. The three naturally occurring Raf proteins also feature size differences. On average, B-raf proteins are larger than the other two, having a molecular weight of about 90 kDa, while the A-raf and C-raf have an average molecular weight of about 70 kDa. All three RAF proteins function by phosphorylating MEK-1/2, which in turn phosphorylates Erk-1/2, thereby activating the MEK-ERK MAP kinase portion of the signaling pathway described above. Structure, activity and function of the members of the Raf kinase family are further described in detail in Morrison and Cutler, Current Opinion in Cell Biology, 9:174-179 (1997) and U.S. Pat. Nos. 5,618,670, 5,156,841, and 6,566,581.

The B-raf protein has been found to be much more capable, than the A-raf and C-raf proteins, of phosphorylating the MEK-I and MEK-2 proteins. More specifically, the B-raf phosphorylating activity is about 500× stronger than that of A-raf and about 10× stronger than that of C-raf. (Mol. Cell Biol., 15 (1997)). Accordingly, B-raf has become a potential target for regulating the RAS-RAF-MEK-ERK-MAP signaling pathway and, in turn, regulating programmed cell proliferation, cell differentiation and cell death.

B-raf kinase is commonly activated by somatic point mutations in cancerous cells. For example, B-raf somatic missense mutations occur in about 66% of malignant melanomas and at lower frequency in a wide range of human cancers. B-raf mutations have been found in 28 primary cancers/STC's, including 6 of 9 primary melanomas, 12 of 15 melanoma STC's, 4 of 33 colorectal carcinomas, 5 or 35 ovarian neoplasms, and 1 of 182 sarcomas. Although B-raf mutations occur in a wide range of cancers, there is a trend towards the occurance of mutations in cancer types in which a substantial portion of cases are known to harbor RAS mutations (for example, malignant melanomas, colorectal cancer, and borderline ovarian cancers). Mutated B-raf proteins have elevated kinase activity and are transforming in NIH3T3 cells. All mutations of B-raf have been found to be within the kinase domain, with a single substitution (V600E) accounting for about 80% of the mutated B-raf proteins discovered to date. It is worth noting that Ras function is not required for the growth of cancer cell lines with the V599E mutation. The high frequency of B-raf mutations in melanomas and the relative lack of effective therapies for advanced stages of this disease suggest that inhibition of wild-type B-raf and/or mutated B-raf activity may provide new therapeutic opportunities for metastatic and/or malignant melanomas.

Various groups have proposed different classes of compounds to generally modulate, or specifically inhibit, Raf kinase activity, for use to treat Raf-mediated disorders. For example, the PCT publication, WO 99/32106, describes substituted heterocyclic ureas for the inhibition of Raf kinase, WO 03/047523, describes methods for treating cancers resulting from the up-regulation of the RAF-MEK-ERK pathway using Gleevec® and "Gleevec®-like" compounds, WO 00/42012, describes delta-carboxyaryl substituted diphenyl ureas as Raf kinase inhibitors, WO 01/38324, describes substituted heteroaryl compounds for the inhibition of B-Raf kinase, U.S. Publication No. 2001/006975, describes methods of treating tumors mediated by raf kinase using substituted urea compounds, and U.S. Pat. No. 6,187,799, describes methods of treating tumors mediated by raf kinase using aryl urea compounds.

BRIEF SUMMARY OF THE INVENTION

The present invention provides a new class of nitrogen-containing bicyclic heteroaryl compounds useful for modulating Raf kinase proteins and, thereby, useful for treating Raf kinase-mediated diseases and conditions. Particularly, the compounds are useful for treating tumors, melanomas and other forms of cancer. The compounds provided by the invention, including stereoisomers, tautomers, solvates, pharmaceutically acceptable salts, derivatives or prodrugs thereof, are defined by general Formula I

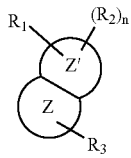

wherein Z, Z', $R^1$, $R^2$, $R^3$ and n are as described below.

In another embodiment, the invention provides compounds defined generally by Formula II

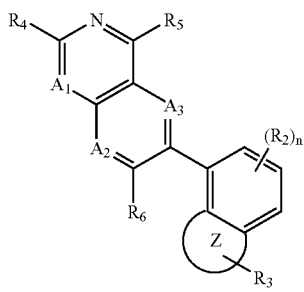

wherein $A^1$, $A^2$, $A^3$, $R^1$, $R^2$, $R^3$, $R^4$, $R^5$, $R^6$, Z and n are as described below.

In another embodiment, the invention provides compounds defined generally by Formula III

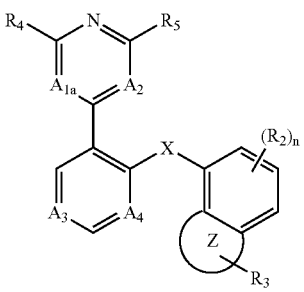

Wherein each of $A^{1a}$, $A^2$, $A^3$, $A^4$, $R^2$, $R^4$, $R^5$, X, Z and n are described below.

The invention also provides procedures for making compounds of Formulas I-III, as well as intermediates useful in such procedures.

The compounds provided by the invention are capable of modulating Raf kinase activity, and more particularly of modulating B-raf kinase activity. To this end, the invention further provides for the use of these compounds for therapeutic, prophylactic, acute and/or chronic treatment of raf kinase-mediated diseases, such as those described herein. For example, the invention provides the use and preparation of a medicament, containing one or more of the compounds, useful to attenuate, alleviate, or treat disorders through inhibition of B-raf. These compounds are also useful in the treatment of a cancerous disease or condition. Accordingly, these compounds are useful in the manufacture of anti-cancer medicaments. In one embodiment, the invention provides a pharmaceutical composition comprising an effective dosage amount of a compound of any of Formulas I-III in association with a least one pharmaceutically acceptable carrier, adjuvant or diluent.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, nitrogen-containing bicyclic heteroaryl compounds useful for treating cell proliferation-related disorders, including cancer, are provided. The compounds, including stereoisomers, tautomers, solvates, pharmaceutically acceptable salts, derivatives or prodrugs thereof, are defined by general Formula I:

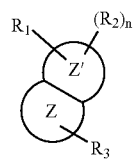

wherein
Z is

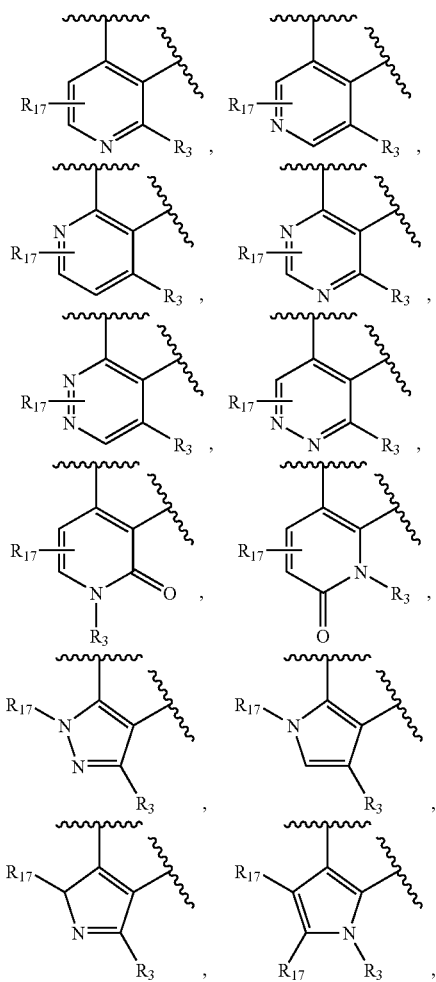

-continued

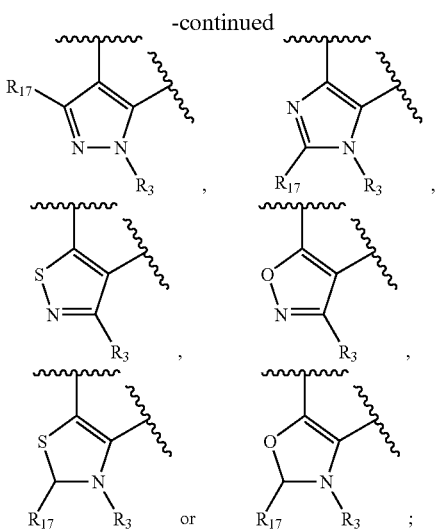

Z' is a 5- or 6-membered aromatic ring of carbon atoms optionally comprising 1-3 heteroatoms selected from N, O and S, such that Z' and Z taken together form a fused 8-, 9- or 10-membered heteroaryl or heterocyclic ring;

$R^1$ is

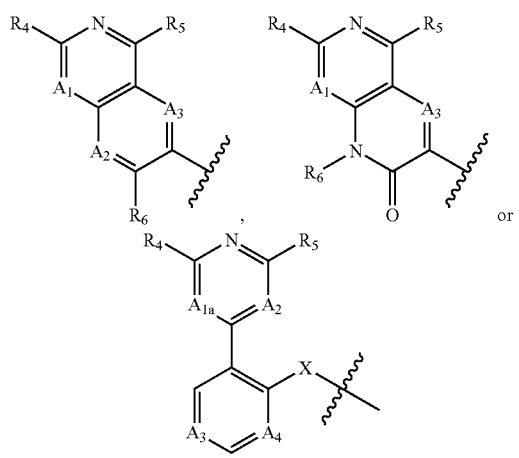

wherein
each of $A^1, A^{1a}, A^2, A^3$ and $A^4$ is, independently, $CR^6$ or N;
X is $CR^6R^6$, C(O), $NR^6$, O or $S(O)_p$ wherein p is 0, 1, or 2;
$R^4$ is halo, haloalkyl, $NO_2$, CN, $R^7$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;
alternatively, $R^4$ taken together with $R^6$, when $A^{1a}$ is $CR^6$, form a 5- or 6-membered ring of carbon atoms optionally comprising 1-3 heteroatoms selected from N, O and S, and optionally substituted with 1-3 substituents of $NR^7R^7$, $NR^7R^8$, $OR^7$, $SR^7$, $OR^8$, $SR^8$, $C(O)R^7$, $C(O)R^8$, $C(O)NR^7R^7$, $NR^7C(O)R^7$, $NR^7C(O)NR^7R^7$, $NR^7(COOR^7)$, $C(O)NR^7R^8$, $NR^7C(O)R^8$, $NR^7C(O)NR^7R^8$, $NR^7(COOR^8)$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2R^8$ or $R^9$;

$R^5$ is H, halo, haloalkyl, $NO_2$, CN, $OR^7$, $SR^7$, $NR^7R^7$, $NR^7R^8$, $C(O)R^7$, $COOR^7$, $C(O)NR^7R^7$, $C(O)NR^7R^8$, $NR^7C(O)NR^7R^7$, $NR^7C(O)NR^7R^8$, $OC(O)NR^7R^8$, $S(O)_2R^7$, $S(O)_2NR^7R^7$, $S(O)_2NR^7R^8$, $NR^7S(O)_2R^7$, $NR^7S(O)_2R^8$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

each $R^6$ is, independently, H, halo, haloalkyl, $NO_2$, CN, $NR^7R^7$, $NR^7R^8$, $OR^7$, $SR^7$, $C(O)R^7$, $OC(O)R^7$, $COOR^7$, $C(O)NR^7R^7$, $C(O)NR^7R^8$, $NR^7C(O)R^7$, $NR^7C(O)R^8$, $NR^8C(O)NR^7R^8$, $NR^7(COOR^7)$, $OC(O)NR^7R^8$, $S(O)_2R^7$, $S(O)_2NR^7R^8$, $NR^7S(O)_2NR^7R^8$, $NR^7S(O)_2R^7$, $NR^7S(O)_2R^7$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^2$ is halo, haloalkyl, $NO_2$, CN, $NR^7R^7$, $NR^7R^8$, $OR^7$, $SR^7$, $C(O)R^7$, $OC(O)R^7$, $COOR^7$, $C(O)NR^7R^7$, $C(O)NR^7R^8$, $NR^7C(O)R^7$, $NR^7C(O)R^8$, $NR^8C(O)NR^7R^8$, $NR^7(COOR^7)$, $OC(O)NR^7R^8$, $S(O)_2R^7$, $S(O)_2NR^7R^8$, $NR^7S(O)_2NR^7R^8$, $NR^7S(O)_2R^7$, $NR^7S(O)_2R^7$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^3$ is $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$R^{17}$ is H, halo, haloalkyl, CN, OH, $NO_2$, $NH_2$, acetyl, methyl, methoxyl, ethyl, ethoxyl, propyl, propoxyl, isopropyl, cyclopropyl, butyl, isobutyl, sec-butyl, tert-butyl, methylamine, dimethylamine, ethylamine, diethylamine, propylamine, isopropylamine, dipropylamine, diisopropylamine, butylamine, benzyl or phenyl; and n is 0, 1, 2 or 3, provided that (1) when Z and Z' taken together form a fused ring of

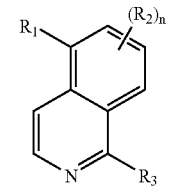

wherein n is 0 and $R^3$ is $NHR^{11}$, then (a) $R^1$ is not phenyl, naphthyl or a mono- or bicyclic heteroaryl comprising 1, 2 or 3 nitrogen atoms and optionally substituted with $C_{1-6}$-alkyl, $C_{1-6}$-alkoxyl or $C_{1-6}$-haloalkyl, and (b) $R^{11}$ is not a benzimidazole, benzothiazole, isoquinoline, quinoline or an optionally substituted phenyl ring.

In another embodiment, there are provided compounds of having a Formula Ia:

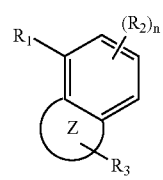

Ia wherein $R^1$ is

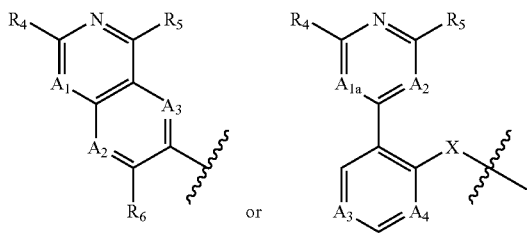

or

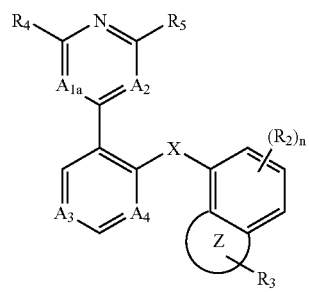

and each of $A^1$, $A^{1a}$, $A^2$, $A^3$, $A^4$, X, $R^4$, $R^5$ and $R^6$ is as defined in the immediately preceeding embodiment; and wherein each of $R^2$, Z, $R^3$, $R^7$, $R^8$, $R^9$, $R^{10}$, $R^{11}$, $R^{12}$, $R^{13}$, $R^{14}$, $R^{15}$, $R^{16}$, $R^{17}$ and n is as defined in the immediately preceeding embodiment.

In another embodiment, there are provided compounds of having a Formula II:

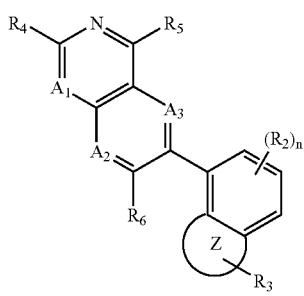

wherein each of $A^1$, $A^2$, $A^3$, $R^2$, $R^3$, $R^4$, $R^5$, $R^6$ and Z is as described above and n is an integer selected from 1, 2 and 3.

In yet another embodiment, there are provided compounds of Formula IIa:

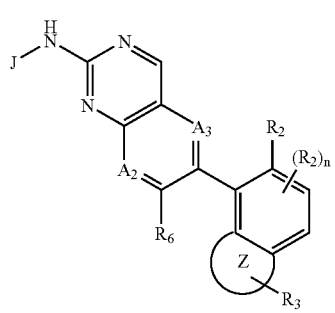

wherein each of $A^2$, $A^3$, $R^2$, $R^6$, J and Z is as described above and each $R^2$, independently, is halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl and n is 0, 1 or 2.

In another embodiment, there are provided compounds having a Formula III

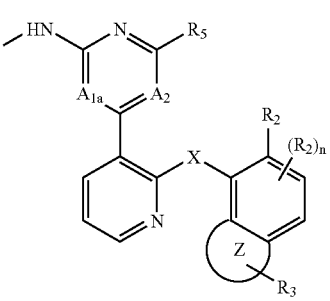

wherein each of $A^1$, $A^2$, $A^3$, $A^4$, $R^2$, $R^4$, $R^5$, X and Z is described above and n is an integer selected from 1, 2 and 3.

In another embodiment, there are provided compounds having a Formula IIIa:

IIIa

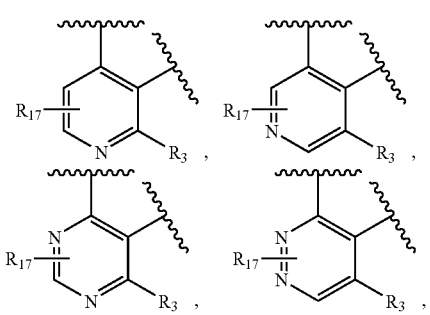

wherein each of $A^{1a}$, $A^2$, $R^3$, $R^5$, X and Z is described above, each $R^2$ independently, is halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl and n is 0, 1 or 2.

In another embodiment, there are provided compounds of Formulas I, II, IIa, III and IIIa, wherein $R^2$ is halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $R^8$ or $R^9$, in conjunction with any of the above or below embodiments.

In another embodiment, the compounds of Formulas I, II, IIa, III or IIIa include

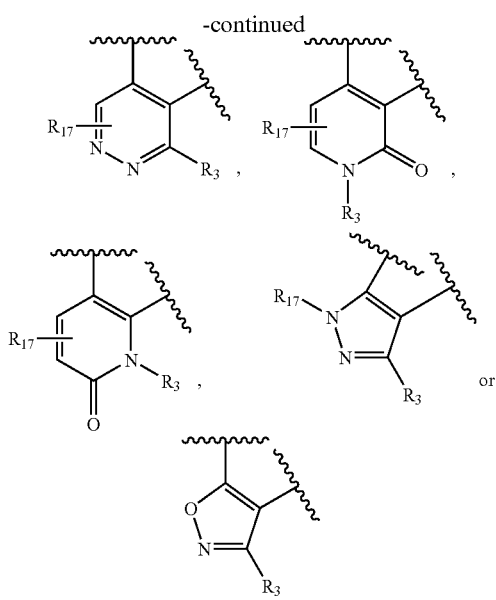

as Z, in conjunction with any of the above or below embodiments.

In another embodiment, the compounds of Formula I include phenyl, pyridyl, pyrimidinyl, triazinyl, pyridazinyl, thiophenyl, furyl, pyrrolyl, pyrazolyl, triazolyl, thiazolyl, thiadiazolyl, oxazolyl, oxadiazolyl, isoxazolyl or isothiazolyl as Z', in conjunction with any of the above or below embodiments.

In another embodiment, the compounds of Formula I include phenyl, pyridyl, pyrimidinyl or pyridazinyl as Z', in conjunction with any of the above or below embodiments.

In another embodiment, the compounds of Formula I include as $R^1$, in conjunction with any of the above or below embodiments.

In another embodiment, the compounds of Formula I include as $R^1$, in conjunction with any of the above or below embodiments.

In another embodiment, the compounds of Formula I include as $R^1$, in conjunction with any of the above or below embodiments.

In another embodiment, the compounds of Formula I include as $R^1$, in conjunction with any of the above or below embodiments.

In another embodiment, the compounds of Formulas I, II or III include H, halo, haloalkyl, $NO_2$, CN, $C_{1-10}$-alkyl, $NR^7R^7$, $NR^7R^8$, $OR^7$, $SR^7$, $OR^8$, $SR^8$, $C(O)R^7$ or $C(O)R^8$ as $R^4$, in conjunction with any of the above or below embodiments.

In another embodiment, the compounds of Formula I, II or III include H, halo, haloalkyl, $NO_2$, CN, —$OC_{1-10}$-alkyl, —$SC_{1-10}$-alkyl, $NH_2$, —$NHC_{1-10}$-alkyl, —$NHC_{3-7}$-cycloalkyl, —$C(O)C_{1-10}$-alkyl or —$S(O)_2C_{1-10}$-alkyl as $R^5$ and $R^6$, independently, in conjunction with any of the above or below embodiments.

In another embodiment, the compounds of Formula I or II include N as $A^1$, in conjunction with any of the above or below embodiments.

In another embodiment, the compounds of Formula I or III include N as $A^{1a}$, in conjunction with any of the above or below embodiments.

In another embodiment, the compounds of Formula I, II or III include N as $A^2$, in conjunction with any of the above or below embodiments.

In another embodiment, the compounds of Formula I, II or IIa include N as $A^3$, in conjunction with any of the above or below embodiments.

In another embodiment, the compounds of Formula I, II, IIa or III include N as $A^4$, in conjunction with any of the above or below embodiments.

In another embodiment, the compounds of Formula I or III include N as $A^{1a}$ and $CR^6$ as each of $A^2$ and $A^3$, independently, in conjunction with any of the above or below embodiments.

In another embodiment, the compounds of Formula I, II or III include N as $A^2$ and $CR^6$ as each of $A^{1a}$ and $A^3$, independently, in conjunction with any of the above or below embodiments.

In another embodiment, the compounds of Formula I or II include N, independently, as both $A^1$ and $A^2$, in conjunction with any of the above or below embodiments.

In another embodiment, the compounds of Formula I or II include N, independently, as both $A^1$ and $A^3$, in conjunction with any of the above or below embodiments.

In another embodiment, the compounds of Formula I or II include N, independently, as both $A^2$ and $A^3$, in conjunction with any of the above or below embodiments.

In another embodiment, the compounds of Formula I or II include N as $A^1$ and $CR^6$ as each of $A^2$ and $A^3$, independently, in conjunction with any of the above or below embodiments.

In another embodiment, the compounds of Formula I include N, independently, as each of $A^1$, $A^2$ and $A^3$, in conjunction with any of the above or below embodiments.

In another embodiment, the compounds of Formula I or II include halo, haloalkyl, $NO_2$, CN, $NR^7R^7$, $OR^7$, $SR^7$, $C(O)R^7$, $S(O)_2R^7$, $C_{1-10}$-alkyl or $C_{3-10}$-cycloalkyl as $R^2$ in conjunction with any of the above or below embodiments.

In another embodiment, the compounds of Formulas I, II, IIa, III or IIIa include halo, haloalkyl, $NO_2$, CN, $NR^7R^7$, $OR^7$ or $C_{1-10}$-alkyl as $R^2$ in conjunction with any of the above or below embodiments.

In another embodiment, the compounds of Formulas I, II, IIa, III or IIIa include halo, haloalkyl, or $C_{1-10}$-alkyl as $R^2$ in conjunction with any of the above or below embodiments.

In another embodiment, the compounds of Formula I include an n of 0 with respect to the number of $R^2$ substitutions, in conjunction with the immediately preceeding embodiment.

In another embodiment, the compounds of Formulas I, II, IIa, III or IIIa include an n of 1 with respect to the number of $R^2$ substitutions, in conjunction with the immediately preceeding embodiment.

In another embodiment, the compounds of Formulas I, II, IIa, III or IIIa include an n of 2 with respect to the number of $R^2$ substitutions, in conjunction with the preceeding embodiment.

In another embodiment, the compounds of Formula I, II or III include an n of 3 with respect to the number of $R^2$ substitutions, in conjunction with the preceeding embodiment.

In another embodiment, the compounds of Formulas I, II, IIa, III or IIIa include $NR^{10}R^{11}$, $NR^{10}C(O)R^{11}$, $NR^{10}C(S)R^{11}$, $NR^{10}C(O)NR^{10}R^{11}$, $NR^{10}(COOR^{11})$, $NR^{10}S(O)_2NR^{10}R^{11}$ or $NR^{10}S(O)_2R^{11}$ as $R^3$, in conjunction with any of the above or below embodiments.

In another embodiment, the compounds of Formulas I, II, IIa, III or IIIa include $NR^{10}R^{11}$, $NR^{10}C(O)R^{11}$ or $NR^{10}S(O)_2R^{11}$ as $R^3$, in conjunction with any of the above or below embodiments.

In another embodiment, the compounds of Formulas I, II, IIa, III or IIIa include $NR^{10}R^{11}$ as $R^3$, in conjunction with any of the above or below embodiments.

In another embodiment, the compounds of Formula I, II or III include H, $NO_2$, $C_{1-10}$-alkyl, $NR^7R^7$, $NR^7R^8$, $OR^7$, $SR^7$, $OR^8$, $SR^8$, $C(O)R^7$ or $C(O)R^8$ as $R^4$, in conjunction with any of the above or below embodiments.

In another embodiment, the compounds of Formula I, II or III include H, halo, haloalkyl, $NO_2$, CN, $-OC_{1-10}$-alkyl, $NH_2$, $-NHC_{1-10}$-alkyl or $-NHC_{3-7}$-cycloalkyl as each of $R^5$ and $R^6$, independently, in conjunction with any of the above or below embodiments.

In another embodiment, the compounds of Formulas I, II, IIa, III or IIIa include compounds wherein $R^3$ is $NR^{10}R^{11}$, $NR^{10}C(O)R^{11}$, $NR^{10}C(S)R^{11}$, $NR^{10}C(O)NR^{10}R^{11}$, $NR^{10}(COOR^{11})$, $NR^{10}S(O)_2NR^{10}R^{11}$ or $NR^{10}S(O)_2R^{11}$;

$R^{10}$ is H or $C_{1-6}$alkyl; and $R^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of $R^{12}$, $R^{13}$, $R^{14}$ or $R^{16}$.

In another embodiment, there are provided compounds of having a general Formula IIb

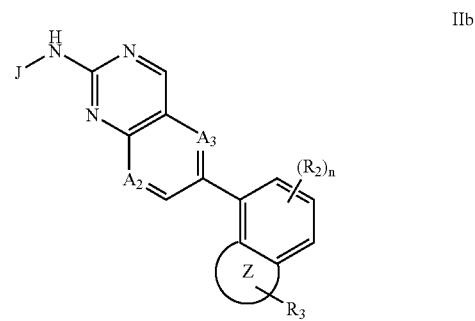

IIb or stereoisomer, tautomer, solvate, pharmaceutically acceptable salt, derivative or prodrug thereof, wherein each of $A^2$ and $A^3$ is, independently, $CR^6$ or N;

J is $R^7$ or $R^8$;

Z is

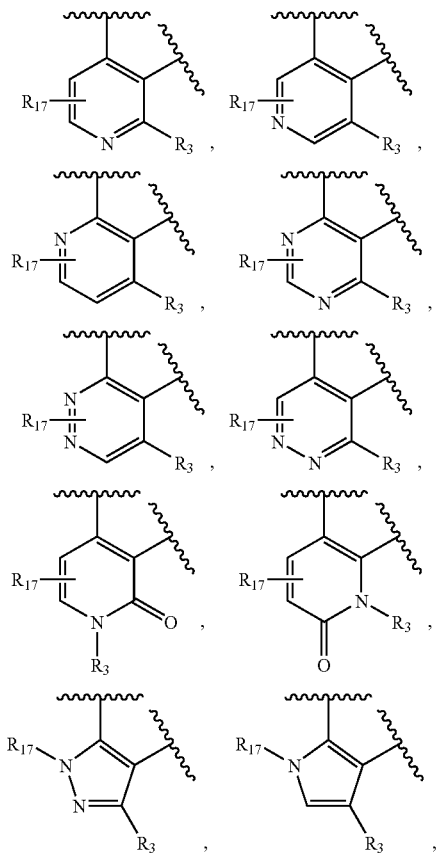

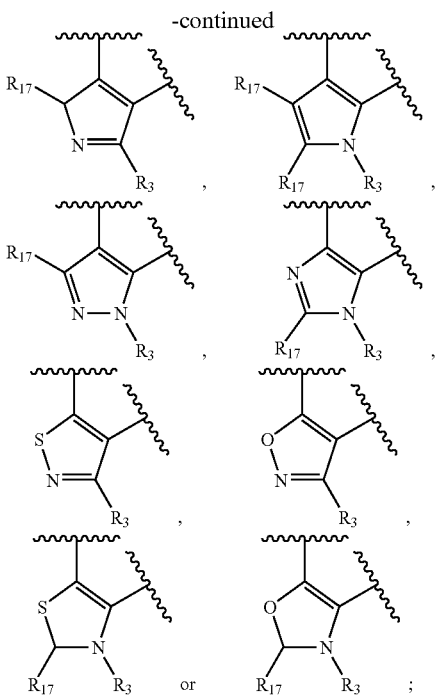

R² is H, halo, haloalkyl, NO₂, CN, NR⁷R⁷, NR⁷R⁸, OR⁷, SR⁷, C(O)R⁷, OC(O)R⁷, COOR⁷, C(O)NR⁷R⁷, C(O)NR⁷R⁸, NR⁷C(O)R⁷, NR⁷C(O)R⁸, NR⁸C(O)NR⁷R⁸, NR⁷(COOR⁷), OC(O)NR⁷R⁸, S(O)₂R⁷, S(O)₂NR⁷R⁸, NR⁷S(O)₂NR⁷R⁸, NR⁷S(O)₂R⁷, NR⁷S(O)₂R⁷, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of R⁸ or R⁹;

R³ is NR¹⁰R¹⁰, NR¹⁰R¹¹, C(O)NR¹⁰R¹⁰, C(S)NR¹⁰R¹⁰, C(O)NR¹⁰R¹¹, C(S)NR¹⁰R¹¹, NR¹⁰C(O)R¹⁰, NR¹⁰C(O)R¹¹, NR¹⁰C(S)R¹⁰, NR¹⁰C(S)R¹¹, NR¹⁰C(O)NR¹⁰R¹⁰, NR¹⁰C(O)NR¹⁰R¹¹, NR¹⁰C(S)NR¹⁰R¹⁰, NR¹⁰C(S)NR¹⁰R¹¹, NR¹⁰(COOR¹⁰), NR¹⁰(COOR¹¹), NR¹⁰C(O)C(O)R¹⁰, NR¹⁰C(O)C(O)R¹¹, NR¹⁰C(O)C(O)NR¹⁰R¹¹, S(O)₂NR¹⁰R¹⁰, S(O)₂NR¹⁰R¹¹, NR¹⁰S(O)₂NR¹⁰R¹¹, NR¹⁰S(O)₂R¹⁰ or NR¹⁰S(O)₂R¹¹;

each R⁶ is, independently, H, halo, haloalkyl, NO₂, CN, NR⁷R⁷, NR⁷R⁸, OR⁷, SR⁷, C(O)R⁷, $C_{1-6}$-alkyl or $C_{3-7}$-cycloalkyl;

R⁷ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of NR⁸R⁹, NR⁹R⁹, OR⁸, SR⁸, OR⁹, SR⁹, C(O)R⁸, OC(O)R⁸, COOR⁸, C(O)R⁹, OC(O)R⁹, COOR⁹, C(O)NR⁸R⁹, C(O)NR⁹R⁹, NR⁹C(O)R⁸, NR⁹C(O)R⁹, NR⁹C(O)NR⁸R⁹, NR⁹C(O)NR⁹R⁹, NR⁹(COOR⁸), NR⁹(COOR⁹), OC(O)NR⁸R⁹, OC(O)NR⁹R⁹, S(O)₂R⁸, S(O)₂NR⁸R⁹, S(O)₂R⁹, S(O)₂NR⁹R⁹, NR⁹S(O)₂NR⁸R⁹, NR⁹S(O)₂NR⁹R⁹, NR⁹S(O)₂R⁸, NR⁹S(O)₂R⁹ or R⁹;

R⁸ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R⁹, oxo, NR⁹R⁹, OR⁹; SR⁹, C(O)R⁹ or a partially or fully saturated or unsaturated 5-6 membered ring of carbon atoms optionally including 1-3 heteroatoms selected from O, N, or S, and optionally substituted independently with 1-3 substituents of R⁹;

R⁹ is H, halo, haloalkyl, CN, OH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, NO₂, NH₂, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

R¹⁰ is H, $C_{1-10}$-alkyl, $C_{2-10}$-alkenyl or $C_{3-10}$-cycloalkyl, each of the $C_{1-10}$-alkyl, $C_{2-10}$-alkenyl and $C_{3-10}$-cycloalkyl optionally comprising 1-4 heteroatoms selected from N, O and S and optionally substituted with one or more substituents of R¹¹, R¹² or R¹⁶, NR¹¹R¹², NR¹²R¹², OR¹¹, SR¹¹, OR¹², SR¹², C(O)R¹¹, OC(O)R¹¹, COOR¹¹, C(O)R¹², OC(O)R¹², COOR¹², C(O)NR¹¹R¹², NR¹²C(O)R¹¹, C(O)NR¹²R¹², NR¹²C(O)R¹², NR¹²C(O)NR¹¹R¹², NR¹²C(O)NR¹²R¹², NR¹²(COOR¹¹), NR¹²(COOR¹²), OC(O)NR¹¹R¹², OC(O)NR¹²R¹², S(O)₂R¹¹, S(O)₂R¹², S(O)₂NR¹¹R¹², S(O)₂NR¹²R¹², NR¹²S(O)₂NR¹¹R¹², NR¹²S(O)₂NR¹²R¹², NR¹²S(O)₂R¹¹, NR¹²S(O)₂R¹², NR¹²S(O)₂R¹¹ or NR¹²S(O)₂R¹²;

R¹¹ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R¹², R¹³, R¹⁴ or R¹⁶;

alternatively, R¹⁰ and R¹¹ taken together form a partially or fully saturated or unsaturated 5-6 membered ring of carbon atoms optionally including 1-3 heteroatoms selected from O, N, or S, and the ring optionally substituted independently with 1-5 substituents of R¹², R¹³, R¹⁴ or R¹⁶;

R¹² is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of R¹³, R¹⁴, R¹⁵ or R¹⁶;

R¹³ is NR¹⁴R¹⁵, NR¹⁵R¹⁵, OR¹⁴; SR¹⁴, OR¹⁵; SR¹⁵, C(O)R¹⁴, OC(O)R¹⁴, COOR¹⁴, C(O)R¹⁵, OC(O)R¹⁵, COOR¹⁵, C(O)NR¹⁴R¹⁵, C(O)NR¹⁵R¹⁵, NR¹⁴C(O)R¹⁴, NR¹⁵C(O)R¹⁴, NR¹⁴C(O)R¹⁵, NR¹⁵C(O)R¹⁵, NR¹⁵C(O)NR¹⁴R¹⁵, NR¹⁵C(O)NR¹⁵R¹⁵, NR¹⁵(COOR¹⁴), NR¹⁵(COOR¹⁵), OC(O)NR¹⁴R¹⁵, OC(O)NR¹⁵R¹⁵, S(O)₂R¹⁴, S(O)₂R¹⁵, S(O)₂NR¹⁴R¹⁵, S(O)₂NR¹⁵R¹⁵, NR¹⁴S(O)₂NR¹⁴R¹⁵, NR¹⁵S(O)₂NR¹⁵R¹⁵, NR¹⁴S(O)₂R¹⁴ or NR¹⁵S(O)₂R¹⁵;

R¹⁴ is a partially or fully saturated or unsaturated 5-8 membered or a saturated or partially or fully saturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$R^{17}$ is H, halo, haloalkyl, CN, OH, $NO_2$, $NH_2$, acetyl, methyl, methoxyl, ethyl, ethoxyl, propyl, propoxyl, isopropyl, cyclopropyl, butyl, isobutyl, sec-butyl, tert-butyl, methylamine, dimethylamine, ethylamine, diethylamine, propylamine, isopropylamine, dipropylamine, diisopropylamine, butylamine, benzyl or phenyl; and n is 0, 1, 2 or 3.

In another embodiment, the compounds of Formula IIa include compounds wherein each $R^2$ independently, is halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl and n is 0, 1 or 2; and J is H, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl, in conjunction with any of the above or below embodiments.

In another embodiment, the compounds of Formula IIa include compounds wherein

J is H, $NO_2$, $C_{1-10}$-alkyl, $NR^7R^7$, $NR^7R^8$, $OR^7$, $SR^7$, $OR^8$, $SR^8$, $C(O)R^7$ or $C(O)R^8$;

$R^6$ is, independently, H, halo, haloalkyl, $NO_2$, CN, —$OC_{1-10}$-alkyl, $NH_2$, —$NHC_{1-10}$-alkyl or —$NHC_{3-7}$-cycloalkyl;

Z is

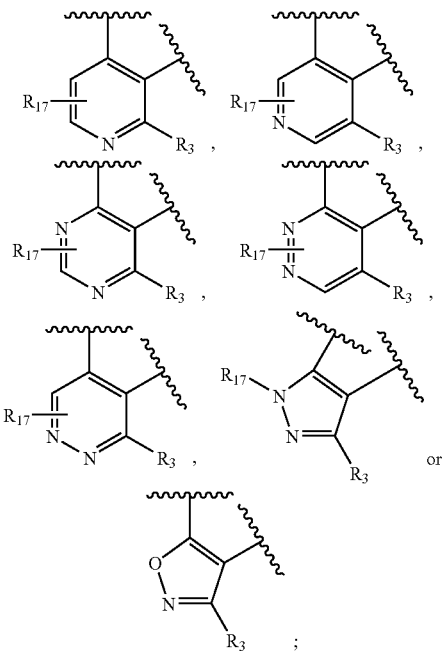

$R^3$ is $NR^{10}R^{11}$, $NR^{10}C(O)R^{11}$, $NR^{10}C(S)R^{11}$, $NR^{10}C(O)NR^{10}R^{11}$, $NR^{10}(COOR^{11})$, $NR^{10}S(O)_2NR^{10}R^{11}$ or $NR^{10}S(O)_2R^{11}$;

$R^{10}$ is H or $C_{1-6}$alkyl; and $R^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of $R^{12}$, $R^{13}$, $R^{14}$ or $R^{16}$, in conjunction with any of the above or below embodiments.

In another embodiment, there are provided compounds of having a general Formula IIIa:

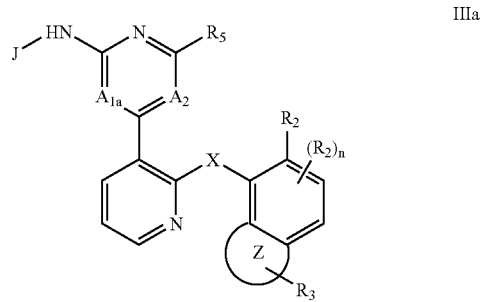

IIIa wherein each $R^2$ independently, is halo, haloalkyl, $NO_2$, CN, $NR^7R^7$, $NR^7R^8$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl and n is 0, 1 or 2; and J is H, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl, in conjunction with any of the above or below embodiments.

In another embodiment, the compounds of general Formula IIa include compounds wherein J is H, NO$_2$, C$_{1-10}$-alkyl, NR$^7$R$^7$, NR$^7$R$^8$, OR$^7$, SR$^7$, OR$^8$, SR$^8$, C(O)R$^7$ or C(O)R$^8$;

Z is

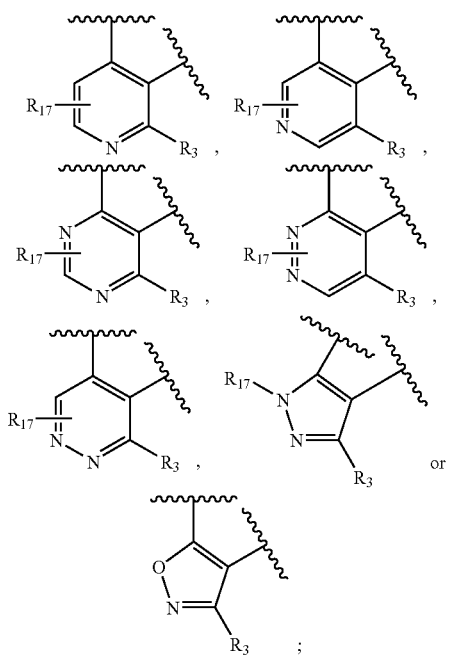

R$^3$ is NR$^{10}$R$^{11}$, NR$^{10}$C(O)R$^{11}$, NR$^{10}$C(S)R$^{11}$, NR$^{10}$C(O)NR$^{10}$R$^{11}$, NR$^{10}$(COOR$^{11}$), NR$^{10}$S(O)$_2$NR$^{10}$R$^{11}$ or NR$^{10}$S(O)$_2$R$^{11}$;

R$^{10}$ is H or C$_{1-6}$alkyl; and

R$^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of R$^{12}$, R$^{13}$, R$^{14}$ or R$^{16}$.

In another embodiment, there are provided compounds of having a general Formula IIIb

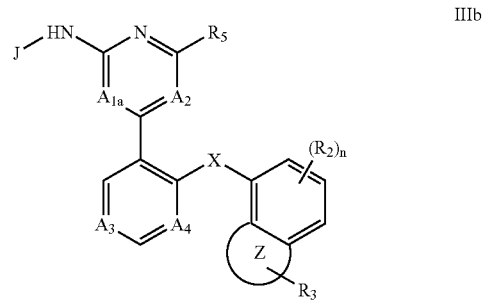

or stereoisomer, tautomer, solvate, pharmaceutically acceptable salt, derivative or prodrug thereof, wherein each of A$^{1a}$, A$^2$, A$^3$ and A$^4$ is, independently, CR$^6$ or N, provided that at least one of A$^{1a}$ and A$^2$ is N;

J is R$^7$ or R$^8$;

X is CR$^6$R$^6$, C(O), NR$^6$, O or S(O)$_p$ wherein p is 0, 1, or 2;

Z is

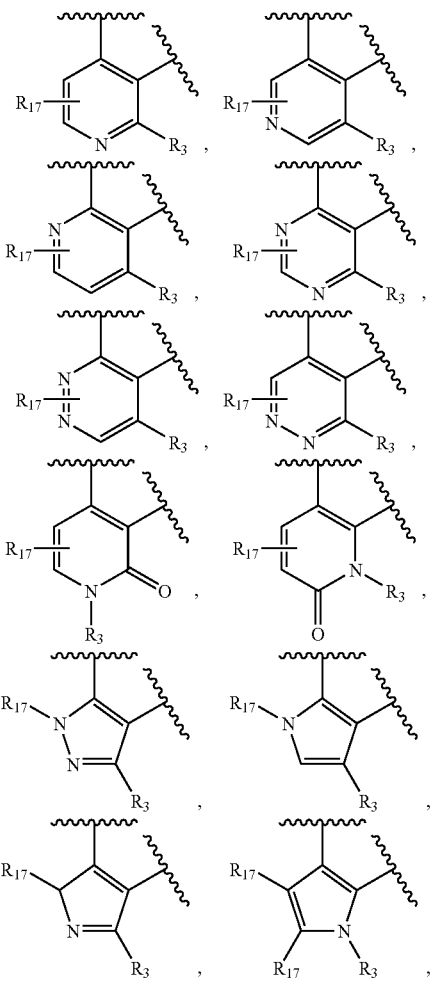

-continued

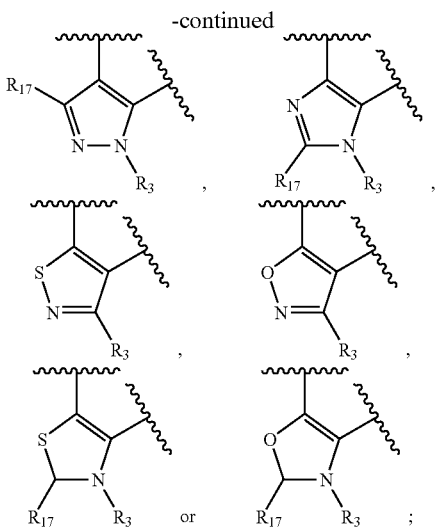

R$^2$ is H, halo, haloalkyl, NO$_2$, CN, NR$^7$R$^7$, NR$^7$R$^8$, OR$^7$, SR$^7$, C(O)R$^7$, OC(O)R$^7$, COOR$^7$, C(O)NR$^7$R$^7$, C(O)NR$^7$R$^8$, NR$^7$C(O)R$^7$, NR$^7$C(O)R$^8$, NR$^8$C(O)NR$^7$R$^8$, NR$^7$(COOR$^7$), OC(O)NR$^7$R$^8$, S(O)$_2$R$^7$, S(O)$_2$NR$^7$R$^8$, NR$^7$S(O)$_2$NR$^7$R$^8$, NR$^7$S(O)$_2$R$^7$, NR$^7$S(O)$_2$R$^7$, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of R$^8$ or R$^9$;

R$^3$ is NR$^{10}$R$^{10}$, NR$^{10}$R$^{11}$, C(O)NR$^{10}$R$^{10}$, C(S)NR$^{10}$R$^{10}$, C(O)NR$^{10}$R$^{11}$, C(S)NR$^{10}$R$^{11}$, NR$^{10}$C(O)R$^{10}$, NR$^{10}$C(O)R$^{11}$, NR$^{10}$C(S)R$^{10}$, NR$^{10}$C(S)R$^{11}$, NR$^{10}$C(O)NR$^{10}$R$^{10}$, NR$^{10}$C(O)NR$^{10}$R$^{11}$, NR$^{10}$C(S)NR$^{10}$R$^{10}$, NR$^{10}$C(S)NR$^{10}$R$^{11}$, NR$^{10}$(COOR$^{10}$), NR$^{10}$(COOR$^{11}$), NR$^{10}$C(O)C(O)R$^{10}$, NR$^{10}$C(O)C(O)R$^{11}$, NR$^{10}$C(O)C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;

R$^5$ is H, halo, haloalkyl, NO$_2$, CN, NR$^7$R$^7$, NR$^7$R$^8$, OR$^7$, SR$^7$, C(O)R$^7$, C$_{1-6}$-alkyl or C$_{3-7}$-cycloalkyl;

each R$^6$ is, independently, H, halo, haloalkyl, NO$_2$, CN, NR$^7$R$^7$, NR$^7$R$^8$, OR$^7$, SR$^7$, C(O)R$^7$, C$_{1-6}$-alkyl or C$_{3-7}$-cycloalkyl;

R$^7$ is H, C$_{1-10}$-alkyl, C$_{2-10}$-alkenyl, C$_{2-10}$-alkynyl or C$_{3-10}$-cycloalkyl, each of the C$_{1-10}$-alkyl, C$_{2-10}$-alkenyl, C$_{2-10}$-alkynyl and C$_{3-10}$-cycloalkyl optionally comprising 1-4 heteroatoms selected from N, O and S and optionally substituted with one or more substituents of NR$^8$R$^9$, NR$^9$R$^9$, OR$^8$, SR$^8$, OR$^9$, SR$^9$, C(O)R$^8$, OC(O)R$^8$, COOR$^8$, C(O)R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$ or R$^9$;

R$^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-3 substituents of R$^9$, oxo, NR$^9$R$^9$, OR$^9$; SR$^9$, C(O)R$^9$ or a partially or fully saturated or unsaturated 5-6 membered ring of carbon atoms optionally including 1-3 heteroatoms selected from O, N, or S, and optionally substituted independently with 1-3 substituents of R$^9$;

R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

R$^{10}$ is H, C$_{1-10}$-alkyl, C$_{2-10}$-alkenyl or C$_{3-10}$-cycloalkyl, each of the C$_{1-10}$-alkyl, C$_{2-10}$-alkenyl and C$_{3-10}$-cycloalkyl optionally comprising 1-4 heteroatoms selected from N, O and S and optionally substituted with one or more substituents of R$^{11}$, R$^{12}$ or R$^{16}$, NR$^{11}$R$^{12}$, NR$^{12}$R$^{12}$, OR$^{11}$, SR$^{11}$, OR$^{12}$, SR$^{12}$, C(O)R$^{11}$, OC(O)R$^{11}$, COOR$^{11}$, C(O)R$^{12}$, OC(O)R$^{12}$, COOR$^{12}$, C(O)NR$^{11}$R$^{12}$, NR$^{12}$C(O)R$^{11}$, C(O)NR$^{12}$R$^{12}$, NR$^{12}$C(O)R$^{12}$, NR$^{12}$C(O)NR$^{11}$R$^{12}$, NR$^{12}$C(O)NR$^{12}$R$^{12}$, NR$^{12}$(COOR$^{11}$), NR$^{12}$(COOR$^{12}$), OC(O)NR$^{11}$R$^{12}$, OC(O)NR$^{12}$R$^{12}$, S(O)$_2$R$^{11}$, S(O)$_2$R$^{12}$, S(O)$_2$NR$^{11}$R$^{12}$, S(O)$_2$NR$^{12}$R$^{12}$, NR$^{12}$S(O)$_2$NR$^{11}$R$^{12}$, NR$^{12}$S(O)$_2$NR$^{12}$R$^{12}$, NR$^{12}$S(O)$_2$R$^{11}$, NR$^{12}$S(O)$_2$R$^{12}$, NR$^{12}$S(O)$_2$R$^{11}$ or NR$^{12}$S(O)$_2$R$^{12}$;

R$^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-5 substituents of R$^{13}$, R$^{14}$, R$^{15}$ or R$^{16}$;

R$^{13}$ is NR$^{14}$R$^{15}$, NR$^{15}$R$^{15}$, OR$^{14}$; SR$^{14}$, OR$^{15}$; SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$R^{17}$ is H, halo, haloalkyl, CN, OH, $NO_2$, $NH_2$, acetyl, methyl, methoxyl, ethyl, ethoxyl, propyl, propoxyl, isopropyl, cyclopropyl, butyl, isobutyl, sec-butyl, tert-butyl, methylamine, dimethylamine, ethylamine, diethylamine, propylamine, isopropylamine, dipropylamine, diisopropylamine, butylamine, benzyl or phenyl; and n is 0, 1, 2 or 3.

Further embodiments of the present invention include compounds of Formulas III and IV, wherein the individual embodiments for each of $A^1$, $A^{1a}$, $A^2$, $A^3$, J, X, Z, $R^2$, $R^3$ $R^5$, $R^6$ and n are as described in embodiments hereinabove.

For example, in another embodiment, the compounds of Formula III or IV include compounds wherein $R^3$ is $NR^{10}R^{11}$, $NR^{10}C(O)R^{11}$, $NR^{10}C(S)R^{11}$, $NR^{10}C(O)NR^{10}R^{11}$, $NR^{10}(COOR^{11})$, $NR^{10}S(O)_2NR^{10}R^{11}$ or $NR^{10}S(O)_2R^{11}$;

$R^{10}$ is H or $C_{1-6}$alkyl; and $R^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of $R^{12}$, $R^{13}$, $R^{14}$ or $R^{16}$.

In other embodiments, Formulas I-IV include the various of the exemplary compounds described in the Experimentals Methods section hereinbelow (see examples 1-85).

The invention also provides methods of synthesizing compounds of Formulas I, II, IIa, III or IIIa. For example, in one embodiment, there is provided a process for synthesizing a compound of Formula I, the process comprising the step of reacting a compound of Formula A

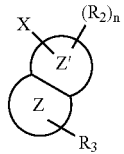

A wherein X is chloro or iodo and $R^2$, $R^3$, Z, Z' and n are as defined herein, with a compound of Formula B

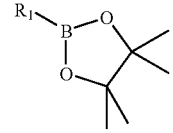

B wherein $R^1$ is as defined herein, to synthesize the compound of Formulas I, II, IIa, III or IIIa. X in Formula A is not limited to a halogen, but may be any suitable leaving group as described in the schematic description and examples herein. Similarly, the boronate is not limited to a cyclic boronate to effect such a coupling.

DEFINITIONS

The following definitions should assist in understanding the invention described herein.

The terms "agonist" and "agonistic" when used herein refer to or describe a molecule which is capable of, directly or indirectly, substantially inducing, promoting or enhancing biological activity of a biological molecule, such as an enzyme or receptor, including B-raf kinase.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$). The term "alkyl" radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. The ring itself, as well as any substituents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "fused" when used alone or in reference to a "ring" or "ring system" refers to a bicyclic ring having 2 common atoms. For example, as shown in Formula II, the two common atoms are both carbon, when Z' is phenyl and is fused to ring Z.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d] isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino, and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The term "alkylthio" embraces radicals containing a linear or branched alkyl radical, of one to ten carbon atoms, attached to a divalent sulfur atom. An example of "alkylthio" is methylthio, (CH$_3$S—).

The term "haloalkylthio" embraces radicals containing a haloalkyl radical, of one to ten carbon atoms, attached to a divalent sulfur atom. An example of "haloalkylthio" is trifluoromethylthio.

The term "aminoalkyl" embraces linear or branched alkyl radicals having one to about ten carbon atoms any one of which may be substituted with one or more amino radicals. Examples of aminoalkyl radicals include "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II, III and IV. Similarly, the term "Formula II", "Formula III" and "Formula IV" includes any sub formulas.

The term "pharmaceutically-acceptable" when used with reference to a compound of Formulas I-IV is intended to refer to a form of the compound that is safe for administration. For example, a salt form, a solvate, a hydrate or derivative form of a compound of Formula I or of Formula II, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-IV are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-IV may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-IV include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, II, III or IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I, II, III or IV. A "pharmaceutically-acceptable prodrug" as used herein, denotes a prodrug which is pharmaceutically acceptable. Pharmaceutically acceptable modifications to the compounds of Formula I are readily appreciated by those of ordinary skill in the art.

The compound(s) of Formula I, II, III or IV may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels raf kinases in the mammal.

General Synthetic Procedures

The present invention further comprises procedures for the preparation of a compound of Formulas I, II, III and IV.

The compounds of Formulas I-IV can be synthesized according to the procedures described in the following exemplary schematic methods 1-9, wherein the substituents are as defined for Formulas I-IV, above, except where further noted. The synthetic methods described below are merely exemplary, and the compounds of the invention may be synthesized by alternate routes as appreciated by persons of ordinary skill in the art.

The following list of abbreviations used throughout the specification represent the following and should assist in understanding the invention:

| | |
|---|---|
| ACN, MeCN | acetonitrile |
| BSA | bovine serum albumin |
| Cs$_2$CO$_3$ | cesium carbonate |
| CHCl$_3$ | chloroform |
| CH$_2$Cl$_2$, DCM | dichloromethane, methylene chloride |
| mCPBA | meta-chloro peroxybenzoic acid |
| DIBAL | diisobutylaluminum hydride |
| DIC | 1,3-diisopropylcarbodiimide |
| DIEA, (iPr)$_2$NEt | diisopropylethylamine |
| DME | dimethoxyethane |
| DMF | dimethylformamide |
| DMSO | dimethylsulfoxide |
| EDC | 1-(3-dimethylaminopropyl)-3-ethylcarbodiimide |
| Et$_2$O | diethyl ether |
| EtOAc | ethyl acetate |
| FBS | fetal bovine serum |
| G, gm | gram |
| h, hr | hour |
| H$_2$ | hydrogen |

-continued

| | |
|---|---|
| Na$_2$SO$_4$ | sodium sulfate |
| PBS | phospate buffered saline |
| Pd/C | palladium on carbon |
| Pd(PPh$_3$)$_4$ | palladium(0)triphenylphosphine tetrakis |
| Pd(dppf)Cl2 | palladium(1,1-bisdiphenylphosphinoferrocene) II chloride |
| Pd2(dba)3 | bis(dibenzylideneacetone) palladium |
| POCl3 | phosphorus oxychloride |
| PyBop | benzotriazol-1-yl-oxy-tripyrrolidino-phosphonium hexafluorophosphate |
| RT | room temperature |
| TBTU | O-benzotriazol-1-yl-N,N,N',N'-tetramethyluronium tetrafluoroborate |
| TEA, Et3N | triethylamine |
| TFA | trifluoroacetic acid |
| THF | tetrahydrofuran |

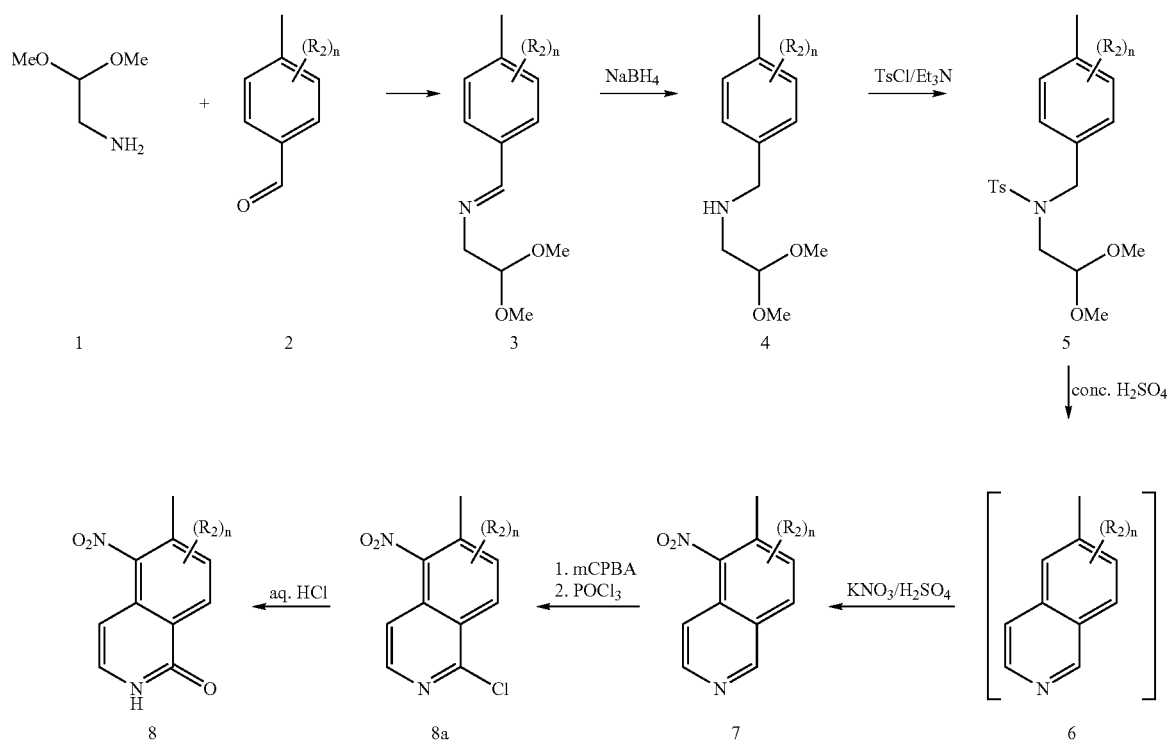

Scheme 1

| | |
|---|---|
| HATU | O—(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HPLC | high pressure liquid chromatography |
| IPA, IpOH | isopropyl alcohol |
| K$_2$CO$_3$ | potassium carbonate |
| KI | potassium iodide |
| MgSO$_4$ | magnesium sulfate |
| MeOH | methanol |
| N$_2$ | nitrogen |
| NaBH$_4$ | sodium borohydride |
| NaHCO$_3$ | sodium bicarbonate |
| NaOCH$_3$ | sodium methoxide |
| NaOH | sodium hydroxide |

A method for making intermediates 8, which are useful for making various of the compounds of Formulas I-IV (where Z is a pyridine ring and Z' is phenyl), is described in scheme 1. As shown, a ketone-protected amine 1 can be condensed with a benzaldehyde 2 to form the corresponding imine 3. Imine 3 can be reduced with known reducing reagents, such as NaBH$_4$, under suitable conditions to provide the corresponding amine adduct 4. The amino functionality of compound 4 may be protected with a suitable protecting group, such as a tosylate as shown, under suitable conditions to provide the protected amine compound 5. Compound 5 can be cyclized by treatment with a suitable acid, such as conc. H$_2$SO$_4$, which deprotects the amine and carbonyl groups in situ to yield an isoquinoline compound 6. The isoquinoline compound 6 may be nitrated using KNO$_3$ under known acidic conditions to form the nitro-compound 7. As shown, a nitro-substituted isoquinoline 7 can be halogenated with a chlorine atom by known methods, such as with an oxidant (mCPBA) in the presence of a known chlorinating reagent such as POCl$_3$, to form the chloro-adduct compound 8a. The chlorine of compound 8a can subsequently be converted to the corresponding ketone using conventional methods, such as with aqueous acidic conditions, as shown above in Scheme 1, to yield the corresponding, useful nitro-lactam intermediate 8.

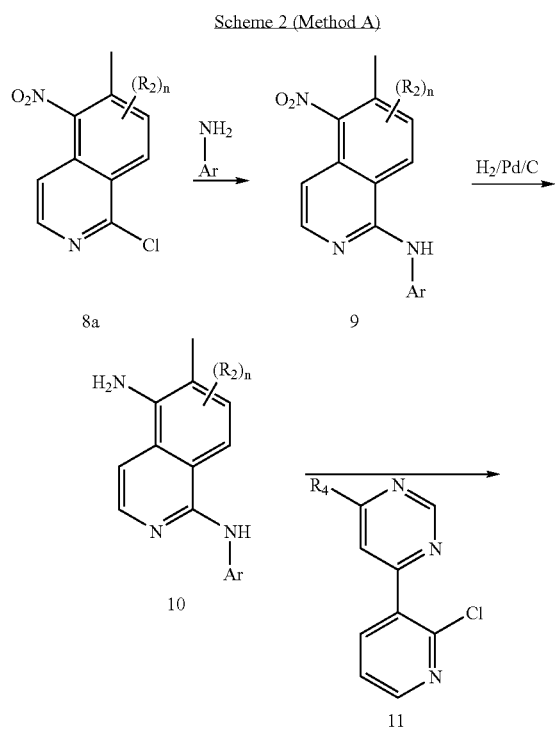

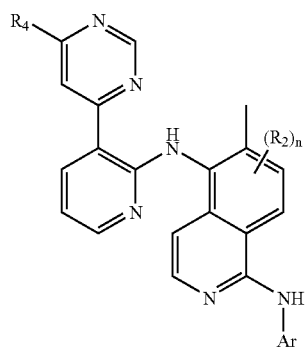

A method for making a compound 12 of Formulas I-IV (where Z is a pyridine ring, Z' is phenyl, R$^1$ is an amino-linked pyrimidyl-pyridine wherein X is —NH—, A$^{1a}$ is N and A$^2$ and A$^3$ are both CH, and R$^3$ is —NR$^{10}$R$^{11}$ wherein R$^{10}$ is H and R$^{11}$ is an aryl group) is described in scheme 2. For the purposes of the exemplary compounds described hereinbelow, this method or general synthetic strategy is designated as Method A. As shown, the chlorine of compound 8a can be displaced by an aryl amine under suitable conditions to generate an aryl amine-linked isoquinoline 9. The nitro group of compound 9 can be reduced to compound 10 using traditional methods, such as by hydrogenation in the presence of a suitable palladium catalyst as shown in scheme 2 above. The amino functionality of compound 10 may be reacted with a desirably substituted chloro-pyridine 11 to provide the final compound 12, of Formula I, II, III or IV.

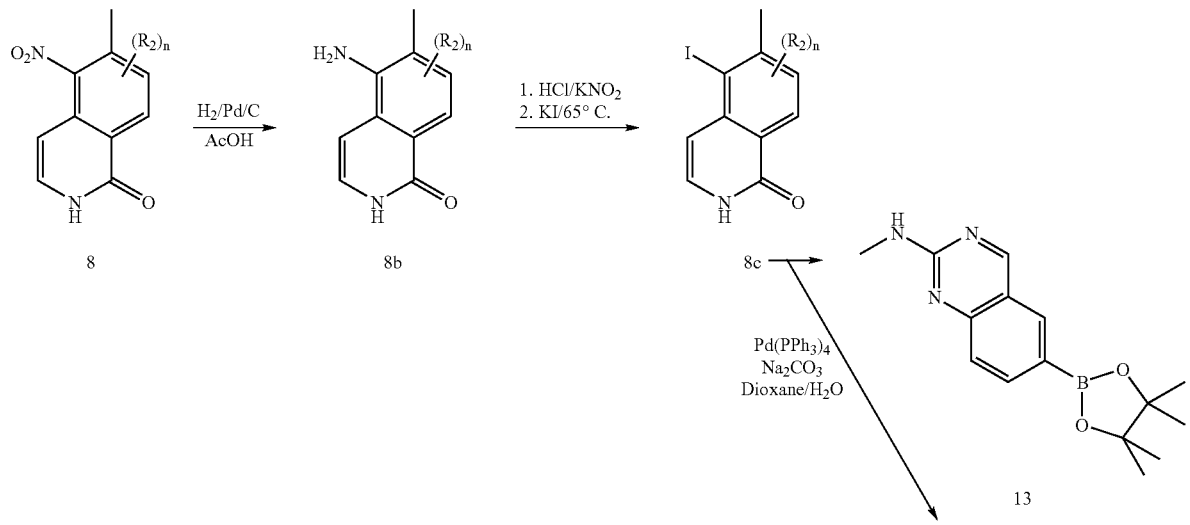

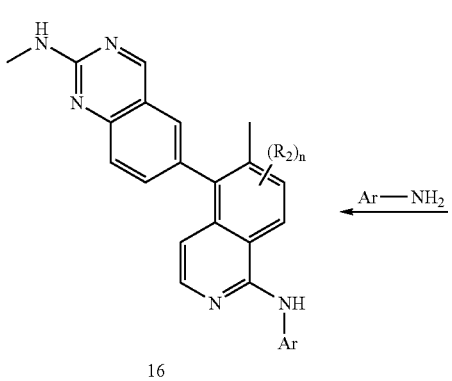
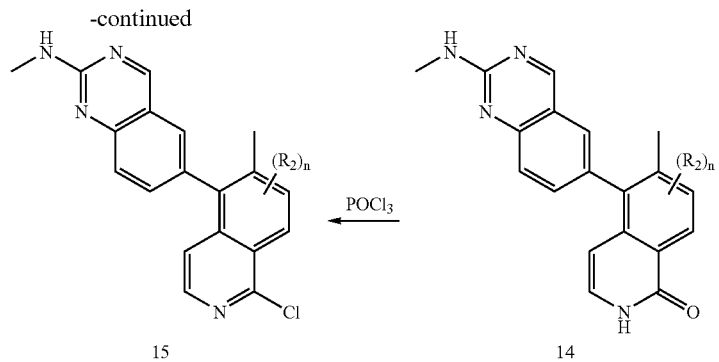

A method for making a compound 16 of Formulas I-IV (where Z is a pyridine ring, Z' is phenyl, $R^1$ is 2-amino-methyl quinazoline wherein $A^1$ is N and $A^2$ and $A^3$ are both CH, and $R^3$ is —$NR^{10}R^{11}$ wherein $R^{10}$ is H and $R^{11}$ is an aryl group) is described in Scheme 3. For the purposes of the exemplary compounds described hereinbelow, this method or general synthetic strategy is designated as Method B. As shown, the nitro group of compound 8 can be reduced by known methods, such as by iron metal in the presence of a suitable acid, such as acetic acid, or simply by hydrogenation in the presence of an acid, such as acetic acid as shown to form the corresponding amino compound 8b. The amino group of compound 8b can be converted to the corresponding iodine compound 8c by first quaternizing the amine and displacing it with an iodine from a suitable source such as KI, as shown in Scheme 3. The amino group of compound 8b can be converted to the corresponding iodine compound 8c by first converting the amine to a quaternary amine and displacing it with an iodine atom from a suitable source such as KI, as shown in Scheme 3. The iodinated compound 8c can be reacted with desired boronic acids, under suitable Suzuki conditions or under Suzuki-like conditions to form the coupled intermediate 14. The carbonyl of compound 14 can be converted to the corresponding chloride compound 15, using $POCl_3$, which chlorine can then be displaced by an aryl amine under suitable conditions to generate an aryl amine-linked isoquinoline final compound 16.

The Suzuki method is a reaction using a borane reagent, such as a dioxaborolane intermediate 13 and a suitable leaving group containing reagent, such as the 6-LG-Z—Z' ring compound 8c (LG=X=I, Br, Cl). As appreciated to one of ordinary skill in the art, Suzuki reactions also use palladium as a catalyst, in the presence of a suitable base, such as a carbonate base, bicarbonate or an acetate base, in a suitable solvent, such as toluene, acetonitrile, DMF or an aqueous-organic solvent combination (such as dioxanes/water) or a biphasic system of solvents (such as toluene/aq. $NaCO_3$). Suitable palladium reagents include $Pd(PPh_3)_4$, $Pd(OAc)_2$ or $Pd(dppf)Cl_2$. Where LG is a halide, the halide may be an iodide, a bromide or even a chloride (chloro-pyridyl or chloro-picolinyl B rings undergo suzuki reactions in the presence of $Pd(OAc)_2$). In addition, a corresponding halo intermediate, the C-D ring piece or the B-A ring piece, may be converted to the borane, such as the dioxaborolane as described in Scheme 6. Other LGs are also suitable. For example, Suzuki couplings are known to occur with a sulfonate, such as trifluoromethanesulfonate, as the leaving group.

In this fashion, final compounds 16 of Formulas I-IV, wherein Z is an unsubstituted pyridine ring, $R^1$ is an optionally substituted isoquinoline ($A^1$, $A^2$ and $A^3$ are all CH), optionally substituted quinazoline (as shown above), or optionally substituted aza-isoquinoline or aza-quinazoline (wherein $A^1$ is either N or CH and one of $A^2$ and $A^3$ is N while the other of $A^2$ and $A^3$ is CH), can be made.

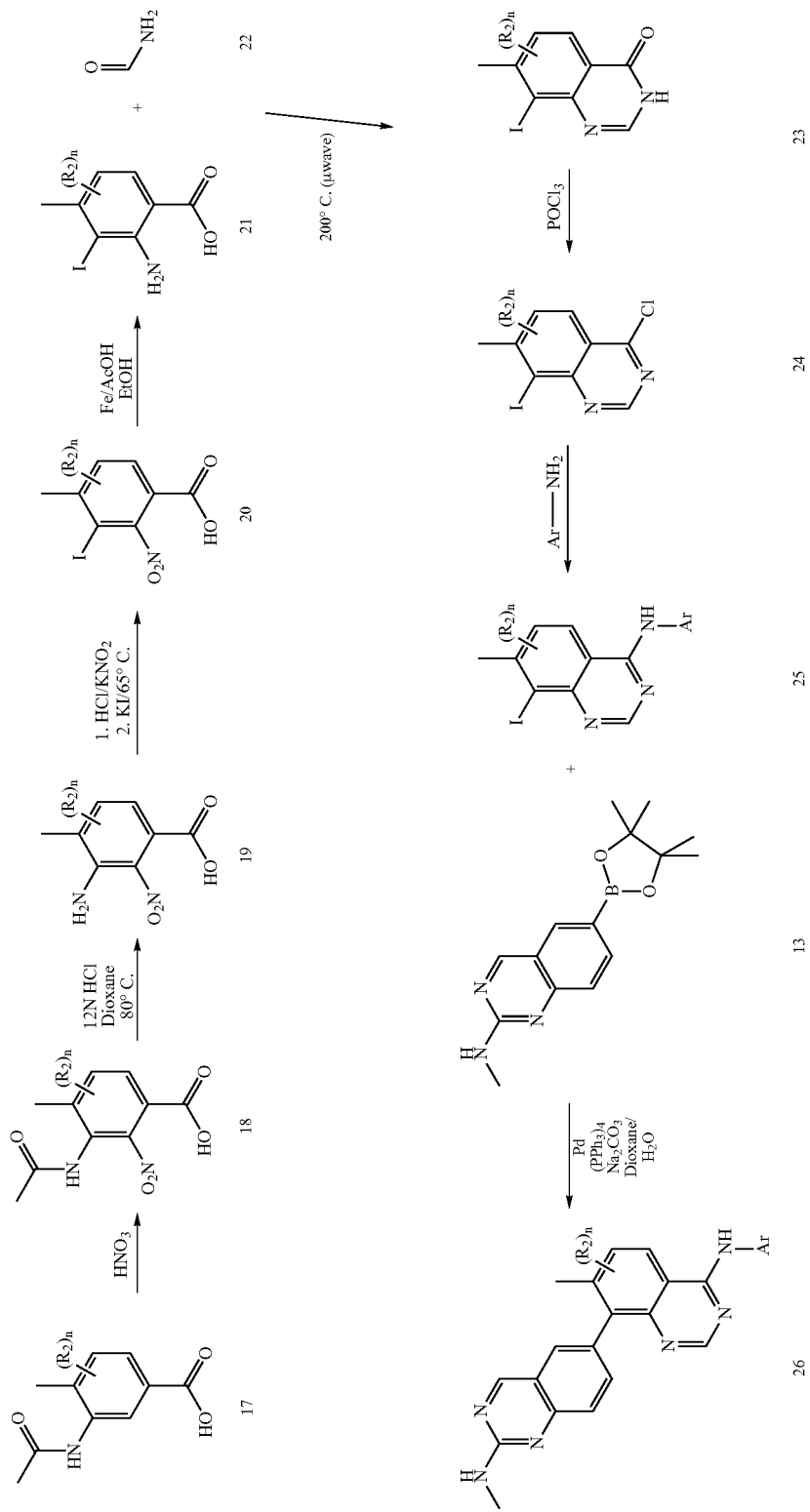

A method for making a final compound 26 of Formulas I-IV (where Z is a pyrimidine ring, Z' is phenyl, R¹ is 2-amino-methyl quinazoline wherein A¹ is N and A² and A³ are both CH, and R³ is —NR¹⁰R¹¹ wherein R¹⁰ is H and R¹¹ is an aryl group) is described in Scheme 4. For the purposes of the exemplary compounds described hereinbelow, this method or general synthetic strategy is designated as Method C. As shown, an acetamido-substituted benzoic acid 8 can be nitrated by known methods, such as with nitric acid, to form the corresponding nitro compound 18. The acetamido group of compound 8b can be converted to the corresponding iodine compound 18 can be converted to the corresponding amine 19 by treatment with a suitable acid, such as HCl, as shown in Scheme 4. Amine 19 can be converted to the corresponding iodo compound 20, by conventional methods, such as that described above in Scheme 3. The nitro group of compound 20 can be reduced by known methods, such as by iron metal in the presence of a suitable acid, such as acetic acid, to form the corresponding amino compound 21 (see Scheme 3). Amine compound 21 can be treated with an amine-aldehyde reagent 22 under suitable conditions, such as in a microwave, to form carbox-quinazoline 23. As described in Scheme 3 (compounds 14-26), the carbonyl of compound 23 can be converted to the chloride 24, which can be displaced to afford the aryl amine substituted iodo intermediate 25. The iodinated compound 25 can be reacted with desired boronic acids 13, under suitable Suzuki conditions or under Suzuki-like conditions as described in Scheme 3, to form the final compound 26.

The general method of scheme 3 (Method C), as shown, is not limited to preparing compounds of Formulas II and IIa alone, but may also be used to make other compounds within the scope of the present invention. For example, Method C may be used to prepare compounds of Formula I having the following R¹ groups respectively: free 2-amino-quinazoline (A), 2-amido-aminoquinazolines (B), 1H-pyrazolo[3,4-b]pyridine connected at the 5-position (C), 3-NHMe-1H-indazoles connected at the 6-position (D), 3-amino-1-methyl-1H-indazoles connected at the 6-position (E), 3-NHMe-1-methyl-1H-indazoles connected at the 6-position (F), 3-methyl-1H-indazole connected via the 5-position (G) and 8-methyl-2-(methylamino)pyrido[2,3-d]pyrimidin-7(8H)-one connected via the 8-position (H). The synthesis of the above-mentioned compounds is similar to that of compound 26 but using with a different boronic ester 13 in the final step. The exemplary R¹ groups of Formula I are illustrated below.

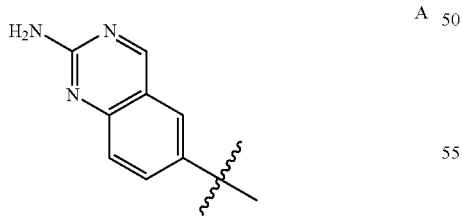

A

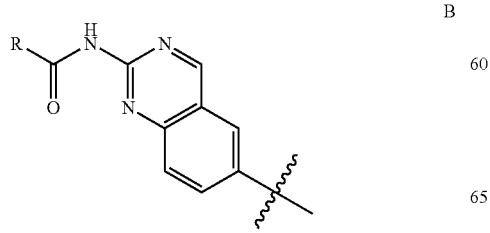

B

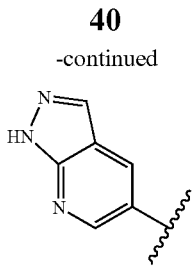

C

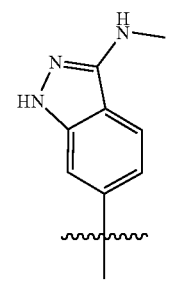

D

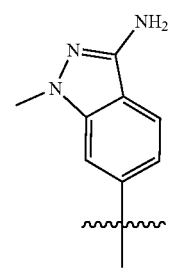

E

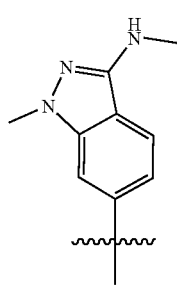

F

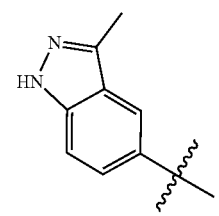

G

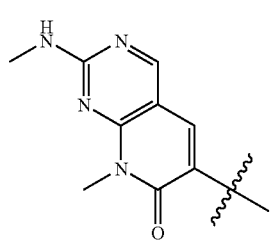

H

Scheme 5 (Method D)

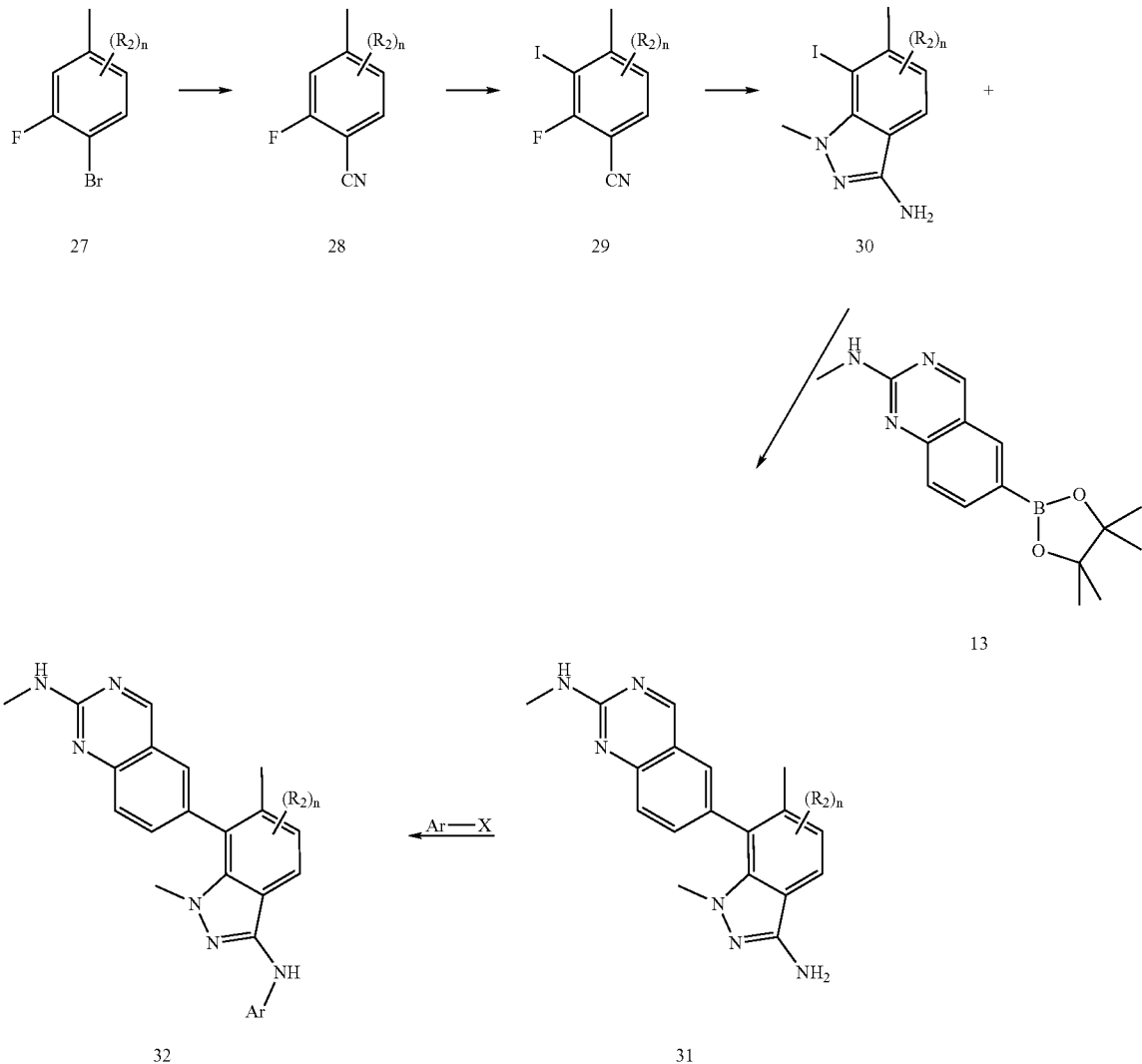

A method for making a compound 32 of Formulas I-IV (where Z is a pyrazole ring, Z' is phenyl, R$^1$ is 2-amino-methyl quinazoline wherein A$^1$ is N and A$^2$ and A$^3$ are both CH, and R$^3$ is —NR$^{10}$R$^{11}$ wherein R$^{10}$ is H and R$^{11}$ is an aryl group) is described in scheme 5. For the purposes of the exemplary compounds described hereinbelow, this method or general synthetic strategy is designated as Method D. As shown, the bromide group of a methyl, fluoro, bromo-compound 27 can be converted to the corresponding cyano group by known methods, such as displacement by CuCn, NaCN or KCN, to form the corresponding cyano compound 28. Compound 28 can be iodinated under suitable conditions, such as with suitable strong bases and iodinating reagents, like LiTMP and iodine as described in Scheme 5 above. Compound 29 can be converted to the corresponding amino-benzopyrazole compound 30 by treatment with methylhydrazine. The amino compound 30 can be reacted with a desired boronic acid 13, as described in schemes 3 and 4 above, to form the coupled intermediate 31. The amine of compound 31 can then be functionalized, such as converted to an aryl amine 32 by treating with a desired aryl-halide (X is a suitable leaving group, such as a halogen).

In this fashion, final compounds 32 of Formulas I-IV, wherein Z is an substituted pyrazole ring, R$^1$ is an optionally substituted isoquinoline (A$^1$, A$^2$ and A$^3$ are all CH), optionally substituted quinazoline (as shown above), or optionally substituted aza-isoquinoline or aza-quinazoline (wherein A$^1$ is either N or CH and one of A$^2$ and A$^3$ is N while the other of A$^2$ and A$^3$ is CH), can be made.

Scheme 5a

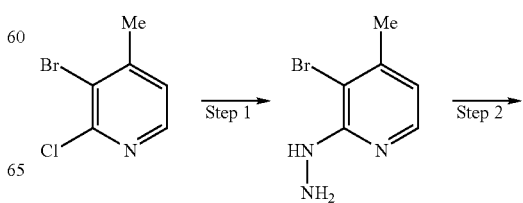

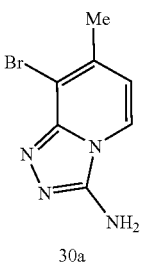

30a

8-Bromo-7-methyl-[1,2,4]triazolo[4,3-a]pyridin-3-amine 30a can be prepared as follows (prepared analogously to the method described in *J. Heterocyclic Chem.* 1978, 15, 439., 65748-6).

Step 1

A mixture of 3-bromo-2-chloro-4-methylpyridine (3.63 g, 17.6 mmol) and hydrazine, anhydrous (6.00 ml, 191 mmol) was heated to 110° C. After 4 h, the reaction was cooled to room temperature and basified with 5N NaOH. The solid was filtered, washed consecutively with H2O, Et2O and pentane, and dried in vacuo to give 3.04 g (86%) of a white amorphous solid. MS (M+H)+ 202.

Step 2

To a suspension of 1-(3-bromo-4-methylpyridin-2-yl)hydrazine (2.00 g, 9.90 mmol) in 20 mL of 2-propanol was added cyanogen bromide (1.07 g, 10.1 mmol) at 25° C. The reaction was then heated to 70° C. After 2.5 h another 80 mg cyanogen bromide was added. The reaction was filtered while hot and the solid was washed with 2-propanol and pentane and dried in vacuo to give a light yellow amorphous solid. MS (M+H)+ 229.

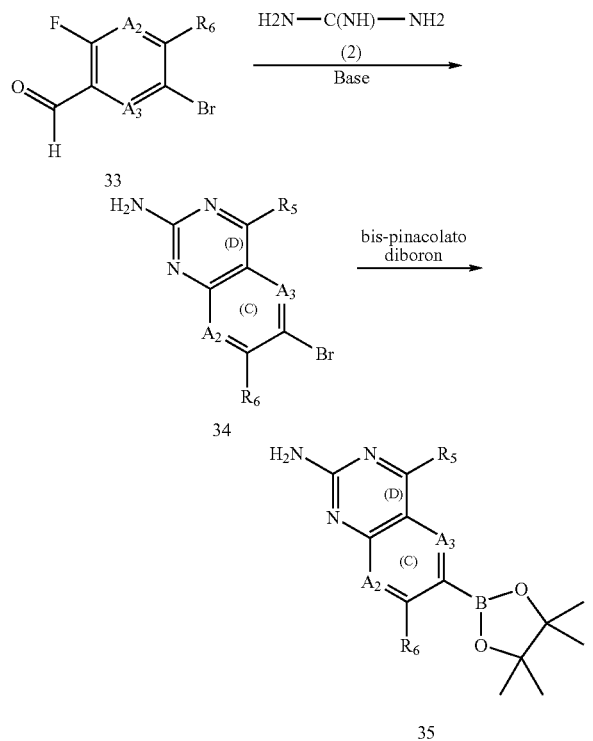

A boron substituted-aryl nitrogen-containing bicyclic ring 35, which is a quinazoline where both of $A^2$ and $A^3$ are CH, an aza-quinazoline where only one of $A^2$ and $A^3$ is nitrogen, or a diaza-quinazoline ring where both of $A^2$ or $A^3$ are nitrogen, can be prepared according to the method generally described in Scheme 6. Compound 35 is generally referred to herein and throughout the specification as the C-D ring portion of the compounds of Formulas I-IV. As shown, a halo-arylcarboxaldehyde 33 can be treated with guanidine in the presence of a suitable solvent and a mild base, such as a tertiary amine base such as DIEA and/or NMP, to form the 2-amino-6-bromo nitrogen-containing bicyclic ring 34. 2-amino-6-bromo nitrogen-containing bicyclic ring 34 can then be treated with bis(pinacolato)diboron to form the corresponding 6-dioxaborolane 35. The 2-amino group of compound 35 can be alkylated to the corresponding methyl-amino compound 13 (see scheme 3) by conventional methods. The 2-amino group of compound 35 can be converted to the corresponding amide compound using well known procedures for amide bond formation, such as by methods using an acid halide and a mild base (eg. acetyl chloride and pyridine).

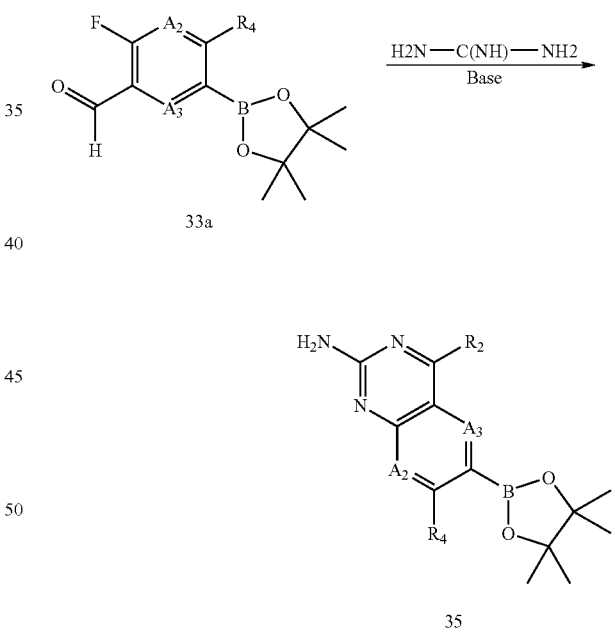

Alternatively, 2-amino-6-dioxaborolan-2-yl-aryl nitrogen-containing bicyclic ring 35, can be prepared according to the method generally described in Scheme 6A. As shown, a 2-halo-5-(4,4,5,5-tetramethyl-1,2,3-diboroxalan-2-yl) arylcarboxaldehyde 33a can be treated with guanidine in the presence of a suitable solvent under suitable heat, such as in a microwave reactor, to form the 2-amino-6-dioxaborolane nitrogen-containing bicyclic ring 35.

Scheme 6B

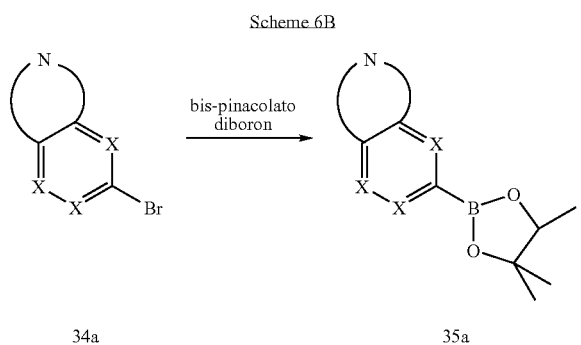

Scheme 6C

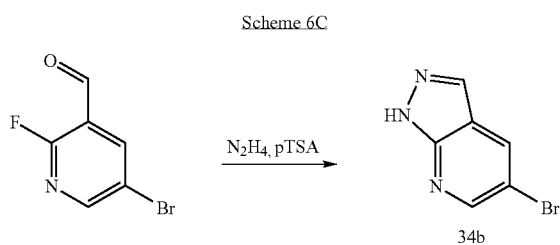

Exemplary Method for Compounds of Scheme 6C

Preparation of 5-bromo-1H-pyrazolo[3,4-b]pyridine

A mixture of 5-bromo-2-fluoronicotinaldehyde (0.580 g, 2.8 mmol), 4-methylbenzenesulfonic acid (0.060 g, 0.35 mmol) and anhydrous hydrazine (0.450 ml, 14 mmol) in 5 mL of i-PrOH was heated at 145° C. for 15 min in the microwave (Initiator by Biotage). The reaction was diluted with $H_2O$ and the solid was filtered washed with $H_2O$ and air-dried to give a white amorphous solid. MS $(M+H)^+$ 198, 200.

Scheme 6D

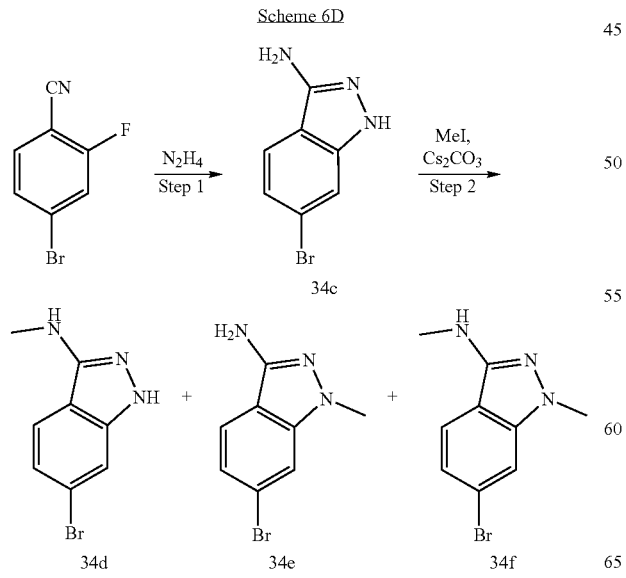

Exemplary Method for Compounds of Scheme 6D

Preparation of 6-bromo-N-methyl-1H-indazol-3-amine, 6-bromo-1-methyl-1H-indazol-3-amine, and 6-bromo-N,1-dimethyl-1H-indazol-3-amine Step 1

To a solution of 4-bromo-2-fluorobenzonitrile (5.00 g, 25.0 mmol) in n-butanol (30.0 ml), charged to a 150 mL microwave reaction vessel, hydrazine hydrate (2.50 ml, 51.4 mmol) was added. The reaction mixture was stirred at 112° C. for o/n. Upon cooling a ppt formed. This was collected by filtration and washed with EtOAc 3× before drying under vacuum. MS $(M+H)^+$ 212, 214.

Step 2

To a solution of 6-bromo-1H-indazol-3-amine (2.34 g, 11.0 mmol) in DMF (20 ml), charged to a 150 mL round bottom, iodomethane (0.756 ml, 12.1 mmol), and cesium carbonate (3.60 g, 11.0 mmol) was added at 23° C. The reaction mixture was stirred for 4 hrs. The reaction mixture was diluted with water and DCM. The aqueous was extracted with DCM×3. The combined organics were washed with brine, dried over magnesium sulfate and concentrated under vacuum. The resulting residue was loaded on to silica and purified by column chromatography (15-75% EtOAc in hexanes). This separated the two mono-alkylated products from the di-alkylated (MS $(M+H)^+$ 240, 242.) The mono-alkylated products were separated by prep HPLC and identities assigned by NMR. MS $(M+H)^+$ 226, 228.

Scheme 6E

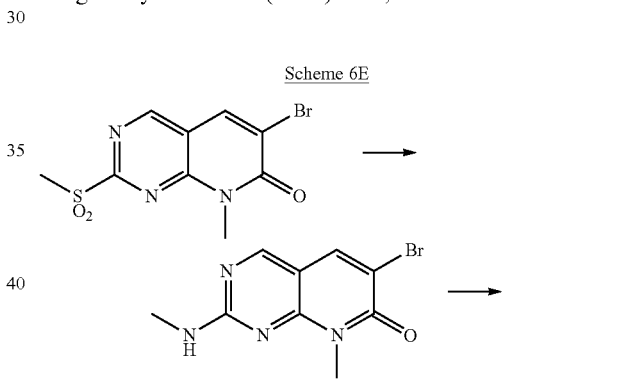

*Bioorganic & Medicinal Chemistry Letters* (2005), 15(7), 1931-1935.

Exemplary Method for Compounds of Scheme 6E

Preparation of 8-methyl-2-(methylamino)-6-(4,4,5,5-tetramethyl-1,3,2-dioxaborolan-2-yl)pyrido[2,3-d]pyrimidin-7(8H)-one Step 1

Charged a flask with 6-bromo-8-methyl-2-(methylsulfonyl)pyrido[2,3-d]pyrimidin-7(8H)-one (0.910 g, 2.86 mmol, prepared by reference in Scheme 6E) and 10.0 mL IPA. Chilled suspension to 0° C. and treated with methylamine 33% wt. solution in ethanol (1.78 ml, 14.3 mmol). After addition was complete, the bath was removed and the reaction mixture was allowed to warm to ambient temperature and stirred overnight. The crude reaction mixture was filtered and washed with ethanol (2×30 mL) and air-dried to afford a white microcrystalline solid: 6-bromo-8-methyl-2-(methylamino)pyrido[2,3-d]pyrimidin-7(8H)-one (0.637 g, 82.8% yield). MS (M+H)+ 269, 271.

Step 2

In a small microwave reaction vessel, 6-bromo-8-methyl-2-(methylamino)pyrido[2,3-d]pyrimidin-7(8H)-one (0.200 g, 0.743 mmol), 4,4,5,5-tetramethyl-2-(4,4,5,5-tetramethyl-1,3,2-dioxaborolan-2-yl)-1,3,2-dioxaborolane (0.566 g, 2.23 mmol), and potassium acetate (0.365 g, 3.72 mmol) were dissolved in DMSO (1.00 ml, 14.1 mmol) and then treated with PdCl2dppf (0.0544 g, 0.0743 mmol). The reaction mixture was heated to 150° C. for 20 minutes in the microwave. (m/z=M+H=235). The reaction mixture was then diluted into approximately 25 mL of water and filtered. The precipitate was stirred in diethyl ether for 30 minutes and then filtered. The filter cake was washed with several portions of diethyl ether and air-dried to afford 8-methyl-2-(methylamino)-6-(4,4,5,5-tetramethyl-1,3,2-dioxaborolan-2-yl)pyrido[2,3-d]pyrimidin-7(8H)-one (0.150 g, 63.8% yield). MS ([ArB(OH)2+H])+ 235, (M+H)+ 317.

The methods of Schemes 6 and 6a-6e may also apply to synthesis of the 4-NH$_2$ substituted quinazolines, azaquinazolines and diazaquinazolines, as determined and appreciated by persons of ordinary skill in the art.

A method (alternative to the method of scheme 5) for making a compound 40 of Formulas I-IV (where Z is a pyrazole ring, Z' is phenyl, R$^1$ is 2-amino-methyl quinazoline wherein A$^1$ is N and A$^2$ and A$^3$ are both CH, and R$^3$ is —NR$^{10}$R$^{11}$ wherein R$^{10}$ is H and R$^{11}$ is an aryl group) is described in scheme 7. For the purposes of the exemplary compounds described hereinbelow, this method or general synthetic strategy is designated as Method F. As shown, the amino group of a amino, iodo-benzoic acid 36 can be converted to the corresponding fluoro group by known methods, such as displacement by a suitable fluoride source, to form the corresponding fluoro compound 37. The acid of compound 37 can be converted to the corresponding amide 38 under suitable conditions. For example, compound 38 may be made by coupling the acid 37 to an amine, such as an aryl amine as shown, under suitable amide bond forming conditions. Reagents commonly used to form amide bonds include, without limitation, BOP, HATU, TBTU, HOBT and the like, and such reactions may be run in the presence of a suitable base. Alternatively, the peptide bond may be formed via an acid chloride, or other suitable leaving group of the acid functionality. Such activating reagents are described below. Compounds 40 may be made from corresponding amides (as shown above), amidines, and thioamides (not shown), as appreciated by the skilled artisan.

Z—Z' ring systems, generally designated and referred to throughout the specification as the "B" ring may be substituted with various substitutions including R$^{11}$ ring systems, generally designated and referred to throughout the specification as the "A" ring system, by various amide bond forming methods mentioned in Scheme 7. To form an amide bond, an

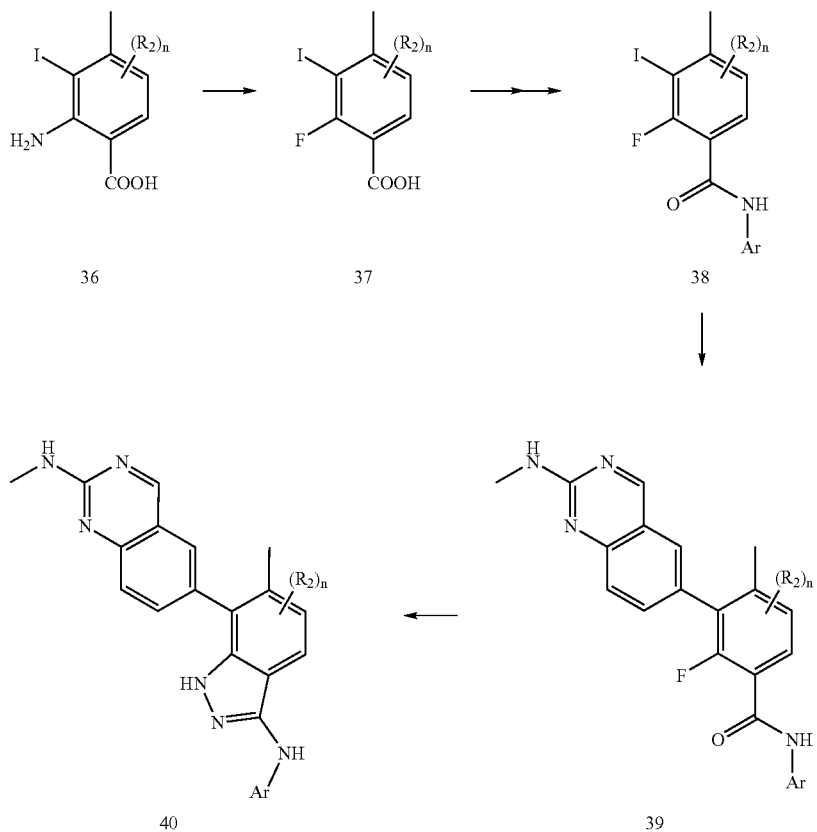

ester, a carbamate, a urea, and the like, each of the two starting materials must possess one or the other of an electrophilic (E+) and a nucleophile (Nu−). The acid may be the E+ by activating it with a component "X". X refers generally to a "leaving group" such as a halide (bromine, chlorine, iodine or fluorine), alkylsulfonate and other known groups (also see definitions herein). Nu− refers generally to a nucleophilic species such as a primary or secondary amine, an oxygen, a sulfur or a anionic carbon species—examples of nucleophiles include, without limitation, amines, hydroxides, alkoxides and the like. E+ refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoylchlorides, sulfonyl chlorides, acids activated with activating reagents such as TBTU, HBTU, HATU, HOBT, BOP, PyBOP and carbodiimides (DCC, EDC and the like), and other electrophilic species including halides, isocyanates, daizonium ions and the like.

The coupling of rings B and A (not shown) can be brought about using various conventional methods. For example, an amide or a sulfonamide linkage where the Nu– is an amine can be made utilizing an amine on either the B or A rings and an acid chloride or sulfonyl chloride on the other of either the B or A rings. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates where Nu– is an amine, anhydrides where Nu– is an oxygen, reverse amides where Nu– is an amine and E+ is an acid chloride, ureas, thioamides and thioureas where the respective carbonyl oxygen is a sulfur, thiocarbamates where the respective carbonyl oxygen and/or carbamate oxygen is a sulfur, and the like, can be made utilizing similar methods as described for the amide or sulfonamide bond above. While the above methods are so described, they are not exhaustive, and other methods for linking rings A and B together may be utilized as appreciated by those skilled in the art.

The iodo-benzamide compound 38 can be coupled to the desired $R^1$ bicyclic ring via a Suzuki-type reaction conditions, as described here schemes 3 and 4. The coupled adduct 39 can be cyclized to form the final indazole compound 40 by conventional methods, such as conversion of the amide to the corresponding thioamide with a suitable reagent such as Lawesson's Reagent, and then treating the thioamide with hydrazine to form the desired indazole.

In this fashion, final compounds 40 of Formulas I-IV, wherein Z is an unsubstituted pyrazole ring, $R^1$ is an optionally substituted isoquinoline ($A^1$, $A^2$ and $A^3$ are all CH), optionally substituted quinazoline (as shown above), or optionally substituted aza-isoquinoline or aza-quinazoline (wherein $A^1$ is either N or CH and one of $A^2$ and $A^3$ is N while the other of $A^2$ and $A^3$ is CH), can be made.

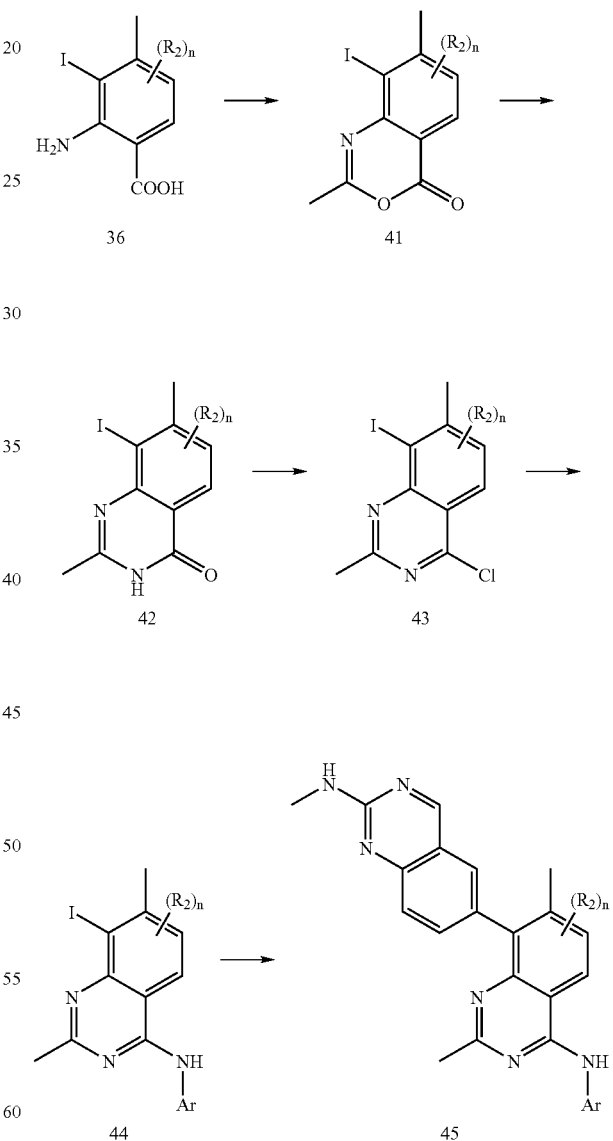

A method (alternative to the method of scheme 4) for making a final compound 45 of Formulas I-IV (where Z is a pyrimidine ring, Z' is phenyl, $R^1$ is 2-amino-methyl quinazoline wherein $A^1$ is N and $A^2$ and $A^3$ are both CH, and $R^3$ is —NR$^{10}$R$^{11}$ wherein R$^{10}$ is H and R$^{11}$ is an aryl group) is described in scheme 8. For the purposes of the exemplary compounds described hereinbelow, this method or general synthetic strategy is designated as Method H. As shown, an amino, iodo-benzoic acid 36 can be converted to the corresponding cyclic ester adduct 41 by known methods, such as by treatment with acetic anhydride. Cyclized ester 41 can be converted to the corresponding cyclic amide 42 under suitable conditions. For example, compound 42 may be made by treatment of compound 41 with liquid ammonia followed by aqueous sodium hydroxide. The carbonyl of compound 42 can then be converted to the chloride 43, which can be reacted with a suitable amine to afford the final compound 46. The last steps may be performed using the methods described in scheme 4 (see compounds 23-25).

In this fashion, final compounds 45 of Formulas I-IV, wherein Z is a substituted pyrimidine ring, R$^1$ is an optionally substituted isoquinoline (A$^1$, A$^2$ and A$^3$ are all CH), optionally substituted quinazoline (as shown above), or optionally substituted aza-isoquinoline or aza-quinazoline (wherein A$^1$ is either N or CH and one of A$^2$ and A$^3$ is N while the other of A$^2$ and A$^3$ is CH), can be made.

Scheme 9 (Method E)

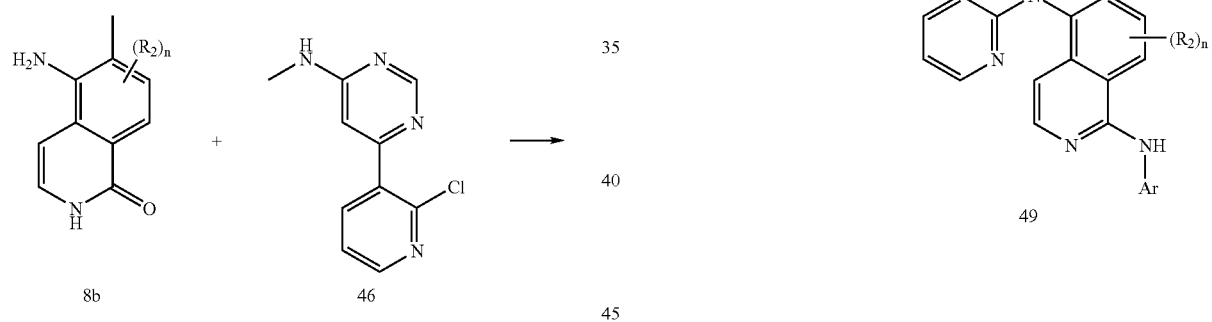

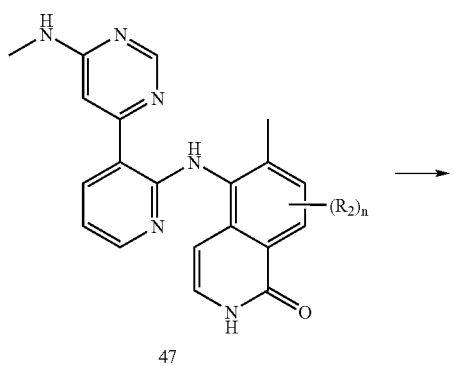

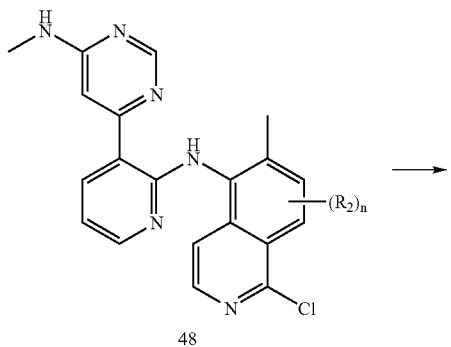

A method for making a compound 49 of Formulas I-IV (where Z is a pyridine ring, Z' is phenyl, R$^1$ is an amino-linked pyrimidyl-pyridine wherein X is —NH—, A$^2$ is N and A$^{1a}$ and A$^3$ are both CH, and R$^3$ is —NR$^{10}$R$^{11}$ wherein R$^{10}$ is H and R$^{11}$ is an aryl group) is described in Scheme 9. For the purposes of the exemplary compounds described hereinbelow, this method or general synthetic strategy is designated as Method E. As shown, compound 8b can be reacted with a chloro-pyridine compound 46, under suitable conditions, for afford compound 47. As described above in scheme 4, the carbonyl of compound 47 may be converted via a chloride 48 to the corresponding amine substituted target compound 49.

In this fashion, final compounds 49 of Formulas I-IIIa, wherein Z is an unsubstituted pyridine ring, R$^1$ is an amino-linked pyrimidyl-pyridine wherein X is —NH—, A$^2$ is N and A$^{1a}$ and A$^3$ are both CH, and R$^3$ is —NR$^{10}$R$^{11}$ wherein R$^{10}$ is H and R$^{11}$ is an aryl group, can be made.

Scheme 10 (Method I)

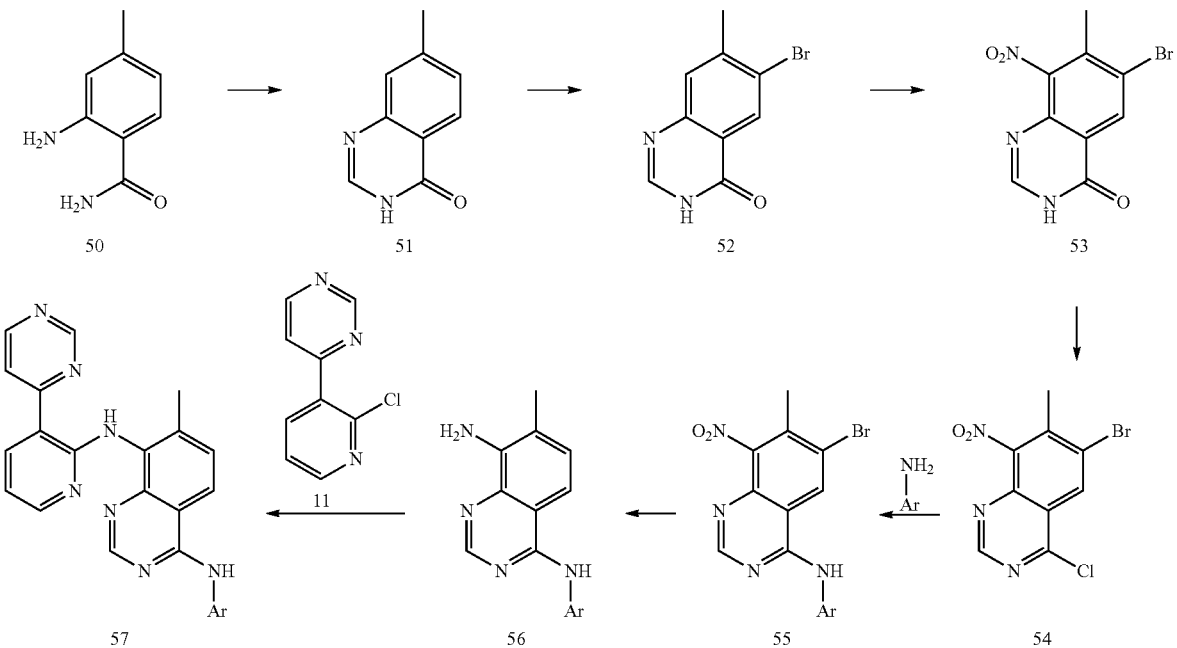

Scheme 10 illustrates an additional method for making compounds 57 of Formulas I, III and IIIa. As described herein, one may go through the process describing the transformation of intermediates 50 through 56 to prepare compounds 57. Exemplary procedures are provided in Examples 332-343. Further, while compound 57 as shown possesses an unsubstituted pyrimidine ring, the invention is not so limited, and the pyrimidine ring may have thereon one or more desired $R^4$ group substitutions, as described herein. Accordingly, scheme 10 is generally applicable to compounds of the present invention, as appreciated by those of ordinary skill in the art.

Scheme 11 (Method J)

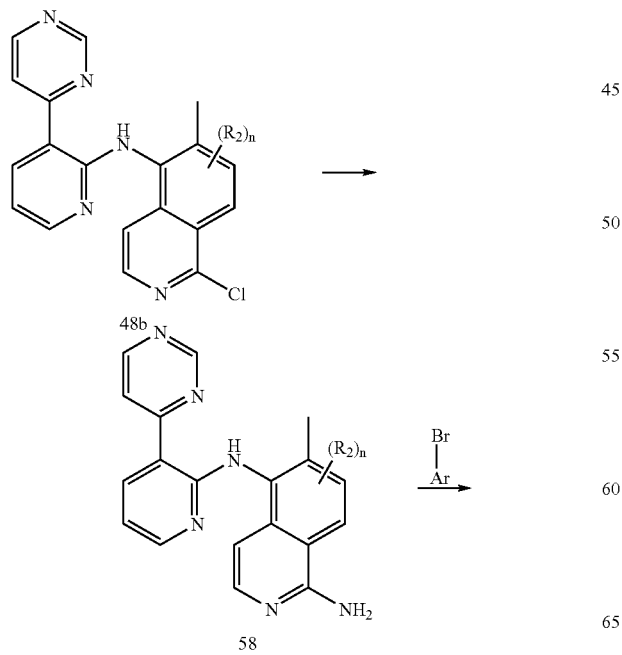

-continued

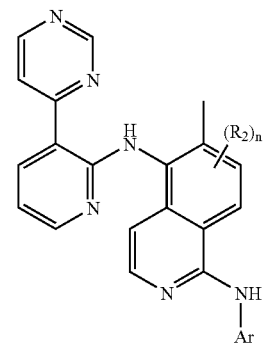

Scheme 11 illustrates an additional method for making compounds 12 of Formulas I, III and IIIa. As described herein, one may go through the process describing the transformation of intermediates 48b through 58 to prepare compounds 12. Exemplary procedures are provided in Examples 344a-344. Further, while compound 12 as shown possesses an unsubstituted pyrimidine ring, the invention is not so limited, and the pyrimidine ring may have thereon one or more desired $R^4$ group substitutions, as described herein. Accordingly, scheme 11 is generally applicable to compounds of the present invention, as appreciated by those of ordinary skill in the art.

Scheme 12 (Method K)

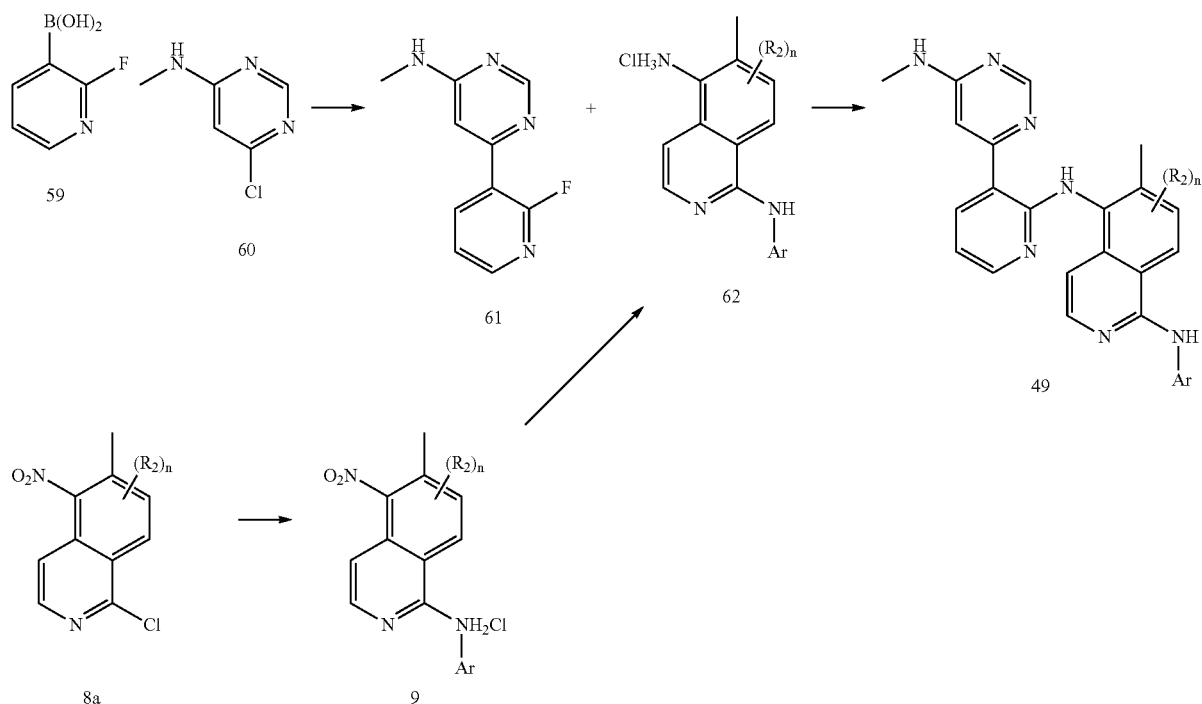

Scheme 12 illustrates an additional method for making compounds 49 of Formulas I, III and IIIa. As described herein, one may go through the process describing the transformation of intermediates 8a through 61 and 62 to prepare compounds 49. Exemplary procedures are provided in Examples 346-353. In addition, while compound 60 is shown as a chloro-N-methylpyrimidine, other desired aryl and heteroaryl halides may be used, such as those shown in examples 348 and 353. Accordingly, scheme 12 is generally applicable to compounds of the present invention, as appreciated by those of ordinary skill in the art.

Scheme 13 (Method L)

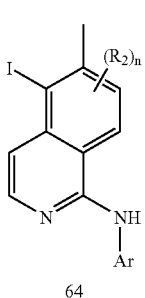

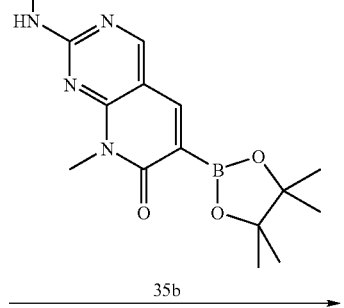

-continued

Scheme 13 illustrates an additional method for making compounds 65 of Formula I. As described herein, one may go through the process describing the transformation of intermediates 8b through 64 as shown to prepare compounds 65. Exemplary procedures are provided in Examples 354-377. In addition, while compound 35b is shown as N-methyl azaquinazolin-one boronic acid, other desired aryl and heteroaryl boronic acids may be used, such as those adducts shown in examples 358-377. Accordingly, scheme 13 is generally applicable to compounds of the present invention, as appreciated by those of ordinary skill in the art.

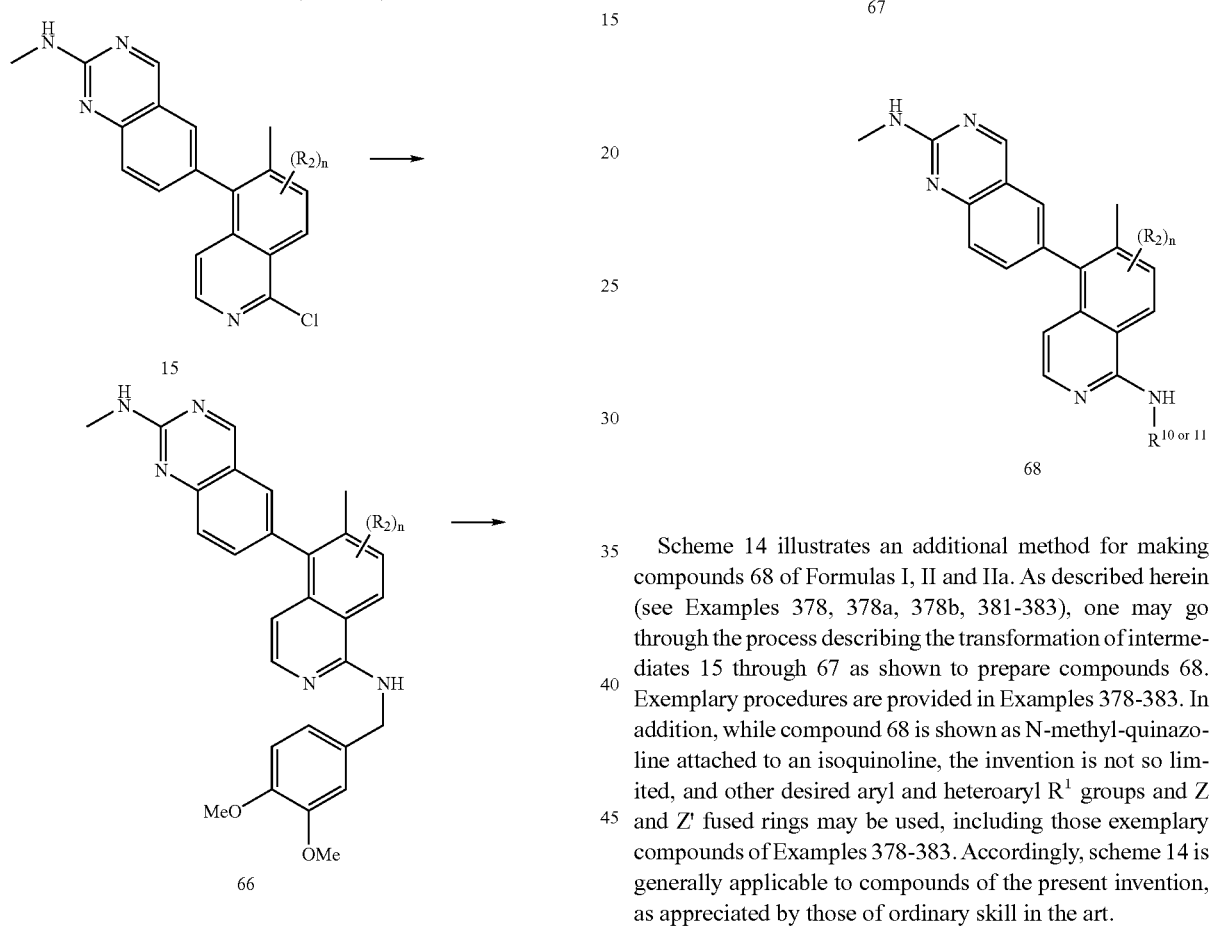

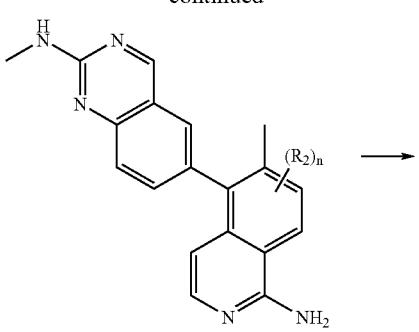

Scheme 14 illustrates an additional method for making compounds 68 of Formulas I, II and IIa. As described herein (see Examples 378, 378a, 378b, 381-383), one may go through the process describing the transformation of intermediates 15 through 67 as shown to prepare compounds 68. Exemplary procedures are provided in Examples 378-383. In addition, while compound 68 is shown as N-methyl-quinazoline attached to an isoquinoline, the invention is not so limited, and other desired aryl and heteroaryl $R^1$ groups and Z and Z' fused rings may be used, including those exemplary compounds of Examples 378-383. Accordingly, scheme 14 is generally applicable to compounds of the present invention, as appreciated by those of ordinary skill in the art.

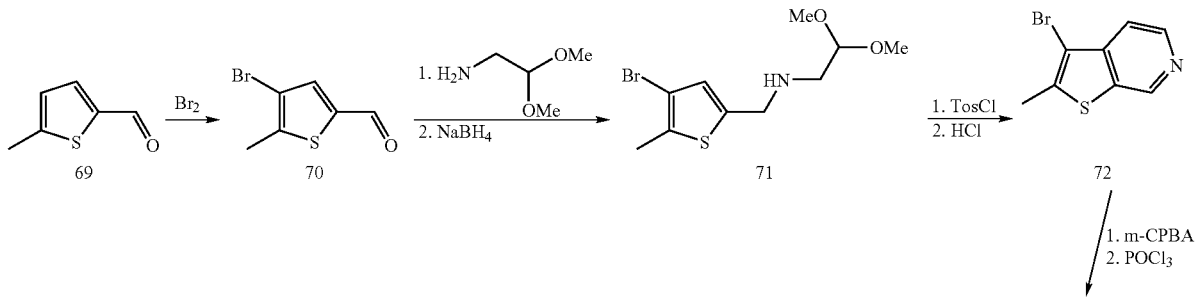

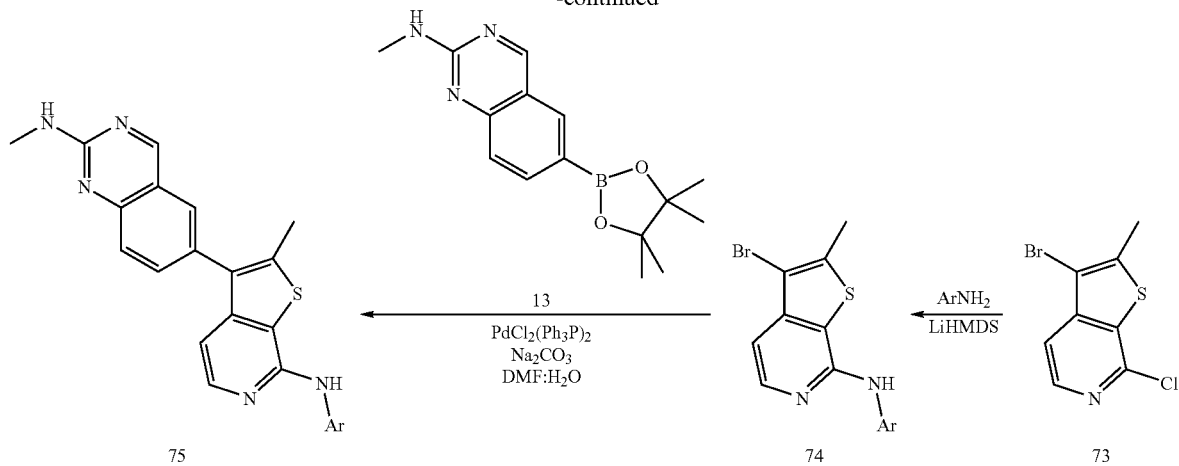

Scheme 15 illustrates an additional method for making compounds 75 of Formula I. As described herein, one may go through the process describing the transformation of intermediates 69 through 74 as shown to prepare compounds 75. Exemplary procedures thereto are provided in Examples 384-393. In addition, while compound 68 is shown as N-methyl-quinazoline attached to an isoquinoline, the invention is not so limited, and other desired aryl and heteroaryl R¹ groups and Z and Z' fused rings may be used, including those exemplary compounds of Examples 392-393. Accordingly, scheme 15 is generally applicable to compounds of the present invention, as appreciated by those of ordinary skill in the art.

Scheme 16 (Method O)

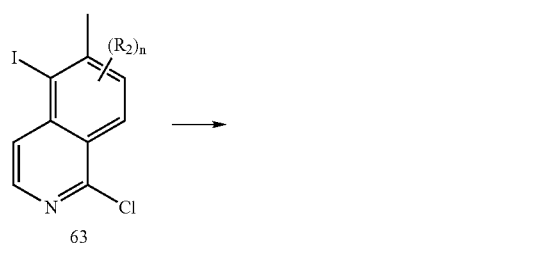

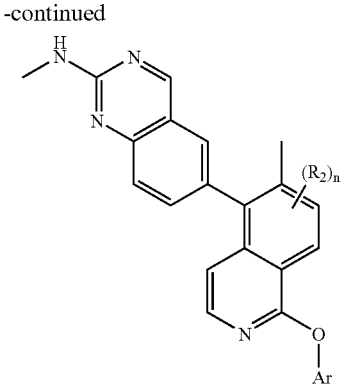

Scheme 16 illustrates an additional method for making compounds 77 of Formulas I, II and IIa. As described herein, one may go through the process describing the transformation of intermediates 63 through 76 as shown to prepare compounds 77. Exemplary procedures thereto are provided in Examples 394-395. In addition, while compound 77 is shown as N-methyl-quinazoline attached to an isoquinoline, the invention is not so limited, and other desired aryl and heteroaryl R¹ groups and Z and Z' fused rings may be used, including those exemplary compounds of Examples 394-395. Accordingly, scheme 16 is generally applicable to compounds of the present invention, as appreciated by those of ordinary skill in the art.

Scheme 17 (Method P)

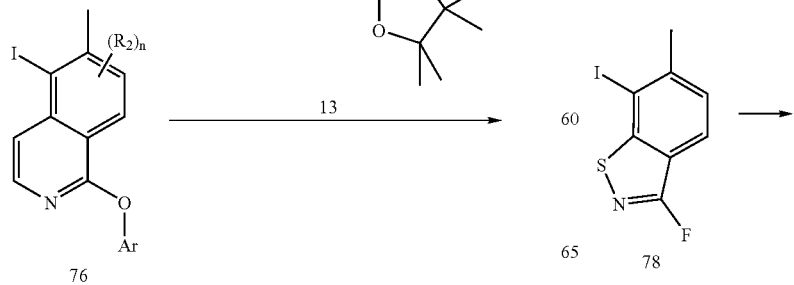

61
-continued

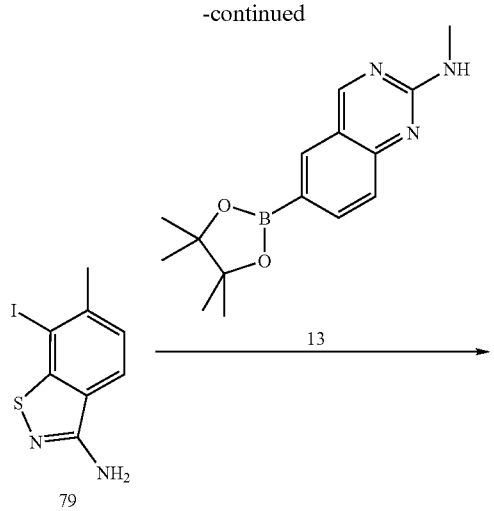

62
-continued

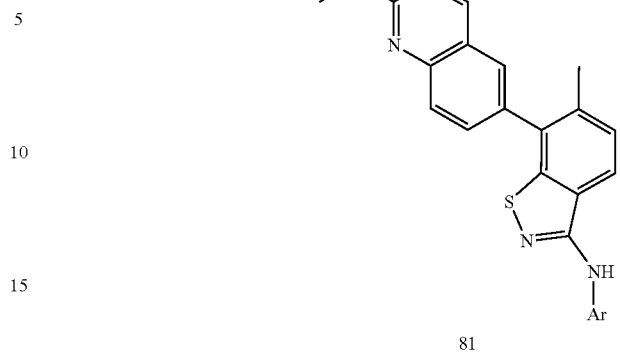

reference: WO2006094187

Scheme 17 illustrates an additional method for making compounds 81 of Formulas I, II and IIa. As described herein, one may go through the process describing the transformation of intermediates 78 through 80 as shown to prepare compounds 81. Exemplary procedures thereto are provided in Examples 396-399. In addition, while compound 81 is shown as N-methyl-quinazoline attached to benzothiazole ring, the invention is not so limited, and other desired aryl and heteroaryl $R^1$ groups and Z and Z' fused rings may be used, including those exemplary compounds of Examples 398-399. Accordingly, scheme 17 is generally applicable to compounds of the present invention, as appreciated by those of ordinary skill in the art.

Scheme 18 (Method Q)

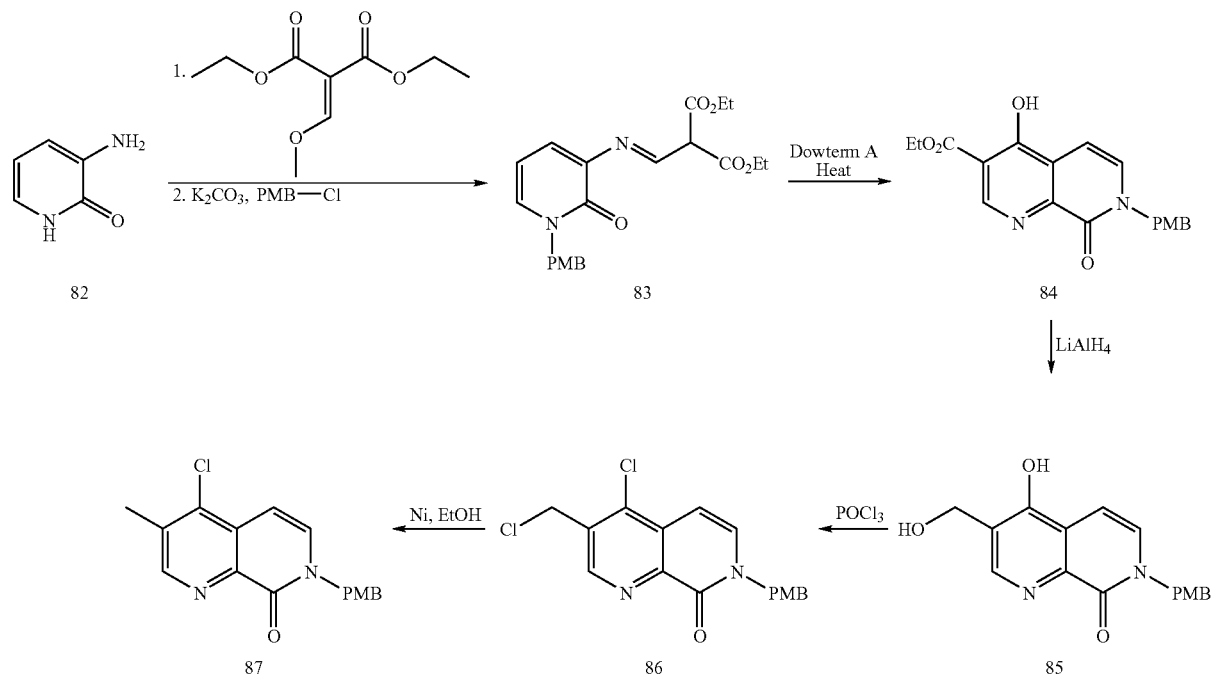

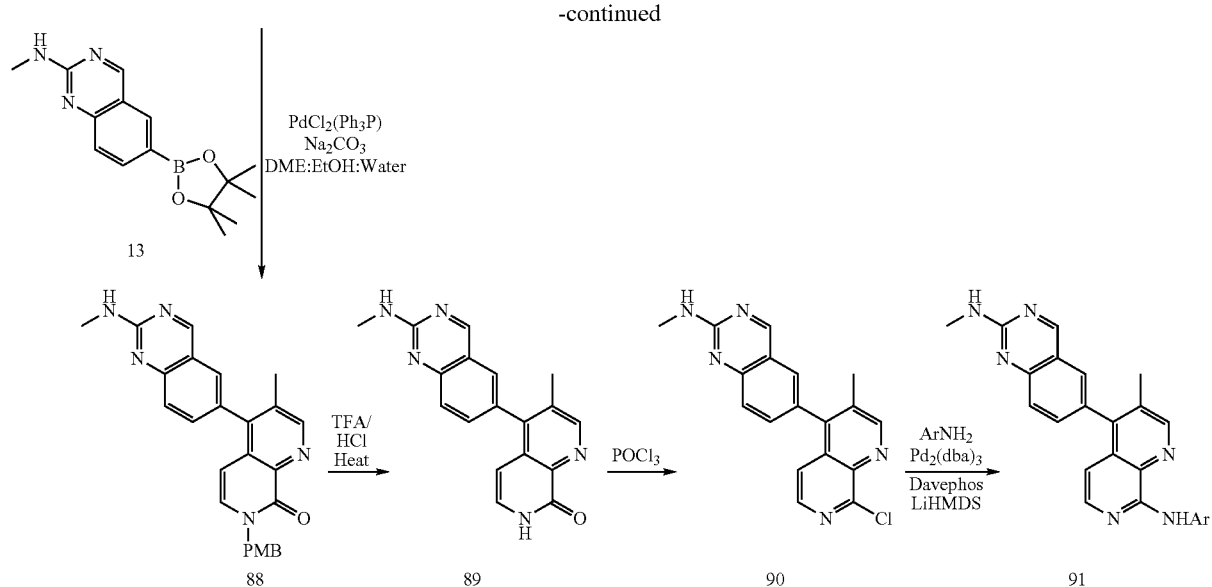

Scheme 18 illustrates an additional method for making compounds 91 of Formula I. As described herein, one may go through the process describing the transformation of intermediates 82 through 90 as shown to prepare compounds 91. Exemplary procedures thereto are provided in Examples 400-412. In addition, while compound 68 is shown as N-methylquinazoline attached to an isoquinoline, the invention is not so limited, and other desired aryl R1 groups and Z and Z' fused rings may be used, including those exemplary compounds of Examples 410-412. Accordingly, scheme 15 is generally applicable to compounds of the present invention, as appreciated by those of ordinary skill in the art.

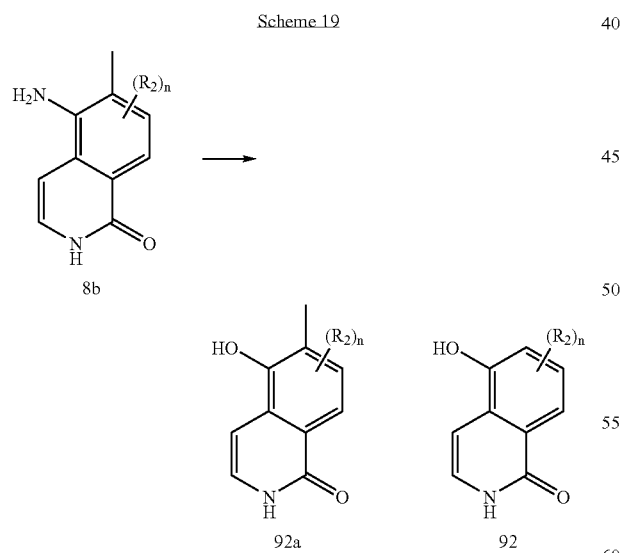

Scheme 19 illustrates an additional method for making intermediates 92. As described, 5-hydroxy-isoquinolone compounds 92 may be purchased and 5-hydroxy-6-methyl-isoquinolones compounds 92a may be made from 5-amino-6-methylisoquinolone compounds 8b by diazotization and hydrolysis. An exemplary procedures is provided in Example 413. Accordingly, scheme 19 is generally applicable to compounds of the present invention, as appreciated by those of ordinary skill in the art.

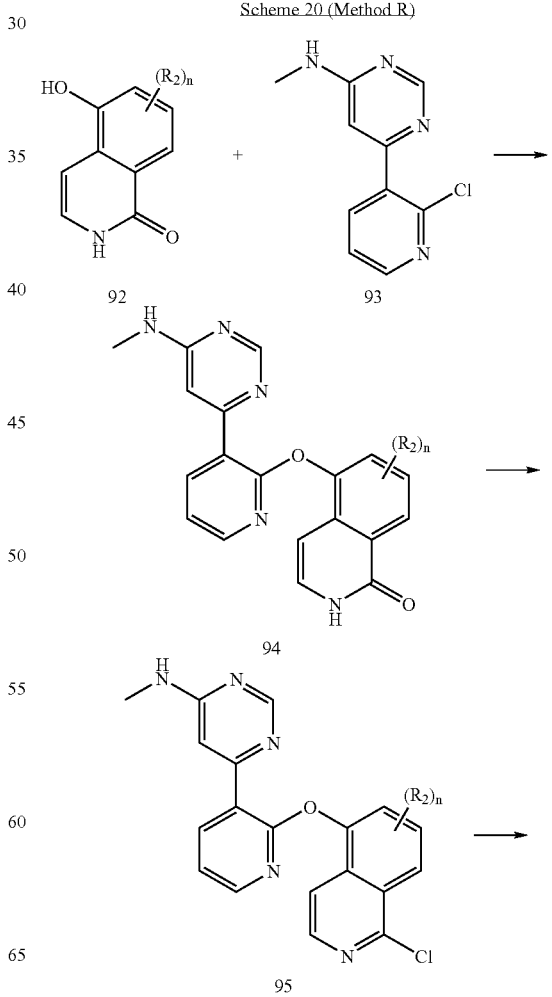

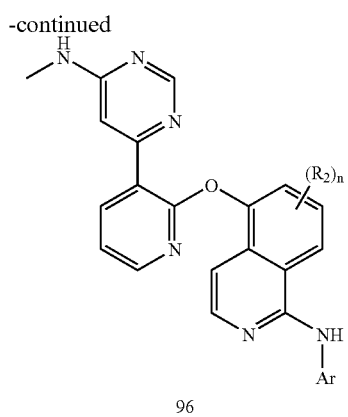

96

Scheme 20 illustrates an additional method for making compounds 96 of Formulas I, III and IIIa. As described herein, one may go through the process describing the transformation of intermediates 92 through 96 as shown to prepare compounds 96. Exemplary procedures thereto are provided in Examples 413-423. In addition, while compound 96 is shown as N-methyl-pyrimidine attached to a pyridyl-oxy moiety, the invention is not so limited, and other desired R1 groups and Z and Z' fused rings may be used, including those exemplary compounds of Examples 413, 415-423. Accordingly, scheme 20 is generally applicable to compounds of the present invention, as appreciated by those of ordinary skill in the art.

424-438. In addition, while compound 108 is shown as N-methyl-quinazoline attached to an isoquinoline, the invention is not so limited, and other desired aryl R1 groups and Z and Z' fused rings may be used, including those exemplary compounds of Examples 434-438. Accordingly, scheme 15 is generally applicable to compounds of the present invention, as appreciated by those of ordinary skill in the art.

While the above Schemes 1-21 describe methods of making compounds as shown, the strategy employed may be utilized to make compounds of Formulas I, II, IIa, III an IIIa, as appreciated by those of ordinary skill in the art. For example, while the schemes describe methods for making a pyrazole, pyridine or pyrimidine Z ring compound, the methods used amy also be applied to make other 5-membered and 6-membered heteroaryl Z rings, such as those described herein. It is appreciated and understood by persons of ordinary skill in the art that certain conditions will not be universal and may not be used to make every Z ring contemplated herein. Similarly, the methods teaching how to make the $R^1$ and $R^3$ groups above, may be applicable in making other $R^1$ and $R^3$ groups contemplated herein.

Further, while many compounds illustrated in schemes 1-21 show one $R^2$ group (methyl), similar compounds with no $R^2$ groups or compounds having more than one $R^2$ groups may also be made using similar methods.

The following analytical methods were used, unless otherwise noted, to identify the intermediates and compounds exemplified herein.

Analytical Methods:

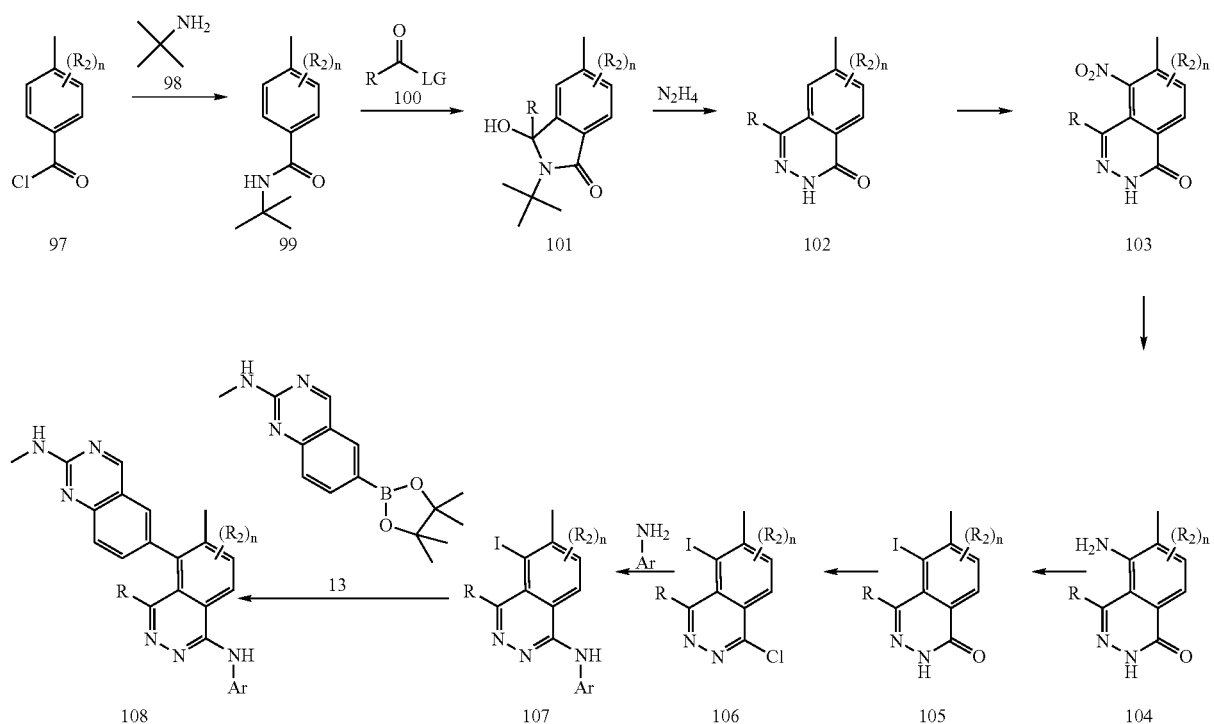

Scheme 21 (Method S)

Scheme 21 illustrates an additional method for making compounds 108 of Formula I and II. As described herein, one may go through the process describing the transformation of intermediates 97 through 107 as shown to prepare compounds 108. Exemplary procedures thereto are provided in Examples Unless otherwise indicated, all HPLC analyses were run on a Agilent Model 1100 system with an Agilent Technologies Zorbax SB-$C_8$ (5μ) reverse phase column (4.6×150 mm; Part no. 883975-906) run at 30° C. with a flow rate of about 1.50 mL/min. The mobile phase used solvent A ($H_2O$/0.1% TFA)

and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods:

(A) Using a 50×100 mm column (Waters, Exterra, C18, 5μ) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 min flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1H$ NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Various experimental methods have been employed to synthesize compounds of Formulas I, II, IIa, III and IIIa, as more generally described in Schemes 1-9 above, and further described in more detail by the representative examples 1-86 below. Table I following the written examples further described each example.

Example 1

Preparation of 6-methyl-5-nitroisoquinoline

Step 1

4-Methyl benzaldehyde (1641 ml, 13878 mmol) and 2,2-dimethoxyethanamine (1497 ml, 13878 mmol) were added to a 12 L round bottomed flask equipped with a mechanical stirrer, heating mantle, and Dean-Stark trap with condenser. (Note: The reaction exothermed with this addition immediately to 70° C.). The mixture was then gradually heated to 190° C. Water started to distill off vigorously around 105° C. The reaction was then azeotroped with toluene (400 mL). The Dean-Stark trap was replaced by a short path distillation apparatus to remove toluene more quickly. The crude product (2870 g, 100%) was used in the next step as is.

Step 2

The product from step 1 in a 12 L round bottomed flask equipped with a overhead stirrer and cooling condenser containing was treated with methanol (3.8 L). Sodium borohydride (511 g, 13.5 mol) was added in small portions (15 g at a time) whilst maintaining an internal reaction temperature between about 25-40° C. with an ice bath. After all of the sodium borohydride had been added, the reaction was stirred over night at RT. The reaction was quenched using saturated sodium bicarbonate solution (12 L) and washed with water (15 L), brine (11 L) and concentrated to give a yellow oil (2872 g, 100%).

Step 3

A portion of the product (yellow oil) from Step 2 (1001 g, 4783 mmol) was added to a 22 L round bottomed flask equipped with a mechanical stirrer and a nitrogen inlet. Triethylamine (798 mL, 5740 mmol) in dichloromethane (200 mL) was added and the mixture placed in an ice bath. p-Toluenesulfonyl chloride (912 g, 4783 mmol) was added in portions maintaining a temperature below 7° C. The reaction was then stirred at room temperature overnight. The reaction mixture was filtered through a fritted funnel to remove the bulk of the ammonium salts. The filtrate was transferred to a 50 L reactor and washed with water (2×10 L), 1 N NaOH solution (1×10 L), and brine (2×8 L), and concentrated. The residue was then treated with ether (12 L), stirred vigorously, and filtered through a fritted funnel to remove more salts. The filtrate was then concentrated to give the tosylate product (1738 g, 100%).

Step 4

Sulfuric acid (7699 mL, 144441 mmol) was added to a 10 L jacketed reactor at room temperature and stirred. Product from Step 3 (1500 g, 4127 mmol) was added portionwise maintaining the temperature between 20-32° C. When addition was complete, a small aliquot was removed every 15 min, diluted with saturated sodium bicarbonate, extracted with EtOAc and analyzed by HPLC. When reaction completion was confirmed, the reaction flask was cooled to −5° C. and potassium nitrate (1252 g, 12381 mmol) was added using a motorized solid addition funnel (10 rpm) adding at 100 g/h. After 850 g had been added, the remaining 400 g was added at a much higher rate (over 30 mins). The reaction was maintained below 5° C. The temperature was then raised to about 11° C. and progress monitored by HPLC. Completion was confirmed after 4 h. The reaction was then quenched by pumping over to a larger reactor (30 L) at 0° C. containing ice/water (15 L). The reaction was stirred over night at room temperature—a significant quantity of foam formed. The mixture was transferred to another vessel (20 L bottle) to be pumped over a large fine fritted funnel to remove the foamy material. The acidic solution was basified using 10 N NaOH (23 L) in 3 batches maintaining a temperature below 25° C. Each batch was extracted with DCM (7 L) and washed with brine (2 L) and water (7 L). The combined DCM extracts were dried over $MgSO_4$ and concentrated to give 6-methyl-5-nitroisoquinoline (328.4 g, 42%). MS (M+H)$^+$ 189.

Example 2

Preparation of 6-methyl-5-nitroisoquinoline-N-oxide

6-Methyl-5-nitroisoquinoline (100.0 g, 531 mmol) in Dichlormethane (1 L) was added to a 2 L 3-necked round bottomed flask and cooled to 5° C. Purified m-chloroperoxobenzoic acid (129 g, 749 mmol) was added to this stirred solution [m-CPBA was extracted with saturated Phosphate buffer pH 7.5 and DCM]. Initially with the addition of mCPBA the reaction exothermed, but then endothermed to 2° C. After 20 min, the contents in the flask solidified to a yellow/white solid and more DCM (300 mL) was added. The reaction was allowed to stir overnight at room temperature. DCM (2 L) was added and the mixture washed with 1 N NaOH (1 L), saturated sodium bicarbonate (1 L) and brine (1 L). The solution was dried over sodium sulfate and concentrated to give 6-methyl-5-nitroisoquinoline-N-oxide (81.7 g, 75%). MS (M+H)+ 205.

Example 3

Preparation of 1-chloro-6-methyl-5-nitroisoquinoline

6-Methyl-5-nitroisoquinolin-1(2H)-one-N-oxide (3.1 g, 15.2 mmol) was taken up in chloroform (100 mL) and phosphorus oxychloride (7 mL, 80 mmol) was added dropwise to the reaction. The mixture was then heated to 70° C. After 3 h, the reaction was cooled and the volatiles removed in vacuo. Residual phosphorus oxychloride was azeotroped with toluene. The residue was then dissolved in chloroform and washed with cold water, saturated NaHCO$_3$ and brine. The organic layer was then dried with sodium sulfate and purified by column chromatography using 10 to 40% ethyl acetate in hexanes as an eluent. The title compound was obtained an off-white solid (3.4 g, 96%). MS (M+H)+ 223.

Example 4

Preparation of 6-methyl-5-nitroisoquinolin-1(2H)-one 1-chloro-6-methyl-5-nitroisoquinoline (50 g, 225 mmol) was suspended in THF (500 mL, 10 mL/g) and treated with 5 N aq HCl (500 mL, 10 mL/g). The suspension was stirred vigorously in a 2 L Morton Flask under a reflux condenser and heated with a heating mantle to reflux overnight (14 h). The resulting suspension was allowed to cool to room temperature (22° C.). The solid was removed by suction filtration and the filtrate set aside. The solid was washed with water (100 mL), Et2O (2×100 mL) and hexane (100 mL), then air-dried to afford 40 g as a light yellow powder. The reserved filtrate was concentrated in vacuo to a volume of ~500 mL to afford a second crop of product. The second crop was washed with water (100 mL), Et2O (2×100 mL) and hexane (100 mL), then air-dried to afford 4 g as an orange powder. A total of 44 g (87% yield) of the title compound were isolated in this fashion. MS (M+H)+ 205.

Example 5

Preparation of 6-methyl-5-nitro-N-(3-(trifluoromethyl)phenyl)isoquinolin-1-amine 1-Chloro-6-methyl-5-nitroisoquinoline (0.25 g, 1.1 mmol) and 3-(trifluoromethyl)benzenamine (0.17 mL, 1.3 mmol) were added to a microwave tube containing 3 mL of isopropanol. The tube was capped and heated at 180° C. for 1500 seconds. The volatiles were removed in vacuo. The residue was taken up in DCM and washed with saturated NaHCO$_3$. The organic layer was dried with sodium sulfate and purified by column chromatography on silica gel using a gradient of 10 to 40% of ethyl acetate in hexanes to give the product as an orange solid (0.31 g, 79%). MS (M+H)+ 348.

Example 6

Preparation of 6-methyl-N$^1$-(3-(trifluoromethyl)phenyl)isoquinoline-1,5-diamine 6-Methyl-5-nitro-N-(3-(trifluoromethyl)phenyl)isoquinolin-1-amine (0.28 g, 0.81 mmol) was dissolved in ethanol (20 mL) and 10% palladium on carbon (0.086 g, 0.81 mmol) was added to the solution. The reaction stirred overnight at RT under a hydrogen atmosphere. The reaction was filtered through celite and concentrated to give the title compound as a pink film (0.25 g, 98%). MS (M+H)+ 318.

Example 7

Preparation of 6-methyl-N$^5$-(3-(pyrimidin-4-yl)pyridin-2-yl)-N$^1$-(3-(trifluoromethyl)phenyl)isoquinoline-1,5-diamine 6-Methyl-N$^1$-(3-(trifluoromethyl)phenyl)isoquinoline-1, 5-diamine (0.100 g, 0.30 mmol), 4-(2-chloropyridin-3-yl) pyrimidine (0.057 g, 0.30 mmol), dicyclohexylphosphino)-N,N-dimethylaminobiphenyl (0.0094 g, 0.024 mmol), and Pd$_2$(dba)$_3$ (0.010 g, 0.012 mmol) were all placed in a sealed tube containing 5 mL of anhydrous THF. Lithium bis (trimethylsilyl)amide (1.0 M in THF, 0.90 mL, 0.90 mmol) was then added to the mixture and nitrogen was bubbled into the reaction mixture for 5 min. The tube was capped and the reaction heated to 70° C. overnight. The reaction was allowed to cool to room temperature and quenched with methanol. The volatiles were removed in vacuo. The residue was taken up in ethyl acetate and washed (2×) with an aqueous saturated solution of sodium bicarbonate, then with water and then brine. The organic layer was then dried with sodium sulfate and the purified by column chromatography on silica gel using a gradient of 20 to 60% EtOAc in hexanes to give 6-methyl-N$^5$-(3-(pyrimidin-4-yl)pyridin-2-yl)-N$^1$-(3-(trifluoromethyl)phenyl)isoquinoline-1,5-diamine as a yellow solid (80 mg, 56%). MS (M+H)+ 473.

Examples 8-19

The compounds of Examples 8-19 (see Table I) were prepared in a manner analogous to Example 7, utilizing various substituted phenyl-amino-methyl-amino isoquinolines. These examples were synthesized using the general synthetic strategy described in Schemes 1 and 2 (Method A).

Example 20

Preparation of 5-amino-6-methylisoquinolin-1(2H)-one

A suspension of 6-methyl-5-nitroisoquinolin-1(2H)-one (40 g, 196 mmol) in glacial acetic acid (1 L) was purged with N$_2$. The suspension was treated with 10% Pd/C (10 g) and the reaction vessel was purged with H$_2$. The mixture was stirred at room temperature under H$_2$ (1 atm) until starting material consumed, approximately 100 h. The reaction mixture was purged with N$_2$, then filtered through a pad of Celite. The pad was washed with MeOH (400 mL) and the combined filtrate was treated with water (80 mL) and concentrated in vacuo to ~200 mL. The dark mixture was diluted with 200 mL MeOH and added in a thin stream to ice water (1.5 L) stirred in a large beaker. The resulting fine precipitate was collected by suction filtration. The greenish-grey powder was suspended in water (500 mL) and satd NaHCO₃ (100 mL) and sonicated for 1 min. The solid was collected by suction filtration, washed with water (2×100 mL), Et₂O (100 mL), and air-dried overnight to afford 28 g as a grey powder. The powder was dissolved in hot DMF (200 mL) and treated with decolorizing carbon (~10 g). The hot suspension was filtered through Celite. The filter cake was washed with MeOH (200 mL) and the filtrate was concentrated in vacuo to ~200 mL. The dark brown solution was added to water (1.2 L) to afford a fine crystalline precipitate. The solid was collected by suction filtration on a medium-sintered glass frit and washed with water (500 mL). A second crop precipitated in the filtrate and was collected by suction filtration, washed with water (100 mL) and added to the first crop. The combined material was washed with Et₂O (400 mL), and dried on the sintered glass funnel under a stream of N₂, with suction, for 16 h to afford 5-amino-6-methylisoquinolin-1(2H)-one (22 g, 64% yield) as a tan crystalline solid. MS (M+H)⁺ 175.

Example 21

Preparation of 5-iodo-6-methylisoquinolin-1(2H)-one

A 1-L flask equipped with a stir bar and containing concentrated hydrochloric acid (120 mL) was charged with 5-amino-6-methylisoquinolin-1(2H)-one (26 g, 149 mmol). Once a clear solution was obtained, the reaction mixture was cooled down to 0° C. and treated with a solution of sodium nitrite (15 g, 224 mmol) in 50 mL of water added dropwise. The reaction was stirred for 1 h and then KI (74 g, 448 mmol) dissolved in 150 mL of water was added carefully and slowly to the reaction. The mixture was stirred at 0° C. for 15 min and then heated to 65° C. and stirred for 1 h. The mixture was cooled down to RT and the solid that formed was collected by filtration. The solid was washed sequentially with water, a saturated aqueous solution of sodium thiosulfate (3×), water and cold MeOH, and finally ether. The brown solid was dried to give 5-iodo-6-methylisoquinolin-1(2H)-one (24 g, 56%). MS (M+H)⁺ 286.

Example 22

Preparation of 6-methyl-5-(2-(methylamino)quinazolin-6-yl)isoquinolin-1(2H)-one

N-Methyl-6-(4,4,5,5-tetramethyl-1,3,2-dioxaborolan-2-yl)quinazolin-2-amine (20 g, 69 mmol), 5-iodo-6-methylisoquinolin-1(2H)-one (16.50 g, 58 mmol), tetrakis(triphenylphosphine) palladium(0) (6.7 g, 5.8 mmol) and 2.0 M aqueous sodium carbonate (58 mL, 116 mmol) were equally divided and placed into 11 clear microwave vials along with 10 mL of dioxane in each. The vials were capped and each heated in a Personal Chemistry Smith Synthesizer at 150° C. for 10 min. The reaction mixtures were combined and diluted with EtOAc. The solid that precipitated out was collected by filtration and suspended with stirring in hot MeOH for 1 h. The solid was filtered to give 10 g of a light brown solid. The ethyl acetate layer and the MeOH were combined and loaded onto silica and then purified by column chromatography using a gradient of 2 to 10% MeOH in DCM to give an additional 3 g of product. The 2 batches were combined to give 6-methyl-5-(2-(methylamino)quinazolin-6-yl)isoquinolin-1(2H)-one (13 g, 71%) as a light brown solid. MS (M+H)⁺ 317.

Example 23

Preparation of 6-(1-chloro-6-methylisoquinolin-5-yl)-N-methylquinazolin-2-amine

6-Methyl-5-(2-(methylamino)quinazolin-6-yl)isoquinolin-1(2H)-one (13.00 g, 41.1 mmol) was treated with POCl₃ (57.5 mL, 616 mmol) and the mixture heated to 100° C. while stirring. After 4 h, the volatiles were removed under vacuum and residual POCl₃ was removed by azeotroping with toluene. Crushed ice was added to the residue and the mixture was stirred for 1 h. The resulting free flowing solid was washed with water and and saturated sodium bicarbonate, filtered off and dissolved in a 9:1 mixture of DCM and MeOH. The solution was loaded onto silica gel and purified by column chromatography using a gradient of 2 to 10% MeOH in DCM to give 6-(1-chloro-6-methylisoquinolin-5-yl)-N-methylquinazolin-2-amine (9.34 g, 68%) as a yellow foam. MS (M+H)⁺ 335.

Example 24

Preparation of N-methyl-6-(6-methyl-1-(3-(trifluoromethyl) phenylamino)isoquinolin-5-yl)quinazolin-2-amine 6-(1-Chloro-6-methylisoquinolin-5-yl)-N-methylquinazolin-2-amine (8.50 g, 25.4 mmol), 3-(trifluoromethyl)benzenamine (4.30 g, 26.7 mmol), Davephos (0.40 g, 1.02 mmol) and tris(dibenzylideneacetone)dipalladium (0) (0.465 g, 0.508 mmol) were equally divided into 6 and added to 6 clear microwave vials along with 10 mL of dioxane in each vial. Nitrogen was bubbled into each vial for 10 min and lithium bis(trimethylsilyl)amide (1.0 M in THF) (50.8 mL, 50.8 mmol) divided into 6 (8.46 mL each) was added to the vials. The vials were then capped and heated to 150° C. in a Personal Chemistry Smith Synthesizer for 10 min. The reaction mixtures were combined and diluted with ethyl acetate. The organic layer was washed (2×) with an aqueous saturated solution of sodium bicarbonate, then with water and then brine. The organic layer was then dried with sodium sulfate and purified by column chromatography on silica gel using a gradient of 20 to 100% EtOAc in hexanes and recrystallization from 3:1 ether/ethyl acetate to give N-methyl-6-(6-methyl-1-(3-(trifluoromethyl)phenylamino)isoquinolin-5-yl) quinazolin-2-amine (6.0 g, 51%) as a white solid. MS (M+H)⁺ 460.

Examples 25-41

The compounds of Examples 25-41 (see Table I) were prepared in a manner analogous to Example 24, utilizing various substituted phenyl-amino-methyl-amino isoquinolines A-B rings with a quinazoline C-D ring. These examples were synthesized using the general synthetic strategy described in schemes 1 and 3 (Method B).

Example 42

Preparation of 3-acetamido-4-methyl-2-nitrobenzoic acid

3-Acetamido-4-methylbenzoic acid (205 g, 1061 mmol) was added portionwise over 45 min to stirred fuming nitric acid (1 L) at −5° C., maintaining a reaction temperature below 0° C. The mixture was stirred for an additional 1 h and then crushed ice (2.5 kg) was added. The mixture was stirred for a further 30 min. The precipitate that formed was filtered off and thoroughly washed with water. The resulting cake was air dried and suspended in 1 L of acetic acid at 65° C. The suspension was stirred for 1 hour, allowed to cool down to RT and then filtered. The filtrate was washed with acetic acid and ether to give 3-acetamido-4-methyl-2-nitrobenzoic acid (160 g, 63%) as a white solid. MS (M+H)$^+$ 239.

Example 43

Preparation of 3-amino-4-methyl-2-nitrobenzoic acid

3-Acetamido-4-methyl-2-nitrobenzoic acid (65 g, 273 mmol) was taken in dioxane (350 mL) and treated with 5 N aqueous HCl (150 mL). The reaction was stirred at 80° C. for 16 h. The dioxane was removed under reduced pressure and the residue poured onto crushed ice. The resulting precipitate was filtered off. The filtrate was extracted with ethyl acetate (2×). The organic layer and the solid were combined and concentrated under vacuum to give 3-amino-4-methyl-2-nitrobenzoic acid (45 g, 84% yield) as a yellow solid. MS (M+H)$^+$ 197.

Example 44

Preparation of 3-iodo-4-methyl-2-nitrobenzoic acid

3-Amino-4-methyl-2-nitrobenzoic acid (13 g, 66 mmol) was taken up in 50 mL of DMSO and 30% aqueous sulfuric acid (150 mL) was added. The mixture was cooled to 0° C. and sodium nitrite (7 g, 99 mmol) dissolved in 20 mL of water was added slowly. The mixture was stirred for 1 h and potassium iodide (28 g, 166 mmol) dissolved in 50 mL of water was added. The mixture was allowed to stir at RT for 1 h. The mixture was extracted with ethyl acetate and the organic layer washed with an aqueous solution of 2 M sodium sulfite, water and brine. The organic layer was dried with sodium sulfate and concentrated under vacuum to give 3-iodo-4-methyl-2-nitrobenzoic acid (17 g, 84%) as a light brown solid. MS (M+H)$^+$ 308.

Example 45

Preparation of 2-amino-3-iodo-4-methylbenzoic acid

3-Iodo-4-methyl-2-nitrobenzoic acid (46.00 g, 150 mmol) was suspended in ethanol (500 mL) and acetic acid (86 mL, 1498 mmol). The mixture was heated to 70° C. and iron (33 g, 599 mmol) was added in small portions. Stirring was continued for 3 h, and then the reaction was cooled down to RT and poured on 1.5 kg of crushed ice and 1 L of 5 N aqueous HCl. The mixture was extracted with ethyl acetate and the organic layer was dried with sodium sulfate, concentrated under vacuum and dried to give 2-amino-3-iodo-4-methylbenzoic acid (40 g, 96%) as a tan solid. MS (M+H)$^+$ 278

Example 46

Preparation of 8-iodo-7-methylquinazolin-4(3H)-one

2-Amino-3-iodo-4-methylbenzoic acid (8.00 g, 29 mmol), formamide (11 mL, 289 mmol) and NMP (11 ml) were added to an 80 mL microwave vessel. The mixture was heated for 15 min at 210° C. The mixture was diluted with ice water and the precipitated solid collected by filtration. The solid was washed with water and dried to give 8-iodo-7-methylquinazolin-4(3H)-one (7.3 g, 88%) as a light brown solid. MS (M+H)$^+$ 287.

Example 47

Preparation of 4-chloro-8-iodo-7-methylquinazoline

Phosphorous oxychloride (19.5 mL, 210 mmol) and 8-iodo-7-methylquinazolin-4(3H)-one (2.00 g, 6.99 mmol) were added to a round bottomed flask. The reaction mixture was heated at reflux for 2 h. Upon cooling, excess POCl$_3$ was removed under reduced pressure and the remaining crude product dissolved in DCM (100 mL) and washed with ice-cold water (300 mL) to remove excess acid. The crude residue dissolved in DCM was then dried over anhydrous sodium sulfate and concentrated in vacuo to give 4-chloro-8-iodo-7-methylquinazoline (1.96 g, 92%) as an amorphous brown solid. MS (M+H)$^+$ 305.

Example 48

Preparation of N-(2,3-dihydro-1H-inden-5-yl)-8-iodo-7-methylquinazolin-4-amine hydrochloride 2,3-Dihydro-1H-inden-5-amine (109 mg, 821 μmol), 4-chloro-8-iodo-7-methylquinazoline (250 mg, 821 μmol) and IPA (5 mL) were added to microwave-vial. The reaction mixture was heated at 110° C. for 10 min. A precipitate formed upon cooling. The crude product was diluted with EtOAc (20 mL), filtered, washed twice with EtOAc (20 mL) and air-dried to give N-(2,3-dihydro-1H-inden-5-yl)-8-iodo-7-methylquinazolin-4-amine hydrochloride (311 mg, 87%) as an amorphous off-white solid. MS (M+H)$^+$ 402.

Example 49

Preparation of 6-(4-(2,3-dihydro-1H-inden-5-ylamino)-7-methylquinazolin-8-yl)-N-methylquinazolin-2-amine 2 M Aqueous sodium carbonate (857 μl, 1.7 mmol), tetrakis (triphenylphosphine)palladium (0) (99 mg, 86 μmol), N-(2,3-dihydro-1H-inden-5-yl)-8-iodo-7-methylquinazolin-4-amine hydrochloride (250 mg, 571 μmol), N-methyl-6-(4,4,5,5-tetramethyl-1,3,2-dioxaborolan-2-yl)quinazolin-2-amine (326 mg, 1142 μmol) and dioxane (5 mL) were added to a microwave vial. The reaction mixture was heated in a microwave at 180° C. for 20 min. The solid residue was filtered off through Celite® and washed with methanol and DCM. The filtrate was concentrated and purified by flash chromatography (0-10% MeOH in DCM) to give 6-(4-(2,3-dihydro-1H-inden-5-ylamino)-7-methylquinazolin-8-yl)-N-methylquinazolin-2-amine as an off-white amorphous solid. MS (M+H)$^+$ 433.

Examples 50-58

The compounds of Examples 50-58 (see Table I) were prepared in a manner analogous to Example 49, utilizing various substituted phenyl-amino-methyl-amino quinazoline A-B rings with a quinazoline C-D ring. These examples were synthesized using the general synthetic strategy described in Scheme 4 (Method C).

Example 59

Preparation of 2-fluoro-4-methylbenzonitrile

A mixture of 1-bromo-2-fluoro-4-methylbenzene (70 g, 370 mmol) and CuCN (50 g, 555 mmol) in DMF (300 mL) was heated at reflux for 24 h. After cooling to RT, concentrated aqueous ammonia (300 mL) and diethyl ether (200 mL) were added and the mixture stirred for 1 h. The mixture was extracted with diethyl ether (3×200 mL). The combined organic layers were washed with brine (3×200 mL) and dried over sodium sulfate. Solvent was removed in vacuo to give the product (44 g, 88%) as pale yellow solid. MS (M+H)$^+$ 136.

Example 60

Preparation of 2-fluoro-3-iodo-4-methylbenzonitrile

A solution of 2,2,6,6,-tetramethylpiperidine (45 mL, 267 mmol) in THF (400 mL) was cooled below −80° C. under $N_2$-atmosphere. n-Butyl lithium (2.5M in hexane, 110 mL, 275 mmol) was added slowly maintaining the temperature of the mixture below −70° C. After complete addition, the reaction mixture was warmed to −50° C. and stirred at this temperature for 30 minutes. The clear solution became turbid indicating the salt formation. It was cooled to −80° C. again and a solution of 2-fluoro-4-methylbenzonitrile (32.4 g, 240 mmol) in THF (150 mL) was slowly added taking care that the temperature of the reaction mixture remained below −70° C. It was then warmed up to −50° C. and stirred for 30 minutes. The mixture was then cooled to −70° C. and a saturated solution of $I_2$ (67 g, 264 mmol) in THF was added slowly maintaining the temperature at −70° C. After complete addition, the mixture was warmed to ambient temperature. It was added to a solution of $Na_2S_2O_3$ (160 g in 1.5 L of water) and stirred for an hour. The organic part was separated and the aqueous layer was extracted with EtOAc. The organic layers were combined and washed with brine. The organic layer was then dried over $Na_2SO_4$ and filtered. The volatiles were evaporated under reduced pressure. The crude product was subjected to vacuum distillation; at about 60° C., excess TMP was removed, at about 100° C., the starting compound 2-fluoro-4-methylbenzonitrile and a small amount of product was removed and, finally at 115° C., pure 2-fluoro-3-iodo-4-methylbenzonitrile was obtained (30 g, 48% yield). MS (M+H)$^+$ 262.

Example 61

Preparation of 7-iodo-1,6-dimethyl-1H-indazol-3-amine

A mixture of 2-fluoro-3-iodo-4-methylbenzonitrile (10.4 g, 38.3 mmol) and 1-methyl hydrazine (10 mL, 187 mmol) was stirred at 80° C. for 16 h. Excess of hydrazine was evaporated under reduced pressure. The residue was washed with saturated $NaHCO_3$ solution and extracted with EtOAc. The organic layer was washed with water followed by brine and dried using $Na_2SO_4$. The solvent was evaporated after filtration to obtain a white product (9.2 g, 83% crude yield) which contained 77% of 7-iodo-1,6-dimethyl-1H-indazol-3-amine and 23% of isomer 7-iodo-2,6-dimethyl-2H-indazol-3-amine. 5 g of this mixture was subjected to column chromatography using silica (ISCO) and EtOAc/heptane (20% to 50%) mixture. 2.6 g of pure 7-iodo-1,6-dimethyl-1H-indazol-3-amine (43% yield). MS (M+H)+ 288. Remaining 4 g mixture was washed with $CH_2Cl_2$. Residue contained pure 7-iodo-2,6-dimethyl-2H-indazol-3-amine (1.0 g,). MS (M+H)$^+$ 288.

Example 62

Preparation of 6-(3-amino-1,6-dimethyl-1H-indazol-7-yl)-N-methylquinazolin-2-amine A mixture of 7-iodo-1,6-dimethyl-1H-indazol-3-amine (266 mg, 927 μmol), N-methyl-6-(4,4,5,5-tetramethyl-1,3,2-dioxaborolan-2-yl)quinazolin-2-amine (317 mg, 1112 μmol), sodium carbonate (2 M aqueous) (927 μl, 1853 μmol) and tetrakis(triphenylphosphine)palladium (0) (54 mg, 46 μmol) in dioxane (4 mL) was purged with nitrogen in a sealed microwave vial. The mixture was heated in a microwave reactor at 150° C. for 33 min. Solvent was removed in vacuo and the residue was purified by flash chromatography (1-5% MeOH/DCM) to give the title compound (230 mg, 78%). MS (M+H)$^+$ 319.

Example 63

Preparation of 6-(1,6-dimethyl-3-(3-(trifluoromethyl)phenylamino)-1H-indazol-7-yl)-N-methylquinazolin-2-amine A mixture of 1-bromo-3-(trifluoromethyl)benzene (19 μL, 138 μmol), tris(dibenzylideneacetone)dipalladium (0) (3.5 mg, 3.8 μmol), sodium t-butoxide (17 mg, 176 μmol), 6-(3-amino-1,6-dimethyl-1H-indazol-7-yl)-N-methylquinazolin-2-amine (40 mg, 126 μmol) and X-Phos (6.7 mg, 14 μmol) in toluene (3 mL) was purged with nitrogen and heated in a microwave reactor at 130° C. for 33 min. Solvent was removed in vacuo and the residue was purified by flash chromatography (25-50% EtOAc hexane) to give the title compound. MS (M+H)$^+$ 463.

Examples 64-65

The compounds of Examples 64-65 (see Table I) were prepared in a manner analogous to Example 63, utilizing various substituted phenyl-amino-methyl-indazolyl A-B rings with a quinazoline C-D ring. These examples were synthesized using the general synthetic strategy described in Scheme 5 (Method D).

Example 66

Preparation of 6-methyl-5-(3-(6-(methylamino)pyrimidin-4-yl)pyridin-2-ylamino)isoquinolin-1(2H)-one 6-(2-chloropyridin-3-yl)-N-methylpyrimidin-4-amine (897 mg, 4.1 mmol), 5-amino-6-methylisoquinolin-1(2H)-one (779 mg, 4.5 mmol), 2-dicyclohexylphosphino-2'-(N,N-dimethylamino) biphenyl (128 mg, 0.33 mmol) and tris (dibenzylideneacetone) dipalladium (0) (149 mg, 0.16 mmol) were added to a microwave tube. The tube was capped and flushed with nitrogen, and then lithium bis(trimethylsilyl) amide (16.9 mL, 1.0 M solution in THF) was added. The mixture was heated in a microwave reactor at 150° C. for 15 min. The reaction mixture was quenched with saturated aqueous sodium bicarbonate then extracted with DCM. The DCM extracts were concentrated and purified by flash chromatography (0-10% 2 M ammonia in methanol) to give the title compound (380 mg, 26%). MS (M+H)$^+$ 359.

Example 67

Preparation of 1-chloro-6-methyl-N-(3-(6-(methylamino)pyrimidin-4-yl)pyridin-2-yl)isoquinolin-5-amine 6-Methyl-5-(3-(6-(methylamino)pyrimidin-4-yl)pyridin-2-ylamino)isoquinolin-1(2H)-one (195 mg, 0.54 mmol) was suspended in $POCl_3$ (10 mL) and heated at 120° C. for 3 h. $POCl_3$ was removed in vacuo and the residue was washed with toluene three times. The residue was added to water and the resulting solid collected by filtration, washing with saturated aqueous sodium bicarbonate and water. The resulting title compound was dried in vacuo. MS $(M+H)^+$ 377.

Example 68

Preparation of 6-methyl-$N^5$-(3-(6-(methylamino)pyrimidin-4-yl)pyridin-2-yl)-$N^1$-(3-(trifluoromethoxy)phenyl)isoquinoline-1,5-diamine 3-(Trifluoromethoxy)aniline (13 µL, 96 µmol), 1-chloro-6-methyl-N-(3-(6-(methylamino)pyrimidin-4-yl)pyridin-2-yl)isoquinolin-5-amine (33 mg, 88 µmol), tris (dibenzylideneacetone)dipalladium (0) (3 mg, 4 µmol), and 2-dicyclohexylphosphino-2'-(N,N-dimethylamino)biphenyl (3 mg, 7 µmol) were added to a microwave tube and suspended in THF-DMF (1:1, 1 mL). The tube was flushed with nitrogen and a solution of lithium bis(trimethylsilyl)amide, 1.0 M in hexanes (385 µL, 385 µmol) was added. The tube was heated in a microwave reactor at 150° C. for 15 min. The reaction mixture was partitioned between DCM and saturated aqueous sodium bicarbonate. The DCM layer was washed with brine, dried over sodium sulfate and concentrated. The residue was purified via preparative TLC on silica (DCM:EtOAc:EtOH:TEA=5:5:10:10) to give the desired product as a yellow solid. MS $(M+H)^+$ 518.

Examples 69-73

The compounds of Examples 69-73 (see Table I) were prepared in a manner analogous to Example 68, utilizing various substituted phenyl-amino-methyl-isoquinoline A-B rings with a pyrimidyl-pyridine C-D ring. These examples were synthesized using the general synthetic strategy described in Scheme 9 (Method E).

Example 74

Preparation of 2-fluoro-3-iodo-4-methylbenzoic acid

2-Amino-3-iodo-4-methylbenzoic acid (3.9 g, 14 mmol) was added slowly at 0° C. to HF-pyridine (30 mL). The mixture was stirred for 15 min and then sodium nitrite (1.5 g, 21 mmol) was added slowly at 0° C. The resulting mixture was stirred at 0° C. for 15 min and warmed up to RT for 15 min, then heated at 90° C. for 1.5 h. The mixture was cooled to 50° C., ice-water (100 mL) was added and the mixture was extracted with EtOAc (3×80 mL). The combined organic extracts were washed with brine (100 mL) and dried over sodium sulfate. The solvent was removed in vacuo to give the title compound (3.5 g, 89%). MS $(M+H)^+$ 281.

Example 75

Preparation of 2-fluoro-3-iodo-N-(3-isopropoxyphenyl)-4-methylbenzamide

Oxalyl chloride (2 M in DCM) (1832 µl, 3664 µmol) was added to a suspension of 2-fluoro-3-iodo-4-methylbenzoic acid (684 mg, 2443 µmol) in DCM (20 mL) at 0° C. One drop of DMF (cat) was added. The mixture was stirred at RT for 3 h. Solvent was removed under vacuum. DCM (5 mL) was added to the residue and the mixture was added slowly to a mixture of 3-isopropoxybenzenamine (540 µL, 3664 µmol) and triethylamine (681 µL, 4885 µmol) in DCM (10 mL) at 0° C. The mixture was stirred at RT overnight and then water (50 mL) was added. The mixture was extracted with DCM (3×50 mL). The combined organic layers were washed with brine (100 mL) and dried over sodium sulfate. The solvent was removed in vacuo and the residue was purified by preparative TLC eluting with 10% EtOAc/hexane to give the title compound (683 mg, 68%). MS $(M+H)^+$ 414.

Example 76

Preparation of 2-fluoro-N-(3-isopropoxyphenyl)-4-methyl-3-(2-(methylamino)-quinazolin-6-yl)benzamide A mixture of 2-fluoro-3-iodo-N-(3-isopropoxyphenyl)-4-methylbenzamide (630 mg, 1525 µmol), N-methyl-6-(4,4,5,5-tetramethyl-1,3,2-dioxaborolan-2-yl)quinazolin-2-amine (522 mg, 1830 µmol) and sodium carbonate (2 M aqueous solution) (1525 µL, 3049 µmol) in DME (25 mL) was flushed with nitrogen and then tetrakis(triphenylphosphine)palladium (0) (176 mg, 152 µmol) was added. The mixture was refluxed for 24 h and then cooled to RT. Solvent was removed in vacuo and the residue was purified by flash chromatography eluting with EtOAc/hexane (25-60%) to give the title compound (387 mg, 57%). MS $(M+H)^+$ 445.

Example 77

Preparation of 2-fluoro-N-(3-isopropoxyphenyl)-4-methyl-3-(2-(methylamino)-quinazolin-6-yl)benzothioamide A mixture of Lawesson's reagent (47 mg, 115 µmol) and 2-fluoro-N-(3-isopropoxyphenyl)-4-methyl-3-(2-(methylamino)quinazolin-6-yl)benzamide (93 mg, 209 µmol) in toluene (8 mL) was heated at reflux for 16 h. Solvent was removed in vacuo and the residue was purified by flash chromatography (25-70% EtOAc/hexane) to give the title compound. MS $(M+H)^+$ 461.

Example 78

Preparation of 6-(3-(3-isopropoxyphenylamino)-6-methyl-1H-indazol-7-yl)-N-methylquinazolin-2-amine A mixture of 2-fluoro-N-(3-isopropoxyphenyl)-4-methyl-3-(2-(methylamino)quinazolin-6-yl)benzothioamide (54 mg, 117 µmol) and hydrazine hydrate (11 µL, 234 µmol) in n-butanol (6 mL) was heated in a microwave reactor at 150° C. for 33 min. Solvent was removed and the residue was purified by preparative TLC (50% EtOAc/hexane) to give the title compound. MS $(M+H)^+$ 439.

Example 79

Preparation of 6-(1-(3,3-dimethylindolin-6-ylamino)-6-methylisoquinolin-5-yl)-N-methylquinazolin-2-amine 1-(3,3-Dimethyl-6-(6-methyl-5-(2-(methylamino)quinazolin-6-yl)isoquinolin-1-ylamino)indolin-1-yl)ethanone (180 mg, 0.36 mmol) was dissolved in 5 mL of EtOH and treated with 2 mL of concentrated aqueous HCl. The mixture was heated to 50° C. for 6 h. The mixture was concentrated and the residue was taken up in DCM and neutralized with 2 M ammonia in MeOH. The solution was pre-adsorbed onto silica gel and purified by column chromatography on silica gel using a gradient of 3 to 12% of MeOH in DCM. The clean fraction were concentrated under vacuum and the residue triturated with 1:1 diethyl ether/hexane to give 120 mg of 6-(1-(3,3-dimethylindolin-6-ylamino)-6-methylisoquinolin-5-yl)-N-methylquinazolin-2-amine as a pale yellow solid. MS (M+H)$^+$ 461.

Examples 80-81

The compounds of Examples 80-81 (see Table I) were prepared in a manner analogous to Example 79. These examples were synthesized using the general synthetic strategy described in Scheme 7 (Method G).

Example 82

Preparation of 8-iodo-2,7-dimethyl-4H-benzo[d][1,3]oxazin-4-one

2-Amino-3-iodo-4-methylbenzoic acid (10 g, 36 mmol) was treated with acetic anhydride (70 mL) and the mixture stirred at reflux for 4 h. The reaction was allowed to cool down to RT and placed in an ice bath for ~2 h. The resulting precipitate was collected by filtration, washed with diethyl ether and dried to give 8-iodo-2,7-dimethyl-4H-benzo[d][1,3]oxazin-4-one (8.9 g, 82%) as a tan solid. MS (M+H)$^+$ 302.

Example 83

Preparation of 8-iodo-2,7-dimethylquinazolin-4(3H)-one

Anhydrous ammonia (50 mL) was condensed in a 500 mL 3 necked flasked containing 8-iodo-2,7-dimethyl-4H-benzo[d][1,3]oxazin-4-one (8.5 g, 28 mmol) cooled to −78° C., and the reaction was stirred for 3 h. The cooling bath was removed and the solvent was allowed to evaporate at RT. 1 N Sodium hydroxide (100 mL) was added to the reaction and stirred at reflux for 1 h. The reaction was cooled down to 0° C. and acidified to pH 3 with 5 N HCl. The resulting precipitate was collected by filtration, washed with water and dried in a vacuum oven at 60° C. overnight. 8-Iodo-2,7-dimethylquinazolin-4(3H)-one (8 g, 94% yield) was obtained as a white solid. MS (M+H)$^+$ 301.

Example 84

Preparation of 4-chloro-8-iodo-2,7-dimethylquinazoline

8-Iodo-2,7-dimethylquinazolin-4(3H)-one (0.300 g, 1.00 mmol) was treated with phosphorus oxychloride (10 mL, 107 mmol) and the mixture stirred at 120° C. for 4 h. During this time, the reaction went from being a milky white suspension to a clear solution. The mixture was concentrated under vacuum and the residual phosphorous oxychloride was azeotroped with toluene. The residue was taken up in DCM and washed with cold water (2×) followed by washes (2×) with aqueous saturated sodium bicarbonate and brine. The organic solution was then dried with sodium sulfate and concentrated under vacuum to give 4-chloro-8-iodo-2,7-dimethylquinazoline (0.30 g, 94%) as an orange solid. MS (M+H)$^+$ 319.

Example 85

Preparation of 8-iodo-2,7-dimethyl-N-(3-(trifluoromethoxy)phenyl)quinazolin-4-amine 4-Chloro-8-iodo-2,7-dimethylquinazoline (0.30 g, 0.94 mmol) and 3-(trifluoromethoxy)benzenamine (0.20 g, 1.1 mmol) were placed in a microwave vial containing 3 mL of IPA. The vial was capped and heated in a microwave reactor at 170° C. for 10 min. The mixture was concentrated in vacuo and the residue was taken up in ethyl acetate and washed (2×) with an aqueous saturated solution of sodium bicarbonate, then with water and then brine. The organic layer was dried with sodium sulfate, concentrated and purified by column chromatography on silica gel using a gradient of 20 to 60% EtOAc in hexanes to give a 8-iodo-2,7-dimethyl-N-(3-(trifluoromethoxy)phenyl)quinazolin-4-amine (0.32 g, 74%) as an off-white solid. MS (M+H)$^+$ 460.

Example 86

Preparation of 6-(2,7-dimethyl-4-(3-(trifluoromethoxy)phenylamino)quinazolin-8-yl)-N-methylquinazolin-2-amine 8-Iodo-2,7-dimethyl-N-(3-(trifluoromethoxy)phenyl) quinazolin-4-amine (0.250 g, 0.544 mmol), N-methyl-6-(4,4,5,5-tetramethyl-1,3,2-dioxaborolan-2-yl)quinazolin-2-amine (0.186 g, 0.653 mmol), tetrakis(triphenylphosphine) palladium(0) (0.0629 g, 0.0544 mmol) and 2 M aqueous sodium carbonate (0.544 mL, 1.09 mmol) were placed in a microwave vial and dioxane (3 mL) was added. The tube was capped and heated in a microwave reactor at 150° C. for 10 min. The mixture was concentrated in vacuo and the residue dissolved in ethyl acetate and washed (2×) with an aqueous saturated solution of sodium bicarbonate, then with water and then brine. The organic layer was dried with sodium sulfate and then purified by column chromatography on silica gel using a gradient of 20 to 80% EtOAc in hexanes. The clean fractions were combined and concentrated under vacuum to give a yellow film. The film was triturated with a 1:1 mixture of ether and hexanes. This resulted in the formation of an off-white solid which was collected by filtration and dried in a vacuum oven to give 6-(2,7-dimethyl-4-(3-(trifluoro-methoxy)phenylamino)quinazolin-8-yl)-N-methylquinazolin-2-amine (0.212 g, 79%). MS (M+H)$^+$ 491.

Table I further describes the representative compounds exemplified above.

TABLE I

| Ex. No. | Synth. Method | Structure ACD Name | MS (M + H)$^+$ |
|---|---|---|---|
| 7 | A | 6-methyl-N$^5$-(3-(4-pyrimidinyl)-2-pyridinyl)-N$^1$-(3-(trifluoromethyl)phenyl)-1,5-isoquinolinediamine | 473.2 |
| 8 | A | N$^1$-(3-(methyloxy)-5-(trifluoromethyl)phenyl)-N$^5$-(3-(4-pyrimidinyl)-2-pyridinyl)-1,5-isoquinolinediamine | 489.2 |
| 9 | A | 6-methyl-N$^1$-phenyl-N$^5$-(3-(4-pyrimidinyl)-2-pyridinyl)-1,5-isoquinolinediamine | 405.2 |

TABLE I-continued

| Ex. No. | Synth. Method | Structure ACD Name | MS (M + H)+ |
|---|---|---|---|
| 10 | A | N1-(3-(1,1-dimethylethyl)phenyl)-6-methyl-N5-(3-(4-pyrimidinyl)-2-pyridinyl)-1,5-isoquinolinediamine | 461.2 |
| 11 | A | N1-(3-(dimethylamino)phenyl)-6-methyl-N5-(3-(4-pyrimidinyl)-2-pyridinyl)-1,5-isoquinolinediamine | 448.2 |
| 12 | A | 6-methyl-N1-(3-(1-methylethyl)phenyl)-N5-(3-(4-pyrimidinyl)-2-pyridinyl)-1,5-isoquinolinediamine | 447.2 |
| 13 | A | 6-methyl-N1-(3-((1-methylethyl)oxy)phenyl)-N5-(3-(4-pyrimidinyl)-2-pyridinyl)-1,5-isoquinolinediamine | 463.2 |
| 14 | A | N1-(3-chlorophenyl)-6-methyl-N5-(3-(4-pyrimidinyl)-2-pyridinyl)-1,5-isoquinolinediamine | 439.1 |
| 15 | A | N1-(3-(1,1-dimethylethyl)-1-methyl-1H-pyrazol-5-yl)-6-methyl-N5-(3-(4-pyrimidinyl)-2-pyridinyl)-1,5-isoquinolinediamine | 465.2 |
| 16 | A | N1-(4-(1,1-dimethylethyl) phenyl)-6-methyl-N5-(3-(4-pyrimidinyl)-2-pyridinyl)-1,5-isoquinolinediamine | 461.2 |
| 17 | A | N1-6-dimethyl-N5-(3-(4-pyrimidinyl)-2-pyridinyl)-1,5-isoquinolinediamine | 343.2 |
| 18 | A | 6-methyl-N5-(3-(4-pyrimidinyl)-2-pyridinyl)-N1-(3-((trifluoromethyl)oxy)phenyl)-1,5-isoquinolinediamine | 489.2 |
| 19 | A | 6-methyl-N1-(4-(methyloxy)-3-(trifluoromethyl)phenyl)-N5-(3-(4-pyrimidinyl)-2-pyridinyl)-1,5-isoquinolinediamine | 503.2 |
| 24 | B | N-methyl-6-(6-methyl-1-((3-(trifluoromethyl)phenyl) amino)-5-isoquinolinyl)-2-quinazolinamine | 460.2 |
| 25 | B | N-methyl-6-(6-methyl-1-((3-((1-methylethyl)oxy)phenyl) amino)-5-isoquinolinyl)-2-quinazolinamine | 450.2 |
| 26 | B | N-methyl-6-(6-methyl-1-((3-(1-methylethyl)phenyl)amino)-5-isoquinolinyl)-2-quinazolinamine | 434.2 |
| 27 | B | 6-(1-((5-(1,1-dimethylethyl)-3-isoxazolyl)amino)-6-methyl-5-isoquinolinyl)-N-methyl-2-quinazolinamine | 439.2 |
| 28 | B | 6-(1-((3-(1,1-dimethylethyl) phenyl)amino)-6-methyl-5-isoquinolinyl)-N-methyl-2-quinazolinamine | 448.2 |
| 29 | B | 6-(1-((3-chlorophenyl)amino)-6-methyl-5-isoquinolinyl)-N-methyl-2-quinazolinamine | 426.1 |
| 30 | B | 3-((6-methyl-5-(2-(methylamino)-6-quinazolinyl)-1-isoquinolinyl)amino)benzonitrile | 417.2 |
| 31 | B | 6-(1-((3-(1,1-dimethylethyl)-1-methyl-1H-pyrazol-5-yl)amino)-6-methyl-5-isoquinolinyl)-N-methyl-2-quinazolinamine | 452.2 |
| 32 | B | N-methyl-6-(6-methyl-1-((3-((trifluoromethyl)oxy)phenyl)amino)-5-isoquinolinyl)-2-quinazolinamine | 476.2 |
| 33 | B | 6-(1-((1-acetyl-3,3-dimethyl-2,3-dihydro-1H-indol-6-yl)amino)-6-methyl-5-isoquinolinyl)-N-methyl-2-quinazolinamine | 503.2 |
| 34 | B | N-methyl-6-(6-methyl-1-((4-(trifluoromethyl)-2-pyridinyl)amino)-5-isoquinolinyl)-2-quinazolinamine | 461.2 |
| 35 | B | N-methyl-6-(6-methyl-1-((4-(methyloxy)-3-(trifluoromethyl)phenyl) amino)-5-isoquinolinyl)-2-quinazolinamine | 490.2 |
| 36 | B | 6-(1-((5-cyclopropyl-1,3,4-thiadiazol-2-yl)amino)-6-methyl-5-isoquinolinyl)-N-methyl-2-quinazolinamine | 440.2 |
| 37 | B | 6-(1-(1H-indazol-5-ylamino)-6-methyl-5-isoquinolinyl)-N-methyl-2-quinazolinamine | 432.2 |
| 38 | B | 6-(1-(2,3-dihydro-1H-inden-5-ylamino)-6-methyl-5-isoquinolinyl)-N-methyl-2-quinazolinamine | 432.2 |
| 39 | B | N-methyl-6-(6-methyl-1-((2-methyl-1,3-benzothiazol-5-yl)amino)-5-isoquinolinyl)-2-quinazolinamine | 463.2 |
| 40 | B | 6-(1-((4-fluoro-3-((1-methylethyl)oxy)phenyl)amino)-6-methyl-5-isoquinolinyl)-N-methyl-2-quinazolinamine | 468.2 |
| 41 | B | N-methyl-6-(6-methyl-1-((5-(trifluoromethyl)-3-pyridinyl)amino)-5-isoquinolinyl)-2-quinazolinamine | 461.2 |
| 49 | C | 6-(4-(2,3-dihydro-1H-inden-5-ylamino)-7-methylquinazolin-8-yl)-N-methylquinazolin-2-amine | 433.2 |
| 50 | C | N2,7'-dimethyl-N4'-(3-((trifluoromethyl)oxy)phenyl)-6,8'-biquinazoline-2,4'-diamine | 477.2 |
| 51 | C | N2,7'-dimethyl-N4'-(3-(trifluoromethyl)phenyl)-6,8'-biquinazoline-2,4'-diamine | 461.2 |
| 52 | C | N2,7'-dimethyl-N4'-(4-(methyloxy)-3-(trifluoromethyl)phenyl)-6,8'-biquinazoline-2,4'-diamine | 491.2 |
| 53 | C | N4'-(3-(1,1-dimethylethyl)-1-methyl-1H-pyrazol-5-yl)-N2,7'-dimethyl-6,8'-biquinazoline-2,4'-diamine | 453.2 |
| 54 | C | N4'-(1-acetyl-3,3-dimethyl-2,3-dihydro-1H-indol-6-yl)-N2,7'-dimethyl-6,8'-biquinazoline-2,4'-diamine | 504.2 |
| 55 | C | N4'-(4-chloro-3-(trifluoromethyl)phenyl)-N2,7'-dimethyl-6,8'-biquinazoline-2,4'-diamine | 495.1 |
| 56 | C | N2,7'-dimethyl-N4'-(5-(trifluoromethyl)-3-pyridinyl)-6,8'-biquinazoline-2,4'-diamine | 462.2 |
| 57 | C | N4'-(4-(1,1-dimethylethyl) cyclohexyl)-N2,7'-dimethyl-6,8'-biquinazoline-2,4'-diamine | 455.3 |
| 58 | C | N2,7'-dimethyl-N4'-(2-methyl-1,3-benzothiazol-5-yl)-6,8'-biquinazoline-2,4'-diamine | 464.2 |
| 63 | D | 6-(1,6-dimethyl-3-((3-(trifluoromethyl)phenyl) amino)-1H-indazol-7-yl)-N-methyl-2-quinazolinamine | 463.2 |
| 64 | D | 6-(1,6-dimethyl-3-((4-(methyloxy)-3-(trifluoromethyl)phenyl) amino)-1H-indazol-7-yl)-N-methyl-2-quinazolinamine | 493.2 |
| 65 | D | 6-(1,6-dimethyl-3-((3-((trifluoromethyl)oxy)phenyl)amino)-1H-indazol-7-yl)-N-methyl-2-quinazolinamine | 479.2 |
| 68 | E | 6-methyl-N5-(3-(6-(methylamino)-4-pyrimidinyl)-2-pyridinyl)-N1-(3-((trifluoromethyl)oxy)phenyl)-1,5-isoquinolinediamine | 518.2 |
| 69 | E | N1-(3-tert-butyl-1-methyl-1H-pyrazol-5-yl)-6-methyl-N5-(3-(6-(methylamino)pyrimidin-4-yl)pyridin-2-yl)isoquinoline-1,5-diamine | 494.3 |
| 70 | E | N1-(4-methoxy-3-(trifluoromethyl)phenyl)-6-methyl-N5-(3-(6-(methylamino)pyrimidin-4-yl)pyridin-2-yl)isoquinoline-1,5-diamine | 532.2 |
| 71 | E | 6-methyl-N5-(3-(6-(methylamino)-4-pyrimidinyl)-2-pyridinyl)-N1-(2-methyl-1,3-benzothiazol-5-yl)-1,5-isoquinolinediamine | 505.2 |

TABLE I-continued

| Ex. No. | Synth. Method | Structure ACD Name | MS (M + H)+ |
|---|---|---|---|
| 72 | E | N1-(4,4-dimethyl-1,2,3,4-tetrahydro-7-quinolinyl)-6-methyl-N5-(3-(6-(methylamino)-4-pyrimidinyl)-2-pyridinyl)-1,5-isoquinolinediamine | 517.3 |
| 73 | E | N1-(3-ethynylphenyl)-6-methyl-N5-(3-(6-(methylamino)-4-pyrimidinyl)-2-pyridinyl)-1,5-isoquinolinediamine | 458.2 |
| 78 | F | N-methyl-6-(6-methyl-3-((3-((1-methylethyl)oxy)phenyl) amino)-1H-indazol-7-yl)-2-quinazolinamine | 439.2 |
| 79 | G | 6-(1-((3,3-dimethyl-2,3-dihydro-1H-indol-6-yl)amino)-6-methyl-5-isoquinolinyl)-N-methyl-2-quinazolinamine | 461.2 |
| 80 | G | N1-(3,3-dimethyl-2,3-dihydro-1H-indol-6-yl)-6-methyl-N5-(3-(4-pyrimidinyl)-2-pyridinyl)-1,5-isoquinolinediamine | 474.2 |
| 81 | G | N4'-(3,3-dimethyl-2,3-dihydro-1H-indol-6-yl)-N2,7'-dimethyl-6,8'-biquinazoline-2,4'-diamine | 462.2 |
| 86 | H | 6-(2,7-dimethyl-4-(3-(trifluoromethoxy)phenylamino)quinazolin-8-yl)-N-methylquinazolin-2-amine | 491.2 |

Various experimental methods have been employed to synthesize compounds of Formulas I, II, IIa, III and IIIa, as more generally described in Schemes 1-21 above, and further described in more detail by the representative examples 87-439 below. Table II below is followed by the written Examples further describing selected representative intermediates (not in table II) and representative compounds of the invention in table II.

| Ex. No. | Method | Compound name | Mass Data |
|---|---|---|---|
| 87 | A | N1-(4-chlorophenyl)-6-methyl-N5-(3-(pyrimidin-4-yl)pyridin-2-yl)isoquinoline-1,5-diamine | 439 |
| 88 | A | 7-fluoro-6-methyl-N5-(3-(6-(methylamino)pyrimidin-4-yl)pyridin-2-yl)-N1-(2-methylbenzo[d]thiazol-5-yl)isoquinoline-1,5-diamine | 523 |
| 89 | A | N1-(3-bromophenyl)-6-methyl-N5-(3-(pyrimidin-4-yl)pyridin-2-yl)isoquinoline-1,5-diamine | 483 |
| 90 | A | N1-(4-chlorophenyl)-6-methyl-N5-(3-(pyridin-4-yl)pyridin-2-yl)isoquinoline-1,5-diamine | 438 |
| 91 | A | N1-(4-chlorophenyl)-6-methyl-N5-(3-(2-(methylamino)pyridin-4-yl)pyridin-2-yl)isoquinoline-1,5-diamine | 467 |
| 92 | B | 4,4-dimethyl-7-(6-methyl-5-(2-(methylamino)quinazolin-6-yl)isoquinolin-1-ylamino)-3,4-dihydroquinolin-2(1H)-one | 489 |
| 93 | B | 6-(1-(3,3-dimethyl-2,3-dihydrobenzofuran-5-ylamino)-6-methylisoquinolin-5-yl)-N-methylquinazolin-2-amine | 462 |
| 94 | B | 6-(1-(4,4-difluorochroman-6-ylamino)-6-methylisoquinolin-5-yl)-N-methylquinazolin-2-amine | 484 |
| 95 | B | N1-isopropyl-N3-(6-methyl-5-(2-(methylamino)quinazolin-6-yl)isoquinolin-1-yl)benzene-1,3-diamine | 449 |
| 96 | B | 6-(1-(2-tert-butylpyrimidin-5-ylamino)-6-methylisoquinolin-5-yl)-N-methylquinazolin-2-amine | 450 |
| 97 | B | 3,3-dimethyl-6-(6-methyl-5-(2-(methylamino)quinazolin-6-yl)isoquinolin-1-ylamino)indolin-2-one | 475 |
| 98 | B | N-methyl-6-(6-methyl-1-(1-methyl-3-(trifluoromethyl)-1H-pyrazol-5-ylamino)isoquinolin-5-yl)quinazolin-2-amine | 464 |
| 99 | B | 6-(1-(1-tert-butyl-1H-pyrazol-4-ylamino)-6-methylisoquinolin-5-yl)-N-methylquinazolin-2-amine | 438 |
| 100 | B | 6-(1-(2-tert-butylpyrimidin-4-ylamino)-6-methylisoquinolin-5-yl)-N-methylquinazolin-2-amine | 450 |
| 101 | B | 6-(1-(4-chlorophenylamino)-6-methylisoquinolin-5-yl)-N-methylquinazolin-2-amine | 426 |
| 102 | B | 6-(1-(2-isopropylpyrimidin-4-ylamino)-6-methylisoquinolin-5-yl)-N-methylquinazolin-2-amine | 436 |
| 103 | B | 4-(6-methyl-5-(2-(methylamino)quinazolin-6-yl)isoquinolin-1-ylamino)benzonitrile | 417 |
| 104 | C | N1-isopropyl-N3-(7-methyl-8-(2-(methylamino)quinazolin-6-yl)quinazolin-4-yl)benzene-1,3-diamine | 450 |

| Ex. No. | Method | Compound name | Mass Data |
|---|---|---|---|
| 105 | C | 7-methyl-8-(2-(methylamino)quinazolin-6-yl)-N-(4-(methylsulfonyl)phenyl)quinazolin-4-amine | 471 |
| 106 | C | 7-methyl-8-(2-(methylamino)quinazolin-6-yl)-N-(3-(methylsulfonyl)phenyl)quinazolin-4-amine | 471 |
| 107 | C | N-methyl-6-(7-methyl-4-(1-methyl-3-(trifluoromethyl)-1H-pyrazol-5-ylamino)quinazolin-8-yl)quinazolin-2-amine | 465 |
| 108 | C | 6-(1-(2,2-difluorobenzo[d][1,3]dioxol-5-ylamino)-6-methylisoquinolin-5-yl)-N-methylquinazolin-2-amine | 472 |
| 109 | C | 6-(4-(4,4-difluoro-3,4-dihydro-2H-chromen-6-ylamino)-7-methylquinazolin-8-yl)-N-methylquinazolin-2-amine | 485 |
| 110 | C | N-methyl-6-(7-methyl-4-(2-methylbenzo[d]thiazol-6-ylamino)quinazolin-8-yl)quinazolin-2-amine | 464 |
| 111 | C | 6-(4-(2,2-difluorobenzo[d][1,3]dioxol-5-ylamino)-7-methylquinazolin-8-yl)-N-methylquinazolin-2-amine | 473 |
| 112 | C | 6-(4-(5-tert-butyl-1,3,4-thiadiazol-2-ylamino)-7-methylquinazolin-8-yl)-N-methylquinazolin-2-amine | 457 |
| 113 | C | N-methyl-6-(7-methyl-4-(5-(trifluoromethyl)-1,3,4-thiadiazol-2-ylamino)quinazolin-8-yl)quinazolin-2-amine | 469 |
| 114 | C | 6-(4-(2,2-dimethyl-2H-chromen-6-ylamino)-7-methylquinazolin-8-yl)-N-methylquinazolin-2-amine | 475 |
| 115 | C | 4,4-dimethyl-7-(7-methyl-8-(2-(methylamino)quinazolin-6-yl)quinazolin-4-ylamino)-3,4-dihydroquinolin-2(1H)-one | 490 |
| 116 | C | 6-(4-(2,2-dimethyl-3,4-dihydro-2H-chromen-6-ylamino)-7-methylquinazolin-8-yl)-N-methylquinazolin-2-amine | 477 |
| 117 | C | N-(3-(7-methyl-8-(2-(methylamino)quinazolin-6-yl)quinazolin-4-ylamino)phenyl)methanesulfonamide | 486 |
| 118 | C | N-methyl-6-(7-methyl-4-(1-methyl-1H-benzo[d]imidazol-4-ylamino)quinazolin-8-yl)quinazolin-2-amine | 447 |
| 119 | C | 6-(4-(3,3-dimethyl-2,3-dihydrobenzofuran-5-ylamino)-7-methylquinazolin-8-yl)-N-methylquinazolin-2-amine | 463 |
| 120 | C | N-methyl-6-(7-methyl-4-(3-(oxazol-5-yl)phenylamino)quinazolin-8-yl)quinazolin-2-amine | 460 |
| 121 | C | 6-(4-(2-tert-butylpyrimidin-5-ylamino)-7-methylquinazolin-8-yl)-N-methylquinazolin-2-amine | 451 |
| 122 | C | 3,3-dimethyl-6-(7-methyl-8-(2-(methylamino)quinazolin-6-yl)quinazolin-4-ylamino)indolin-2-one | 476 |
| 123 | C | 6-(4-(3H-benzo[d]imidazol-5-ylamino)-7-methylquinazolin-8-yl)-N-methylquinazolin-2-amine | 433 |
| 124 | C | N2-methyl-N5-(7-methyl-8-(2-(methylamino)quinazolin-6-yl)quinazolin-4-yl)pyrimidine-2,5-diamine | 424 |
| 125 | C | N2-isopropyl-N5-(7-methyl-8-(2-(methylamino)quinazolin-6-yl)quinazolin-4-yl)pyrimidine-2,5-diamine | 452 |
| 126 | C | tert-butyl 4-(5-(7-methyl-8-(2-(methylamino)quinazolin-6-yl)quinazolin-4-ylamino)pyrimidin-2-yl)piperazine-1-carboxylate | 579 |
| 127 | C | 4-(7-methyl-8-(2-(methylamino)quinazolin-6-yl)quinazolin-4-ylamino)benzonitrile | 418 |
| 128 | C* | N-(6-(4-(4,4-dimethyl-2-oxo-1,2,3,4-tetrahydroquinolin-7-ylamino)-7-methylquinazolin-8-yl)quinazolin-2-yl)propionamide | 532 |
| 129 | C* | N-(6-(4-(4,4-dimethyl-2-oxo-1,2,3,4-tetrahydroquinolin-7-ylamino)-7-methylquinazolin-8-yl)quinazolin-2-yl)isobutyramide | 546 |

-continued

| Ex. No. | Method | Compound name | Mass Data |
|---|---|---|---|
| 130 | C* | 2-(6-(4-(4,4-dimethyl-2-oxo-1,2,3,4-tetrahydroquinolin-7-ylamino)-7-methylquinazolin-8-yl)quinazolin-2-ylamino)-2-oxoethyl acetate | 576 |
| 131 | C* | N-(6-(4-(4,4-dimethyl-2-oxo-1,2,3,4-tetrahydroquinolin-7-ylamino)-7-methylquinazolin-8-yl)quinazolin-2-yl)cyclopropanecarboxamide | 544 |
| 132 | C* | 7-(8-(2-aminoquinazolin-6-yl)-7-methylquinazolin-4-ylamino)-4,4-dimethyl-3,4-dihydroquinolin-2(1H)-one | 476 |
| 133 | C* | N-(6-(4-(4,4-dimethyl-2-oxo-1,2,3,4-tetrahydroquinolin-7-ylamino)-7-methylquinazolin-8-yl)quinazolin-2-yl)acetamide | 518 |
| 134 | C* | (S)-1-(6-(4-(4,4-dimethyl-2-oxo-1,2,3,4-tetrahydroquinolin-7-ylamino)-7-methylquinazolin-8-yl)quinazolin-2-ylamino)-1-oxopropan-2-yl acetate | 590 |
| 135 | C* | N-(6-(7-methyl-4-(3-(trifluoromethyl)phenylamino)quinazolin-8-yl)quinazolin-2-yl)propionamide | 503 |
| 136 | C* | N-(6-(7-methyl-4-(3-(trifluoromethyl)phenylamino)quinazolin-8-yl)quinazolin-2-yl)isobutyramide | 517 |
| 137 | C* | N-(6-(7-methyl-4-(3-(trifluoromethyl)phenylamino)quinazolin-8-yl)quinazolin-2-yl)cyclopropanecarboxamide | 515 |
| 138 | C* | 6-(7-methyl-4-(3-(trifluoromethyl)phenylamino)quinazolin-8-yl)quinazolin-2-amine | 447 |
| 139 | C* | 2-(6-(7-methyl-4-(3-(trifluoromethyl)phenylamino)quinazolin-8-yl)quinazolin-2-ylamino)-2-oxoethyl acetate | 547 |
| 140 | C* | N-(6-(7-methyl-4-(3-(trifluoromethyl)phenylamino)quinazolin-8-yl)quinazolin-2-yl)acetamide | 489 |
| 141 | C* | N-(6-(4-(4-methoxy-3-(trifluoromethyl)phenylamino)-7-methylquinazolin-8-yl)quinazolin-2-yl)propionamide | 533 |
| 142 | C* | N-(6-(4-(4-methoxy-3-(trifluoromethyl)phenylamino)-7-methylquinazolin-8-yl)quinazolin-2-yl)isobutyramide | 547 |
| 143 | C* | 2-(6-(4-(4-methoxy-3-(trifluoromethyl)phenylamino)-7-methylquinazolin-8-yl)quinazolin-2-ylamino)-2-oxoethyl acetate | 577 |
| 144 | C* | 6-(4-(4-methoxy-3-(trifluoromethyl)phenylamino)-7-methylquinazolin-8-yl)quinazolin-2-amine | 477 |
| 145 | C* | N-(6-(4-(4-methoxy-3-(trifluoromethyl)phenylamino)-7-methylquinazolin-8-yl)quinazolin-2-yl)cyclopropanecarboxamide | 545 |
| 146 | C* | 4,4-dimethyl-7-(7-methyl-8-(1H-pyrazolo[3,4-b]pyridin-5-yl)quinazolin-4-ylamino)-3,4-dihydroquinolin-2(1H)-one | 450 |
| 147 | C* | 7-methyl-8-(1H-pyrazolo[3,4-b]pyridin-5-yl)-N-(3-(trifluoromethyl)phenyl)quinazolin-4-amine | 421 |
| 148 | C* | N-(4-methoxy-3-(trifluoromethyl)phenyl)-7-methyl-8-(1H-pyrazolo[3,4-b]pyridin-5-yl)quinazolin-4-amine | 451 |
| 149 | C* | 4,4-dimethyl-7-(7-methyl-8-(3-(methylamino)-1H-indazol-6-yl)quinazolin-4-ylamino)-3,4-dihydroquinolin-2(1H)-one | 478 |
| 150 | C* | 7-(8-(3-amino-1-methyl-1H-indazol-6-yl)-7-methylquinazolin-4-ylamino)-4,4-dimethyl-3,4-dihydroquinolin-2(1H)-one | 478 |
| 151 | C* | 4,4-dimethyl-7-(7-methyl-8-(1-methyl-3-(methylamino)-1H-indazol-6-yl)quinazolin-4-ylamino)-3,4-dihydroquinolin-2(1H)-one | 492 |
| 152 | C* | 8-methyl-6-(7-methyl-4-(1-methyl-3-(trifluoromethyl)-1H-pyrazol-5-ylamino)quinazolin-8-yl)-2-(methylamino)pyrido[2,3-d]pyrimidin-7(8H)-one | 496 |

-continued

| Ex. No. | Method | Compound name | Mass Data |
|---|---|---|---|
| 153 | C* | 6-(4-(3,3-dimethyl-2-oxoindolin-6-ylamino)-7-methylquinazolin-8-yl)-8-methyl-2-(methylamino)pyrido[2,3-d]pyrimidin-7(8H)-one | 507 |
| 154 | C* | 6-(8-(2-aminoquinazolin-6-yl)-7-methylquinazolin-4-ylamino)-3,3-dimethylindolin-2-one | 462 |
| 155 | C* | 4-(7-methyl-8-(8-methyl-2-(methylamino)-7-oxo-7,8-dihydropyrido[2,3-d]pyrimidin-6-yl)quinazolin-4-ylamino)benzonitrile | 449 |
| 156 | C* | 4-(8-(2-aminoquinazolin-6-yl)-7-methylquinazolin-4-ylamino)benzonitrile | 404 |
| 157 | C* | 8-methyl-6-(7-methyl-4-(3-(trifluoromethyl)phenylamino)quinazolin-8-yl)-2-(methylamino)pyrido[2,3-d]pyrimidin-7(8H)-one | 492 |
| 158 | C* | 6-(4-(4,4-dimethyl-2-oxo-1,2,3,4-tetrahydroquinolin-7-ylamino)-7-methylquinazolin-8-yl)-8-methyl-2-(methylamino)pyrido[2,3-d]pyrimidin-7(8H)-one | 521 |
| 159 | C* | 6-(4-(3-ethynylphenylamino)-7-methylquinazolin-8-yl)-8-methyl-2-(methylamino)pyrido[2,3-d]pyrimidin-7(8H)-one | 448 |
| 160 | D | 6-(1,6-dimethyl-3-(2-methylbenzo[d]thiazol-5-ylamino)-1H-indazol-7-yl)-N-methylquinazolin-2-amine | 466 |
| 161 | D | 6-(3-(3-bromophenylamino)-1,6-dimethyl-1H-indazol-7-yl)-N-methylquinazolin-2-amine | 473 |
| 162 | D | 1-(5-(1,6-dimethyl-7-(2-(methylamino)quinazolin-6-yl)-1H-indazol-3-ylamino)indolin-1-yl)ethanone | 478 |
| 163 | D | 6-(1,6-dimethyl-3-(pyridin-3-ylamino)-1H-indazol-7-yl)-N-methylquinazolin-2-amine | 396 |
| 164 | D | 6-(3-(indolin-5-ylamino)-1,6-dimethyl-1H-indazol-7-yl)-N-methylquinazolin-2-amine | 436 |
| 165 | D | 6-(1,6-dimethyl-3-(5-(trifluoromethyl)pyridin-3-ylamino)-1H-indazol-7-yl)-N-methylquinazolin-2-amine | 464 |
| 166 | D | 6-(3-(2,2-difluorobenzo[d][1,3]dioxol-5-ylamino)-1,6-dimethyl-1H-indazol-7-yl)-N-methylquinazolin-2-amine | 475 |
| 167 | D | 6-(3-(3,3-dimethyl-2,3-dihydrobenzofuran-5-ylamino)-1,6-dimethyl-1H-indazol-7-yl)-N-methylquinazolin-2-amine | 465 |
| 168 | D | 6-(3-(1,2-dimethyl-1H-benzo[d]imidazol-5-ylamino)-1,6-dimethyl-1H-indazol-7-yl)-N-methylquinazolin-2-amine | 463 |
| 169 | D | 6-(3-(3-isopropoxyphenylamino)-1,6-dimethyl-1H-indazol-7-yl)-N-methylquinazolin-2-amine | 453 |
| 170 | D | 5-(1,6-dimethyl-7-(2-(methylamino)quinazolin-6-yl)-1H-indazol-3-ylamino)-1-methyl-1H-benzo[d]imidazol-2(3H)-one | 465 |
| 171 | D | 6-(1,6-dimethyl-3-(pyrimidin-5-ylamino)-1H-indazol-7-yl)-N-methylquinazolin-2-amine | 397 |
| 172 | D | 6-(3-(2-methoxypyrimidin-5-ylamino)-1,6-dimethyl-1H-indazol-7-yl)-N-methylquinazolin-2-amine | 427 |
| 173 | D | 6-(1,6-dimethyl-3-(pyridin-2-ylamino)-1H-indazol-7-yl)-N-methylquinazolin-2-amine | 396 |
| 174 | D | 6-(3-(2-tert-butylpyrimidin-5-ylamino)-1,6-dimethyl-1H-indazol-7-yl)-N-methylquinazolin-2-amine | 453 |
| 175 | D | 6-(3-(3-tert-butyl-1-methyl-1H-pyrazol-5-ylamino)-1,6-dimethyl-1H-indazol-7-yl)-N-methylquinazolin-2-amine | 455 |
| 176 | D | 6-(4-(4,4-difluoro-3,4-dihydro-2H-chromen-6-ylamino)-1,6-dimethyl-1H-indazol-7-yl)-N-methylquinazolin-2-amine | 487 |
| 177 | D | 6-(3-(2-chloropyrimidin-5-ylamino)-1,6-dimethyl-1H-indazol-7-yl)-N-methylquinazolin-2-amine | 431 |
| 178 | D | 6-(3-(3-ethynylphenylamino)-1,6-dimethyl-1H-indazol-7-yl)-N-methylquinazolin-2-amine | 419 |
| 179 | D | 6-(1,6-dimethyl-3-(2-(pyrrolidin-1-yl)pyrimidin-5-ylamino)-1H-indazol-7-yl)-N-methylquinazolin-2-amine | 466 |
| 180 | D | 6-(3-(3-methoxyphenylamino)-1,6-dimethyl-1H-indazol-7-yl)-N-methylquinazolin-2-amine | 425 |
| 181 | D | 6-(3-(4-methoxyphenylamino)-1,6-dimethyl-1H-indazol-7-yl)-N-methylquinazolin-2-amine | 425 |

-continued

| Ex. No. | Method | Compound name | Mass Data |
|---|---|---|---|
| 182 | D | 6-(3-(p-toluidino)-1,6-dimethyl-1H-indazol-7-yl)-N-methylquinazolin-2-amine | 409 |
| 183 | D | 6-(3-(3-fluoro-4-methoxyphenylamino)-1,6-dimethyl-1H-indazol-7-yl)-N-methylquinazolin-2-amine | 443 |
| 184 | D | 6-(1,6-dimethyl-3-(5-methylpyridin-2-ylamino)-1H-indazol-7-yl)-N-methylquinazolin-2-amine | 410 |
| 185 | D | 6-(3-(3,4-dihydro-2H-benzo[b][1,4]dioxepin-7-ylamino)-1,6-dimethyl-1H-indazol-7-yl)-N-methylquinazolin-2-amine | 467 |
| 186 | D | 6-(1,6-dimethyl-3-(4-methyl-3,4-dihydro-2H-benzo[b][1,4]oxazin-7-ylamino)-1H-indazol-7-yl)-N-methylquinazolin-2-amine | 466 |
| 187 | D | 6-(3-(6-methoxypyridin-3-ylamino)-1,6-dimethyl-1H-indazol-7-yl)-N-methylquinazolin-2-amine | 426 |
| 188 | D | 6-(1,6-dimethyl-3-(5-methylpyridin-3-ylamino)-1H-indazol-7-yl)-N-methylquinazolin-2-amine | 410 |
| 189 | D | 6-(3-(benzofuran-5-ylamino)-1,6-dimethyl-1H-indazol-7-yl)-N-methylquinazolin-2-amine | 435 |
| 190 | D | 6-(3-(benzo[b]thiophen-5-ylamino)-1,6-dimethyl-1H-indazol-7-yl)-N-methylquinazolin-2-amine | 451 |
| 191 | D | 6-(3-(m-toluidino)-1,6-dimethyl-1H-indazol-7-yl)-N-methylquinazolin-2-amine | 409 |
| 192 | D | 6-(3-(3,4-dimethylphenylamino)-1,6-dimethyl-1H-indazol-7-yl)-N-methylquinazolin-2-amine | 423 |
| 193 | D | 6-(1,6-dimethyl-3-(4-(trifluoromethyl)phenylamino)-1H-indazol-7-yl)-N-methylquinazolin-2-amine | 463 |
| 194 | D | 6-(3-(3-chlorophenylamino)-1,6-dimethyl-1H-indazol-7-yl)-N-methylquinazolin-2-amine | 429 |
| 195 | D | 6-(3-(4-chlorophenylamino)-1,6-dimethyl-1H-indazol-7-yl)-N-methylquinazolin-2-amine | 429 |
| 196 | D | 3-(1,6-dimethyl-7-(2-(methylamino)quinazolin-6-yl)-1H-indazol-3-ylamino)benzonitrile | 420 |
| 197 | D | 6-(3-(3,4-dimethoxyphenylamino)-1,6-dimethyl-1H-indazol-7-yl)-N-methylquinazolin-2-amine | 455 |
| 198 | D | 6-(3-(3-fluoro-4-methylphenylamino)-1,6-dimethyl-1H-indazol-7-yl)-N-methylquinazolin-2-amine | 427 |
| 199 | D | 6-(3-(4-chloro-3-methylphenylamino)-1,6-dimethyl-1H-indazol-7-yl)-N-methylquinazolin-2-amine | 443 |
| 200 | D | 6-(3-(3,4-dichlorophenylamino)-1,6-dimethyl-1H-indazol-7-yl)-N-methylquinazolin-2-amine | 463 |
| 201 | D | 2-chloro-4-(1,6-dimethyl-7-(2-(methylamino)quinazolin-6-yl)-1H-indazol-3-ylamino)benzonitrile | 454 |
| 202 | D | 6-(3-(4-chloro-3-fluorophenylamino)-1,6-dimethyl-1H-indazol-7-yl)-N-methylquinazolin-2-amine | 447 |
| 203 | D | 6-(3-(3-chloro-4-fluorophenylamino)-1,6-dimethyl-1H-indazol-7-yl)-N-methylquinazolin-2-amine | 447 |
| 204 | D | 6-(3-(4-(1H-imidazol-1-yl)phenylamino)-1,6-dimethyl-1H-indazol-7-yl)-N-methylquinazolin-2-amine | 461 |
| 205 | D | 6-(3-(3-chloro-4-methylphenylamino)-1,6-dimethyl-1H-indazol-7-yl)-N-methylquinazolin-2-amine | 443 |
| 206 | D | 6-(3-(3-chloro-5-fluorophenylamino)-1,6-dimethyl-1H-indazol-7-yl)-N-methylquinazolin-2-amine | 447 |
| 207 | D | 6-(3-(4-chloro-3-methoxyphenylamino)-1,6-dimethyl-1H-indazol-7-yl)-N-methylquinazolin-2-amine | 459 |
| 208 | D | 6-(3-(4,6-dimethylpyridin-2-ylamino)-1,6-dimethyl-1H-indazol-7-yl)-N-methylquinazolin-2-amine | 424 |
| 209 | D | 6-(3-(6-methoxypyridin-2-ylamino)-1,6-dimethyl-1H-indazol-7-yl)-N-methylquinazolin-2-amine | 426 |
| 210 | D | 6-(3-(4-(1H-pyrrol-1-yl)phenylamino)-1,6-dimethyl-1H-indazol-7-yl)-N-methylquinazolin-2-amine | 460 |
| 211 | D | 5-(1,6-dimethyl-7-(2-(methylamino)quinazolin-6-yl)-1H-indazol-3-ylamino)-2-fluorobenzonitrile | 438 |

-continued

| Ex. No. | Method | Compound name | Mass Data |
|---|---|---|---|
| 212 | D | 6-(3-(4-(difluoromethoxy)phenylamino)-1,6-dimethyl-1H-indazol-7-yl)-N-methylquinazolin-2-amine | 461 |
| 213 | D | 6-(1,6-dimethyl-7-(2-(methylamino)quinazolin-6-yl)-1H-indazol-3-ylamino)nicotinonitrile | 421 |
| 214 | D | 6-(3-(5-chloro-2-fluorophenylamino)-1,6-dimethyl-1H-indazol-7-yl)-N-methylquinazolin-2-amine | 447 |
| 215 | D | 6-(3-(3-isopropylphenylamino)-1,6-dimethyl-1H-indazol-7-yl)-N-methylquinazolin-2-amine | 437 |
| 216 | D | 6-(3-(4-methoxy-3-methylphenylamino)-1,6-dimethyl-1H-indazol-7-yl)-N-methylquinazolin-2-amine | 439 |
| 217 | D | 6-(3-(3,4-difluoro-5-methoxyphenylamino)-1,6-dimethyl-1H-indazol-7-yl)-N-methylquinazolin-2-amine | 461 |
| 218 | D | 6-(3-(3-(1H-pyrrol-1-yl)phenylamino)-1,6-dimethyl-1H-indazol-7-yl)-N-methylquinazolin-2-amine | 460 |
| 219 | D | 6-(3-(5-fluoro-6-methylpyridin-2-ylamino)-1,6-dimethyl-1H-indazol-7-yl)-N-methylquinazolin-2-amine | 428 |
| 220 | D | 6-(3-(benzo[d]thiazol-6-ylamino)-1,6-dimethyl-1H-indazol-7-yl)-N-methylquinazolin-2-amine | 452 |
| 221 | D | 6-(3-(5-chloro-6-methoxypyridin-3-ylamino)-1,6-dimethyl-1H-indazol-7-yl)-N-methylquinazolin-2-amine | 460 |
| 222 | D | 6-(3-(3,5-dimethoxyphenylamino)-1,6-dimethyl-1H-indazol-7-yl)-N-methylquinazolin-2-amine | 455 |
| 223 | D | 6-(3-(3-(difluoromethyl)-4-fluorophenylamino)-1,6-dimethyl-1H-indazol-7-yl)-N-methylquinazolin-2-amine | 463 |
| 224 | D | N1-(1,6-dimethyl-7-(2-(methylamino)quinazolin-6-yl)-1H-indazol-3-yl)-N4,N4-dimethylbenzene-1,4-diamine | 438 |
| 225 | D | 6-(1,6-dimethyl-3-(6-methylpyridin-3-ylamino)-1H-indazol-7-yl)-N-methylquinazolin-2-amine | 410 |
| 226 | D | 6-(3-(2-fluoro-6-methylpyridin-3-ylamino)-1,6-dimethyl-1H-indazol-7-yl)-N-methylquinazolin-2-amine | 428 |
| 227 | D | 6-(3-(benzo[d]oxazol-5-ylamino)-1,6-dimethyl-1H-indazol-7-yl)-N-methylquinazolin-2-amine | 436 |
| 228 | D | 6-(3-(5-methoxypyridin-3-ylamino)-1,6-dimethyl-1H-indazol-7-yl)-N-methylquinazolin-2-amine | 426 |
| 229 | D | 6-(3-(5-fluoropyridin-3-ylamino)-1,6-dimethyl-1H-indazol-7-yl)-N-methylquinazolin-2-amine | 414 |
| 230 | D | 6-(3-(4-((dimethylamino)methyl)phenylamino)-1,6-dimethyl-1H-indazol-7-yl)-N-methylquinazolin-2-amine | 452 |
| 231 | D | 6-(1,6-dimethyl-3-(5-(trifluoromethyl)pyridin-2-ylamino)-1H-indazol-7-yl)-N-methylquinazolin-2-amine | 464 |
| 232 | D | 6-(3-(6-(1H-pyrrol-1-yl)pyridin-3-ylamino)-1,6-dimethyl-1H-indazol-7-yl)-N-methylquinazolin-2-amine | 461 |
| 233 | D | 6-(3-(5-chloropyridin-3-ylamino)-1,6-dimethyl-1H-indazol-7-yl)-N-methylquinazolin-2-amine | 430 |
| 234 | D | 6-(1,6-dimethyl-3-(3-methylbenzo[b]thiophen-5-ylamino)-1H-indazol-7-yl)-N-methylquinazolin-2-amine | 465 |
| 235 | D | 6-(3-(3,4-difluorophenylamino)-1,6-dimethyl-1H-indazol-7-yl)-N-methylquinazolin-2-amine | 431 |
| 236 | D | 6-(3-(3-chloro-4-methoxyphenylamino)-1,6-dimethyl-1H-indazol-7-yl)-N-methylquinazolin-2-amine | 459 |
| 237 | D | 6-(3-(5-chloropyridin-2-ylamino)-1,6-dimethyl-1H-indazol-7-yl)-N-methylquinazolin-2-amine | 430 |
| 238 | D | 6-(3-(3-(difluoromethoxy)phenylamino)-1,6-dimethyl-1H-indazol-7-yl)-N-methylquinazolin-2-amine | 461 |
| 239 | D | 2-(1,6-dimethyl-7-(2-(methylamino)quinazolin-6-yl)-1H-indazol-3-ylamino)-N,N-dimethylisonicotinamide | 467 |
| 240 | D | N-(1,6-dimethyl-7-(2-(methylamino)quinazolin-6-yl)-1H-indazol-3-yl)-1,8-naphthyridin-3-amine | 447 |
| 241 | D | 6-(1,6-dimethyl-3-(4-(oxazol-2-yl)phenylamino)-1H-indazol-7-yl)-N-methylquinazolin-2-amine | 462 |

-continued

| Ex. No. | Method | Compound name | Mass Data |
|---|---|---|---|
| 242 | D | 6-(1,6-dimethyl-3-(3-(oxazol-2-yl)phenylamino)-1H-indazol-7-yl)-N-methylquinazolin-2-amine | 462 |
| 243 | D | 3-chloro-5-(1,6-dimethyl-7-(2-(methylamino)quinazolin-6-yl)-1H-indazol-3-ylamino)benzonitrile | 454 |
| 244 | D | N4-(1,6-dimethyl-7-(2-(methylamino)quinazolin-6-yl)-1H-indazol-3-yl)-2-fluoro-N1,N1-dimethylbenzene-1,4-diamine | 456 |
| 245 | D | 6-(3-(benzo[b]thiophen-3-ylamino)-1,6-dimethyl-1H-indazol-7-yl)-N-methylquinazolin-2-amine | 451 |
| 246 | D | 6-(3-(4-(1,3,4-oxadiazol-2-yl)phenylamino)-1,6-dimethyl-1H-indazol-7-yl)-N-methylquinazolin-2-amine | 463 |
| 247 | D | 5-(1,6-dimethyl-7-(2-(methylamino)quinazolin-6-yl)-1H-indazol-3-ylamino)nicotinonitrile | 421 |
| 248 | D | 5-(1,6-dimethyl-7-(2-(methylamino)quinazolin-6-yl)-1H-indazol-3-ylamino)picolinonitrile | 421 |
| 249 | D* | N-methyl-6-(7-methyl-3-(trifluoromethyl)phenylamino)-[1,2,4]triazolo[4,3-a]pyridin-8-yl)quinazolin-2-amine | 450 |
| 250 | E | N1-(2,2-difluorobenzo[d][1,3]dioxol-5-yl)-6-methyl-N5-(3-(pyrimidin-4-yl)pyridin-2-yl)isoquinoline-1,5-diamine | 485 |
| 251 | E | 6-methyl-N1-(3-(methylthio)phenyl)-N5-(3-(pyrimidin-4-yl)pyridin-2-yl)isoquinoline-1,5-diamine | 451 |
| 252 | E | 4-(6-methyl-5-(3-(pyrimidin-4-yl)pyridin-2-ylamino)isoquinolin-1-ylamino)benzonitrile | 430 |
| 253 | E | N1-(2-isopropylpyrimidin-4-yl)-6-methyl-N5-(3-(pyrimidin-4-yl)pyridin-2-yl)isoquinoline-1,5-diamine | 449 |
| 254 | E | 6-methyl-N5-(3-(pyrimidin-4-yl)pyridin-2-yl)-N1-(5-(trifluoromethyl)pyridin-3-yl)isoquinoline-1,5-diamine | 474 |
| 255 | E | 6-methyl-N5-(3-(6-(methylamino)pyrimidin-4-yl)pyridin-2-yl)-N1-(5-(trifluoromethyl)pyridin-3-yl)isoquinoline-1,5-diamine | 503 |
| 256 | E | N1-(1-tert-butyl-1H-pyrazol-4-yl)-6-methyl-N5-(3-(6-(methylamino)pyrimidin-4-yl)pyridin-2-yl)isoquinoline-1,5-diamine | 480 |
| 257 | E | 6-methyl-N5-(3-(6-(methylamino)pyrimidin-4-yl)pyridin-2-yl)-N1-(pyridin-2-yl)isoquinoline-1,5-diamine | 435 |
| 258 | E | N1-(3-isopropoxyphenyl)-6-methyl-N5-(3-(6-(methylamino)pyrimidin-4-yl)pyridin-2-yl)isoquinoline-1,5-diamine | 492 |
| 259 | E | N1-(2-tert-butylpyrimidin-4-yl)-6-methyl-N5-(3-(6-(methylamino)pyrimidin-4-yl)pyridin-2-yl)isoquinoline-1,5-diamine | 492 |
| 260 | E | N1-(2-isopropylpyrimidin-4-yl)-6-methyl-N5-(3-(6-(methylamino)pyrimidin-4-yl)pyridin-2-yl)isoquinoline-1,5-diamine | 478 |
| 261 | E | N1-(3-(dimethylamino)phenyl)-6-methyl-N5-(3-(6-(methylamino)pyrimidin-4-yl)pyridin-2-yl)isoquinoline-1,5-diamine | 477 |
| 262 | E | 6-methyl-N5-(3-(6-(methylamino)pyrimidin-4-yl)pyridin-2-yl)-N1-(pyridin-4-yl)isoquinoline-1,5-diamine | 435 |
| 263 | E | 6-methyl-N5-(3-(6-(methylamino)pyrimidin-4-yl)pyridin-2-yl)-N1-(3-(methylthio)phenyl)isoquinoline-1,5-diamine | 480 |
| 264 | E | N1-(2-tert-butylpyrimidin-5-yl)-6-methyl-N5-(3-(6-(methylamino)pyrimidin-4-yl)pyridin-2-yl)isoquinoline-1,5-diamine | 492 |
| 265 | E | N1-(4-isopropyl-3-methylphenyl)-6-methyl-N5-(3-(6-(methylamino)pyrimidin-4-yl)pyridin-2-yl)isoquinoline-1,5-diamine | 490 |
| 266 | E | 3,3-dimethyl-6-(6-methyl-5-(3-(6-(methylamino)pyrimidin-4-yl)pyridin-2-ylamino)isoquinolin-1-ylamino)indolin-2-one | 517 |
| 267 | E | 6-methyl-N5-(3-(6-(methylamino)pyrimidin-4-yl)pyridin-2-yl)-N1-((S)-1-phenylethyl)isoquinoline-1,5-diamine | 462 |
| 268 | E | N1-(3-isopropyl-1-methyl-1H-pyrazol-5-yl)-6-methyl-N5-(3-(6-(methylamino)pyrimidin-4-yl)pyridin-2-yl)isoquinoline-1,5-diamine | 480 |

-continued

| Ex. No. | Method | Compound name | Mass Data |
|---|---|---|---|
| 269 | E | N1-(3-(furan-2-yl)-1-methyl-1H-pyrazol-5-yl)-6-methyl-N5-(3-(6-(methylamino)pyrimidin-4-yl)pyridin-2-yl)isoquinoline-1,5-diamine | 504 |
| 270 | E | 6-methyl-N5-(3-(6-(methylamino)pyrimidin-4-yl)pyridin-2-yl)-N1-(6-phenylpyridazin-3-yl)isoquinoline-1,5-diamine | 512 |
| 271 | E | 6-methyl-N5-(3-(6-(methylamino)pyrimidin-4-yl)pyridin-2-yl)-N1-(6-methylpyridazin-3-yl)isoquinoline-1,5-diamine | 450 |
| 272 | E | N1-benzyl-6-methyl-N5-(3-(6-(methylamino)pyrimidin-4-yl)pyridin-2-yl)isoquinoline-1,5-diamine | 448 |
| 273 | E | 6-methyl-N5-(3-(6-(methylamino)pyrimidin-4-yl)pyridin-2-yl)-N1-((R)-1-phenylethyl)isoquinoline-1,5-diamine | 462 |
| 274 | E | N1-(2-methoxypyrimidin-4-yl)-6-methyl-N5-(3-(6-(methylamino)pyrimidin-4-yl)pyridin-2-yl)isoquinoline-1,5-diamine | 466 |
| 275 | E | N1-(4-methoxypyrimidin-2-yl)-6-methyl-N5-(3-(6-(methylamino)pyrimidin-4-yl)pyridin-2-yl)isoquinoline-1,5-diamine | 466 |
| 276 | E | 6-methyl-N5-(3-(6-(methylamino)pyrimidin-4-yl)pyridin-2-yl)-N1-(3-(pyrrolidin-1-yl)phenyl)isoquinoline-1,5-diamine | 503 |
| 277 | E | N1-(4-fluoro-3-methoxyphenyl)-6-methyl-N5-(3-(6-(methylamino)pyrimidin-4-yl)pyridin-2-yl)isoquinoline-1,5-diamine | 482 |
| 278 | E | N1-(3,4-dimethoxyphenyl)-6-methyl-N5-(3-(6-(methylamino)pyrimidin-4-yl)pyridin-2-yl)isoquinoline-1,5-diamine | 494 |
| 279 | E | 3-fluoro-4-(6-methyl-5-(3-(6-(methylamino)pyrimidin-4-yl)pyridin-2-ylamino)isoquinolin-1-ylamino)benzonitrile | 477 |
| 280 | E | 6-methyl-N5-(3-(6-(methylamino)pyrimidin-4-yl)pyridin-2-yl)-N1-(5-(1,1,1-trifluoropropan-2-yloxy)pyridin-3-yl)isoquinoline-1,5-diamine | 547 |
| 281 | E* | N1-(3-isopropylphenyl)-6-methyl-N5-(3-(6-(methylamino)pyrimidin-4-yl)pyridin-2-yl)isoquinoline-1,5-diamine | 476 |
| 282 | E* | N1-(4-tert-butylphenyl)-6-methyl-N5-(3-(6-(methylamino)pyrimidin-4-yl)pyridin-2-yl)isoquinoline-1,5-diamine | 490 |
| 283 | E* | 6-methyl-N5-(3-(6-(methylamino)pyrimidin-4-yl)pyridin-2-yl)-N1-(4-(trifluoromethyl)phenyl)isoquinoline-1,5-diamine | 502 |
| 284 | E* | 6-methyl-N5-(3-(6-(methylamino)pyrimidin-4-yl)pyridin-2-yl)-N1-(3-(trifluoromethyl)phenyl)isoquinoline-1,5-diamine | 502 |
| 285 | E* | N1-(4-chloro-3-(trifluoromethyl)phenyl)-6-methyl-N5-(3-(6-(methylamino)pyrimidin-4-yl)pyridin-2-yl)isoquinoline-1,5-diamine | 536 |
| 286 | E* | N1-(2-fluoro-5-(trifluoromethyl)phenyl)-6-methyl-N5-(3-(6-(methylamino)pyrimidin-4-yl)pyridin-2-yl)isoquinoline-1,5-diamine | 520 |
| 287 | E* | N1-(3-chlorophenyl)-6-methyl-N5-(3-(6-(methylamino)pyrimidin-4-yl)pyridin-2-yl)isoquinoline-1,5-diamine | 468 |
| 288 | E* | 6-methyl-N5-(3-(6-(methylamino)pyrimidin-4-yl)pyridin-2-yl)-N1-phenylisoquinoline-1,5-diamine | 434 |
| 289 | E* | N1-(4-isopropylphenyl)-6-methyl-N5-(3-(6-(methylamino)pyrimidin-4-yl)pyridin-2-yl)isoquinoline-1,5-diamine | 476 |
| 290 | E* | N1-(3,4-dichlorophenyl)-6-methyl-N5-(3-(6-(methylamino)pyrimidin-4-yl)pyridin-2-yl)isoquinoline-1,5-diamine | 502 |
| 291 | E* | N1-(4-fluoro-3-(trifluoromethyl)phenyl)-6-methyl-N5-(3-(6-(methylamino)pyrimidin-4-yl)pyridin-2-yl)isoquinoline-1,5-diamine | 520 |
| 292 | E* | N1-(3-chloro-4-fluorophenyl)-6-methyl-N5-(3-(6-(methylamino)pyrimidin-4-yl)pyridin-2-yl)isoquinoline-1,5-diamine | 486 |
| 293 | E* | 3-(6-methyl-5-(3-(6-(methylamino)pyrimidin-4-yl)pyridin-2-ylamino)isoquinolin-1-ylamino)benzonitrile | 459 |

| Ex. No. | Method | Compound name | Mass Data |
|---|---|---|---|
| 294 | E* | 6-methyl-N5-(3-(6-(methylamino)pyrimidin-4-yl)pyridin-2-yl)-N1-(2-methylbenzo[d]thiazol-6-yl)isoquinoline-1,5-diamine | 505 |
| 295 | E* | 4-(6-methyl-5-(3-(6-(methylamino)pyrimidin-4-yl)pyridin-2-ylamino)isoquinolin-1-ylamino)-2-(trifluoromethyl)benzonitrile | 527 |
| 296 | E* | 1-(3-(6-methyl-5-(3-(6-(methylamino)pyrimidin-4-yl)pyridin-2-ylamino)isoquinolin-1-ylamino)phenyl)ethanol | 478 |
| 297 | E* | N1-(3-(1-chloroethyl)phenyl)-6-methyl-N5-(3-(6-(methylamino)pyrimidin-4-yl)pyridin-2-yl)isoquinoline-1,5-diamine | 496 |
| 298 | | N1-(3-chloro-2-fluorophenyl)-6-methyl-N5-(3-(6-(methylamino)pyrimidin-4-yl)pyridin-2-yl)isoquinoline-1,5-diamine | 486 |
| 299 | E* | 2-(6-methyl-5-(3-(6-(methylamino)pyrimidin-4-yl)pyridin-2-ylamino)isoquinolin-1-ylamino)benzonitrile | 459 |
| 300 | E* | N1-(3-fluorophenyl)-6-methyl-N5-(3-(6-(methylamino)pyrimidin-4-yl)pyridin-2-yl)isoquinoline-1,5-diamine | 452 |
| 301 | E* | 4-(6-methyl-5-(3-(6-(methylamino)pyrimidin-4-yl)pyridin-2-ylamino)isoquinolin-1-ylamino)benzonitrile | 459 |
| 302 | E* | N1-(3-chloro-5-fluorophenyl)-6-methyl-N5-(3-(6-(methylamino)pyrimidin-4-yl)pyridin-2-yl)isoquinoline-1,5-diamine | 486 |
| 303 | E* | 6-methyl-N5-(3-(6-(methylamino)pyrimidin-4-yl)pyridin-2-yl)-N1-(pyridin-3-yl)isoquinoline-1,5-diamine | 435 |
| 304 | E* | 6-methyl-N1-(1-methyl-3-(trifluoromethyl)-1H-pyrazol-5-yl)-N5-(3-(6-(methylamino)pyrimidin-4-yl)pyridin-2-yl)isoquinoline-1,5-diamine | 506 |
| 305 | E* | N1-(3-methoxyphenyl)-6-methyl-N5-(3-(6-(methylamino)pyrimidin-4-yl)pyridin-2-yl)isoquinoline-1,5-diamine | 464 |
| 306 | E* | 3-fluoro-5-(6-methyl-5-(3-(6-(methylamino)pyrimidin-4-yl)pyridin-2-ylamino)isoquinolin-1-ylamino)benzonitrile | 477 |
| 307 | E* | 6-methyl-N5-(3-(6-(methylamino)pyrimidin-4-yl)pyridin-2-yl)-N1-(1H-pyrazol-4-yl)isoquinoline-1,5-diamine | 424 |
| 308 | E* | N1-(5-tert-butylisoxazol-3-yl)-6-methyl-N5-(3-(6-(methylamino)pyrimidin-4-yl)pyridin-2-yl)isoquinoline-1,5-diamine | 481 |
| 309 | E* | 6-methyl-N5-(3-(6-(methylamino)pyrimidin-4-yl)pyridin-2-yl)-N1-(2-(methylamino)pyrimidin-5-yl)isoquinoline-1,5-diamine | 465 |
| 310 | E* | N1-(5-cyclopropyl-1,3,4-thiadiazol-2-yl)-6-methyl-N5-(3-(6-(methylamino)pyrimidin-4-yl)pyridin-2-yl)isoquinoline-1,5-diamine | 482 |
| 311 | E* | N1-(3-ethoxyphenyl)-6-methyl-N5-(3-(6-(methylamino)pyrimidin-4-yl)pyridin-2-yl)isoquinoline-1,5-diamine | 478 |
| 312 | E* | N1-(1,4-dimethyl-3-(trifluoromethyl)-1H-pyrazol-5-yl)-6-methyl-N5-(3-(6-(methylamino)pyrimidin-4-yl)pyridin-2-yl)isoquinoline-1,5-diamine | 520 |
| 313 | E* | N1-(3-ethyl-1,4-dimethyl-1H-pyrazol-5-yl)-6-methyl-N5-(3-(6-(methylamino)pyrimidin-4-yl)pyridin-2-yl)isoquinoline-1,5-diamine | 480 |
| 314 | E* | N1-(2,2-difluorobenzo[d][1,3]dioxol-5-yl)-6-methyl-N5-(3-(6-(methylamino)pyrimidin-4-yl)pyridin-2-yl)isoquinoline-1,5-diamine | 514 |
| 315 | E* | 3-(6-methyl-5-(3-(6-(methylamino)pyrimidin-4-yl)pyridin-2-ylamino)isoquinolin-1-ylamino)phenol | 450 |
| 316 | E* | N1-(3-tert-butylphenyl)-6-methyl-N5-(3-(6-(methylamino)pyrimidin-4-yl)pyridin-2-yl)isoquinoline-1,5-diamine | 490 |
| 317 | E* | N1-(2,2-difluorobenzo[d][1,3]dioxol-4-yl)-6-methyl-N5-(3-(6-(methylamino)pyrimidin-4-yl)pyridin-2-yl)isoquinoline-1,5-diamine | 514 |
| 318 | E* | 3-methyl-1-(3-(6-methyl-5-(3-(6-(methylamino)pyrimidin-4-yl)pyridin-2-ylamino)isoquinolin-1-ylamino)phenyl)-1H-pyrazol-5(4H)-one | 530 |

| Ex. No. | Method | Compound name | Mass Data |
|---|---|---|---|
| 319 | E* | 6-methyl-N5-(3-(6-(methylamino)pyrimidin-4-yl)pyridin-2-yl)-N1-(3-(methylsulfonyl)phenyl)isoquinoline-1,5-diamine | 512 |
| 320 | E* | N1-(4-(dimethylamino)phenyl)-6-methyl-N5-(3-(6-(methylamino)pyrimidin-4-yl)pyridin-2-yl)isoquinoline-1,5-diamine | 477 |
| 321 | E* | 6-methyl-N5-(3-(6-(methylamino)pyrimidin-4-yl)pyridin-2-yl)-N1-(tetrahydro-2H-pyran-4-yl)isoquinoline-1,5-diamine | 442 |
| 322 | E* | N1-(5-chloro-2-fluorophenyl)-6-methyl-N5-(3-(6-(methylamino)pyrimidin-4-yl)pyridin-2-yl)isoquinoline-1,5-diamine | 486 |
| 323 | E* | N1-(2,3-dihydrobenzo[b][1,4]dioxin-6-yl)-6-methyl-N5-(3-(6-(methylamino)pyrimidin-4-yl)pyridin-2-yl)isoquinoline-1,5-diamine | 492 |
| 324 | E* | N1-(4-chlorophenyl)-6-methyl-N5-(3-(6-(methylamino)pyrimidin-4-yl)pyridin-2-yl)isoquinoline-1,5-diamine | 468 |
| 325 | E* | N1-(2-chlorophenyl)-6-methyl-N5-(3-(6-(methylamino)pyrimidin-4-yl)pyridin-2-yl)isoquinoline-1,5-diamine | 468 |
| 326 | E* | 3-chloro-5-(6-methyl-5-(3-(6-(methylamino)pyrimidin-4-yl)pyridin-2-ylamino)isoquinolin-1-ylamino)benzonitrile | 493 |
| 327 | E* | methyl 5-(6-methyl-5-(3-(6-(methylamino)pyrimidin-4-yl)pyridin-2-ylamino)isoquinolin-1-ylamino)nicotinate | 493 |
| 328 | E; CHLORINATION | N1-(4-chloro-1-methyl-3-(trifluoromethyl)-1H-pyrazol-5-yl)-6-methyl-N5-(3-(6-(methylamino)pyrimidin-4-yl)pyridin-2-yl)isoquinoline-1,5-diamine | 540 |
| 329 | E; OXIDATION | 6-methyl-N1-(3-(methylsulfonyl)phenyl)-N5-(3-(pyrimidin-4-yl)pyridin-2-yl)isoquinoline-1,5-diamine | 483 |
| 330 | A; SONOGASHIRA | 6-methyl-N5-(3-(pyrimidin-4-yl)pyridin-2-yl)-N1-(3-(2-(trimethylsilyl)ethynyl)phenyl)isoquinoline-1,5-diamine | 501 |
| 331 | A; F-deprot | N1-(3-ethynylphenyl)-6-methyl-N5-(3-(pyrimidin-4-yl)pyridin-2-yl)isoquinoline-1,5-diamine | 429 |
| 337 | I | 7-methyl-N8-(3-(6-(methylamino)pyrimidin-4-yl)pyridin-2-yl)-N4-(3-(trifluoromethyl)phenyl)quinazoline-4,8-diamine | 503 |
| 338 | I | 4-(7-methyl-8-(3-(6-(methylamino)pyrimidin-4-yl)pyridin-2-ylamino)quinazolin-4-ylamino)benzonitrile | 460 |
| 339 | I | N4-(2,2-difluorobenzo[d][1,3]dioxol-5-yl)-7-methyl-N8-(3-(6-(methylamino)pyrimidin-4-yl)pyridin-2-yl)quinazoline-4,8-diamine | 515 |
| 340 | I | 3,3-dimethyl-6-(7-methyl-8-(3-(6-(methylamino)pyrimidin-4-yl)pyridin-2-ylamino)quinazolin-4-ylamino)indolin-2-one | 518 |
| 341 | I | 3,3-dimethyl-6-(7-methyl-8-(3-(pyrimidin-4-yl)pyridin-2-ylamino)quinazolin-4-ylamino)indolin-2-one | 489 |
| 342 | I | 4-(7-methyl-8-(3-(pyrimidin-4-yl)pyridin-2-ylamino)quinazolin-4-ylamino)benzonitrile | 431 |
| 343 | I | 7-methyl-N8-(3-(6-(methylamino)pyrimidin-4-yl)pyridin-2-yl)-N4-(3-(trifluoromethoxy)phenyl)quinazoline-4,8-diamine | 519 |
| 344 | J | 6-methyl-N1-(2-methyl-5-(trifluoromethyl)phenyl)-N5-(3-(pyrimidin-4-yl)pyridin-2-yl)isoquinoline-1,5-diamine | 487 |
| 346 | K | N5-(3-(7H-pyrrolo[2,3-d]pyrimidin-4-yl)pyridin-2-yl)-6-methyl-N1-(2-methyl-5-(trifluoromethyl)phenyl)isoquinoline-1,5-diamine | 526 |
| 349 | K | 6-methyl-N1-(2-methyl-5-(trifluoromethyl)phenyl)-N5-(3-(6-(methylamino)pyrimidin-4-yl)pyridin-2-yl)isoquinoline-1,5-diamine | 516 |
| 350 | K | 4-(5-(3-(7H-pyrrolo[2,3-d]pyrimidin-4-yl)pyridin-2-ylamino)-6-methylisoquinolin-1-ylamino)benzonitrile | 469 |
| 351 | K | 6-methyl-N5-(3-(6-(methylamino)pyrimidin-4-yl)pyridin-2-yl)-N1-m-tolylisoquinoline-1,5-diamine | 448 |

-continued

| Ex. No. | Method | Compound name | Mass Data |
|---|---|---|---|
| 352 | K | N1-(4-chloro-3-methylphenyl)-6-methyl-N5-(3-(6-(methylamino)pyrimidin-4-yl)pyridin-2-yl)isoquinoline-1,5-diamine | 482 |
| 353 | K* | N1-(4-chlorophenyl)-6-methyl-N5-(3-(5-(methylamino)-1,3,4-thiadiazol-2-yl)pyridin-2-yl)isoquinoline-1,5-diamine | 474 |
| 354 | L | 8-methyl-6-(6-methyl-1-(3-(trifluoromethyl)phenylamino)isoquinolin-5-yl)-2-(methylamino)pyrido[2,3-d]pyrimidin-7(8H)-one | 491 |
| 357 | L | 6-(1-(4-methoxy-3-(trifluoromethyl)phenylamino)-6-methylisoquinolin-5-yl)-8-methyl-2-(methylamino)pyrido[2,3-d]pyrimidin-7(8H)-one | 521 |
| 358 | L | 6-(1-(2,2-difluorobenzo[d][1,3]dioxol-5-ylamino)-6-methylisoquinolin-5-yl)-8-methyl-2-(methylamino)pyrido[2,3-d]pyrimidin-7(8H)-one | 503 |
| 359 | L | 8-methyl-6-(6-methyl-1-(2-methylbenzo[d]thiazol-5-ylamino)isoquinolin-5-yl)-2-(methylamino)pyrido[2,3-d]pyrimidin-7(8H)-one | 494 |
| 360 | L | 8-methyl-2-(methylamino)-6-(1-(3-(trifluoromethyl)phenylamino)isoquinolin-5-yl)pyrido[2,3-d]pyrimidin-7(8H)-one | 477 |
| 361 | L* | 6-(6-methyl-1-(3-(trifluoromethyl)phenylamino)isoquinolin-5-yl)quinazolin-2-amine | 446 |
| 362 | L* | 2-(6-(1-(4-methoxy-3-(trifluoromethyl)phenylamino)-6-methylisoquinolin-5-yl)quinazolin-2-ylamino)acetonitrile | 515 |
| 363 | L* | N-(6-(1-(3-tert-butyl-1-methyl-1H-pyrazol-5-ylamino)-6-methylisoquinolin-5-yl)quinazolin-2-yl)acetamide | 480 |
| 364 | L* | 6-(1-(3-tert-butyl-1-methyl-1H-pyrazol-5-ylamino)-6-methylisoquinolin-5-yl)quinazolin-2-amine | 438 |
| 365 | L* | N-(3-(6-methyl-5-(2-(methylamino)quinazolin-6-yl)isoquinolin-1-ylamino)phenyl)methanesulfonamide | 485 |
| 366 | L* | 6-(1-(3-tert-butyl-1-methyl-1H-pyrazol-5-ylamino)-6-methylisoquinolin-5-yl)-N-methylpyrido[2,3-d]pyrimidin-2-amine | 453 |
| 367 | L* | 6-(1-(5-tert-butyl-1,3,4-thiadiazol-2-ylamino)-6-methylisoquinolin-5-yl)-N-methylquinazolin-2-amine | 456 |
| 368 | L* | 5-(1-(2,2-difluorobenzo[d][1,3]dioxol-5-ylamino)-6-methylisoquinolin-5-yl)-1-methyl-1H-benzo[d]imidazol-2(3H)-one | 461 |
| 369 | L* | N-(6-(1-(4-methoxy-3-(trifluoromethyl)phenylamino)-6-methylisoquinolin-5-yl)quinazolin-2-yl)acetamide | 518 |
| 370 | L* | N-(6-(1-(4-methoxy-3-(trifluoromethyl)phenylamino)-6-methylisoquinolin-5-yl)quinazolin-2-yl)propionamide | 532 |
| 371 | L* | N-(6-(1-(4-methoxy-3-(trifluoromethyl)phenylamino)-6-methylisoquinolin-5-yl)quinazolin-2-yl)cyclopropanecarboxamide | 544 |
| 372 | L* | 6-(1-(2,2-difluorobenzo[d][1,3]dioxol-5-ylamino)-6-methylisoquinolin-5-yl)quinazolin-2-amine | 458 |
| 373 | L* | 6-(7-fluoro-6-methyl-5-(2-(methylamino)quinazolin-6-yl)isoquinolin-1-ylamino)-3,3-dimethylindolin-2-one | 493 |
| 374 | L* | N-(4-methoxy-3-(trifluoromethyl)phenyl)-6-methyl-5-(3-methyl-1H-indazol-5-yl)isoquinolin-1-amine | 463 |
| 375 | L* | 5-(3-amino-1H-indazol-6-yl)-N-(4-methoxy-3-(trifluoromethyl)phenyl)-6-methylisoquinolin-1-amine | 464 |
| 376 | L* | 6-(5-(2-aminoquinazolin-6-yl)-6-methylisoquinolin-1-ylamino)-3,3-dimethylindolin-2-one | 461 |

-continued

| Ex. No. | Method | Compound name | Mass Data |
|---|---|---|---|
| 377 | L* | 6-(1-(4-methoxy-3-(trifluoromethyl)phenylamino)-6-methylisoquinolin-5-yl)-N-methylpyrido[2,3-d]pyrimidin-2-amine | 491 |
| 378 | M | 6-(1-(5-isopropoxypyridin-3-ylamino)-6-methylisoquinolin-5-yl)-N-methylquinazolin-2-amine | 451 |
| 381 | M | 6-(1-(5-tert-butoxypyridin-3-ylamino)-6-methylisoquinolin-5-yl)-N-methylquinazolin-2-amine | 465 |
| 382 | M | 6-(1-(2,3-dimethylphenylamino)-6-methylisoquinolin-5-yl)-N-methylquinazolin-2-amine | 420 |
| 383 | M | 6-(1-(2-isopropylpyrimidin-5-ylamino)-6-methylisoquinolin-5-yl)-N-methylquinazolin-2-amine | 436 |
| 392 | N | 6-(7-(4-methoxy-3-(trifluoromethyl)phenylamino)-2-methylthieno[2,3-c]pyridin-3-yl)-N-methylquinazolin-2-amine | 496 |
| 393 | N | N-methyl-6-(2-methyl-7-(3-(trifluoromethyl)phenylamino)thieno[2,3-c]pyridin-3-yl)quinazolin-2-amine | 466 |
| 395 | O | N-methyl-6-(6-methyl-1-(3-(trifluoromethyl)phenoxy)isoquinolin-5-yl)quinazolin-2-amine | 461 |
| 398 | P | N-methyl-6-(6-methyl-3-(3-(trifluoromethyl)phenylamino)benzo[d]isothiazol-7-yl)quinazolin-2-amine | 466 |
| 399 | P | 6-(3-(4-methoxy-3-(trifluoromethyl)phenylamino)-6-methylbenzo[d]isothiazol-7-yl)-N-methylquinazolin-2-amine | 496 |
| 410 | Q | 6-(8-(4-methoxy-3-(trifluoromethyl)phenylamino)-3-methyl-1,7-naphthyridin-4-yl)-N-methylquinazolin-2-amine | 491 |
| 411 | Q | 6-(8-(2,2-difluorobenzo[d][1,3]dioxol-5-ylamino)-3-methyl-1,7-naphthyridin-4-yl)-N-methylquinazolin-2-amine | 473 |
| 412 | Q | N-methyl-6-(3-methyl-8-(3-(trifluoromethyl)phenylamino)-1,7-naphthyridin-4-yl)quinazolin-2-amine | 461 |
| 413 | R | 6-methyl-5-(3-(2-(methylamino)pyrimidin-4-yl)pyridin-2-yloxy)-N-(3-(trifluoromethoxy)phenyl)isoquinolin-1-amine | 519 |
| 415 | R | 6-methyl-N-(2-methyl-5-(trifluoromethyl)phenyl)-5-(3-(2-(methylamino)pyrimidin-4-yl)pyridin-2-yloxy)isoquinolin-1-amine | 517 |
| 416 | R | 6-methyl-5-(3-(2-(methylamino)pyrimidin-4-yl)pyridin-2-yloxy)-N-(2-methylbenzo[d]thiazol-5-yl)isoquinolin-1-amine | 506 |
| 417 | R | N-(3-tert-butyl-1-methyl-1H-pyrazol-5-yl)-6-methyl-5-(3-(2-(methylamino)pyrimidin-4-yl)pyridin-2-yloxy)isoquinolin-1-amine | 495 |
| 418 | R | 6-methyl-5-(3-(2-(methylamino)pyrimidin-4-yl)pyridin-2-yloxy)-N-(3-(trifluoromethyl)phenyl)isoquinolin-1-amine | 503 |
| 419 | R | N-(4-tert-butylphenyl)-6-methyl-5-(3-(2-(methylamino)pyrimidin-4-yl)pyridin-2-yloxy)isoquinolin-1-amine | 491 |
| 420 | R | 6-methyl-5-(3-(6-(methylamino)pyrimidin-4-yl)pyridin-2-yloxy)-N-(4-(trifluoromethyl)phenyl)isoquinolin-1-amine | 503 |
| 421 | R | N-(2-tert-butylpyrimidin-5-yl)-6-methyl-5-(3-(2-(methylamino)pyrimidin-4-yl)pyridin-2-yloxy)isoquinolin-1-amine | 493 |
| 422 | R | N-(3-isopropylphenyl)-5-(3-(2-(methylamino)pyrimidin-4-yl)pyridin-2-yloxy)isoquinolin-1-amine | 463 |
| 423 | R | 5-(3-(2-(methylamino)pyrimidin-4-yl)pyridin-2-yloxy)-N-(3-(trifluoromethyl)phenyl)isoquinolin-1-amine | 489 |
| 424 | S | 1-(3-(6-methyl-5-(2-(methylamino)quinazolin-6-yl)phthalazin-1-ylamino)phenyl)ethanone | 435 |
| 433 | S; MeMgBr | 2-(3-(6-methyl-5-(2-(methylamino)quinazolin-6-yl)phthalazin-1-ylamino)phenyl)propan-2-ol | 451 |

-continued

| Ex. No. | Method | Compound name | Mass Data |
|---|---|---|---|
| 434 | S | 6-(1-(4-methoxy-3-(trifluoromethyl)phenylamino)-6-methylphthalazin-5-yl)-8-methyl-2-(methylamino)pyrido[2,3-d]pyrimidin-7(8H)-one | 522 |
| 435 | S | 4,4-dimethyl-7-(6-methyl-5-(2-(methylamino)quinazolin-6-yl)phthalazin-1-ylamino)-3,4-dihydroquinolin-2(1H)-one | 490 |
| 436 | S | 6-(1-(4-methoxy-3-(trifluoromethyl)phenylamino)-4,6-dimethylphthalazin-5-yl)-N-methylquinazolin-2-amine | 505 |
| 437 | S | 6-(4,6-dimethyl-1-(3-(trifluoromethoxy)phenylamino)phthalazin-5-yl)-N-methylquinazolin-2-amine | 491 |
| 438 | S | 7-(4,6-dimethyl-5-(2-(methylamino)quinazolin-6-yl)phthalazin-1-ylamino)-4,4-dimethyl-3,4-dihydroquinolin-2(1H)-one | 504 |

Example 328

Preparation of N1-(4-chloro-1-methyl-3-(trifluoromethyl)-1H-pyrazol-5-yl)-6-methyl-N5-(3-(6-(methylamino)pyrimidin-4-yl)pyridin-2-yl)isoquinoline-1,5-diamine To a 50 mL round-bottomed flask was added 6-methyl-N1-(1-methyl-3-(trifluoromethyl)-1H-pyrazol-5-yl)-N5-(3-(6-(methylamino)pyrimidin-4-yl)pyridin-2-yl)isoquinoline-1,5-diamine (0.16 g, 0.3 mmol), n-chlorosuccinimide (0.03 ml, 0.4 mmol) and DMF (5 mL). The reaction mixture was stirred at rt for 18 h. The reaction mixture was concentrated, diluted with chloroform, washed with 10% sodium carbonate, dried over sodium sulfate and concentrated. The crude product was purified by reverse-phase preparative HPLC using a Phenomenex Gemini column, 10 micron, C18, 110 Å, 150×30 mm, 0.1% TFA in CH$_3$CN/H$_2$O, gradient 10% to 100% over 12 min. The fractions were concentrated, dissolved in chloroform, washed with 10% sodium carbonate, dried over sodium sulfate and concentrated to give N1-(4-chloro-1-methyl-3-(trifluoromethyl)-1H-pyrazol-5-yl)-6-methyl-N5-(3-(6-(methylamino)pyrimidin-4-yl)pyridin-2-yl)isoquinoline-1,5-diamine as a solid. MS (M+H)+ 540.

Example 329

Preparation of 6-methyl-N1-(3-(methylsulfonyl)phenyl)-N5-(3-(pyrimidin-4-yl)pyridin-2-yl)isoquinoline-1,5-diamine A solution of 6-methyl-N1-(3-(methylthio)phenyl)-N5-(3-(pyrimidin-4-yl)pyridin-2-yl)isoquinoline-1,5-diamine (0.250 g, 0.555 mmol) in THF (30 mL) and MeOH (20 mL) was stirred in an ice bath and treated with a solution of Oxone®m (0.750 g, 1.22 mmol) in water (10 mL). The resulting cloudy reaction mixture was stirred at 0° C. (warming slowly to ~10° C.) for 3 h. The reaction mixture was quenched at 0° C. by the addition of satd aq Na$_2$SO$_3$ (100 mL) and stirred at that temperature for 15 min. The mixture was concentrated in vacuo to remove THF and the remaining aqueous mixture was extracted with 3:1 CHCl3:IPA (3×100 mL). The organic extract was washed with saturated aqueous NaCl (50 mL), dried over Na$_2$SO$_4$, filtered, and concentrated in vacuo to afford a yellow solid. The crude product was adsorbed onto a plug of silica gel and chromatographed through a Redi-Sep® pre-packed silica gel column (40 g), eluting with a gradient of 1% to 8% MeOH in CH2Cl2, to provide 6-methyl-N1-(3-(methylsulfonyl)phenyl)-N5-(3-(pyrimidin-4-yl)pyridin-2-yl)isoquinoline-1,5-diamine. MS (M+H)+ 483.5.

Example 330

Preparation of 6-methyl-N5-(3-(pyrimidin-4-yl)pyridin-2-yl)-N1-(3-(2-(trimethylsilyl)ethynyl)phenyl)isoquinoline-1,5-diamine Dissolved N1-(3-bromophenyl)-6-methyl-N5-(3-(pyrimidin-4-yl)pyridin-2-yl)isoquinoline-1,5-diamine (0.1125 g, 0.233 mmol) in DMF (0.427 ml, 5.84 mmol) and triethylamine (0.162 ml, 1.16 mmol). Added trimethylsilylacetylene (0.0987 ml, 0.698 mmol) followed by copper (I) iodide (0.00887 g, 0.0465 mmol) and bis(triphenylphosphine)palladium (II) chloride (0.0163 g, 0.0233 mmol). Sealed vessel and stirred reaction mixture at 70° C. After 48 hours, the reaction mixture was diluted with 100 mL water and 100 mL dichloromethane. The layers were separated and the organics washed with 2× water and 2× brine. The organics were dried over sodium sulfate, concentrated in vacuo and purified by column chromatography (20-80% EtOAc/hexanes). The combined fractions of the main peak were concentrated in vacuo to afford 6-methyl-N5-(3-(pyrimidin-4-yl)pyridin-2-yl)-N1-(3-(2-(trimethylsilyl)ethynyl)phenyl)isoquinoline-1,5-diamine as a crystalline solid. MS (M+H)+ 501.2.

Example 331

Preparation of N1-(3-ethynylphenyl)-6-methyl-N5-(3-(pyrimidin-4-yl)pyridin-2-yl)isoquinoline-1,5-diamine Suspended 6-methyl-N5-(3-(pyrimidin-4-yl)pyridin-2-yl)-N1-(3-(2-(trimethylsilyl)ethynyl)phenyl)isoquinoline-1,5-diamine (0.110 g, 0.220 mmol) in methanol (2.5 mL) and added potassium carbonate (0.0607 g, 0.439 mmol). Heated to 70° C. in a sealed tube for 90 minutes. The crude mixture was diluted with water and extracted with two portions of EtOAc. The combined organics were washed with brine, dried over Na2SO4 and concentrated. The resulting yellow solid was recrystallized from MeOH/Et2O and filtered to afford N1-(3-ethynylphenyl)-6-methyl-N5-(3-(pyrimidin-4-yl)pyridin-2-yl)isoquinoline-1,5-diamine. MS (M+H)+ 429.

Example 332

Preparation of 7-methylquinazolin-4(3H)-one

A mixture of 2-amino-4-methylbenzamide (20 g, 133 mmol) and formic acid (120 ml, 3129 mmol) was heated to 100° C. After 6 hours, the reaction was cooled down to RT and the volatiles were removed under reduced pressure. The residue was then washed carefully with aqueous saturated sodium bicarbonate and then with water. The tan solid was then dried in a vacuum oven at 45° C. overnight to give 7-methylquinazolin-4(3H)-one. MS (M+H)+ 161.

Example 333

Preparation of 6-bromo-7-methylquinazolin-4(3H)-one

To a round-bottomed flask were added methanol (70 ml, 91 mmol), glacial acetic acid (70 ml, 1212 mmol), and 7-methylquinazolin-4(3H)-one (14.56 g, 91 mmol). The reaction mixture was stirred at room temperature for 5 min followed by the slow addition of bromine (9.3 ml, 182 mmol). The reaction was stirred at room temperature for 3 h. Volatiles were evaporated under reduced pressure and the resulting crude residue washed with aqueous sodium thiosulfate to remove excess bromine and HBr, then oven dried to afford 6-bromo-7-methylquinazolin-4(3H)-one as light yellow amorphous solid. MS (M+H)+ 239, 241.

Example 334

Preparation of 6-bromo-7-methyl-8-nitroquinazolin-4(3H)-one

To $H_2SO_4$ (98%, 15 ml) was added 6-bromo-7-methylquinazolin-4(3H)-one (1.0 g, 4.2 mmol) and the mixture was stirred at rt until dissolution was complete. The mixture was cooled to 0° C. and then nitric acid (fuming) (0.26 g, 4.2 mmol) was added dropwise at 0° C. and stirred for 10 min, and then stirred at rt for 5 h. The mixture was poured onto ice (300 g) and extracted with EtOAc (3×80 ml). The combined organic layers were washed with brine (100 ml), dried over $MgSO_4$ and concentrated in vacuo. The product was recrystallized from MeOH (~15 ml). MS (M+H)+ 284, 286.

Example 335

Preparation of 6-bromo-4-chloro-7-methyl-8-nitroquinazoline To a round-bottomed flask were added phosphorous oxychloride (5 mL), 6-bromo-7-methyl-8-nitroquinazolin-4(3H)-one (800 mg, 2816 µmol). The reaction mixture was refluxed at 130° C. for 4 h. On cooling, $POCl_3$ was evaporated under reduced pressure. The resulting crude product residue was diluted with ice-water and extracted out of the aqueous layer with DCM (20 mL×3). The combined organic extracts were dried over anhydrous sodium sulfate concentrated in vacuo to afford 6-bromo-4-chloro-7-methyl-8-nitroquinazoline (595 mg, 69.8% yield) as an amorphous light yellow solid MS (M+H)+ 304, 302.

Example 336a

Preparation of 6-bromo-7-methyl-8-nitro-N-(3-(trifluoromethyl)phenyl)quinazolin-4-amine To a microwave vial were added 3-(trifluoromethyl)aniline (343 µl, 2777 µmol), 6-bromo-4-chloro-7-methyl-8-nitroquinazoline (840 mg, 2777 µmol) and IPA (5 mL). The reaction mixture was heated to 140° C. for 20 min. On cooling a ppt was observed to form which was then washed with hexane, filtered and air-dried to afford 6-bromo-7-methyl-8-nitro-N-(3-(trifluoromethyl)phenyl)quinazolin-4-amine (569 mg, 48.0% yield) as an amorphous yellow solid. MS (M+H)+ 427, 429.

Example 336b

Preparation of 7-methyl-N4-(3-(trifluoromethyl)phenyl)quinazoline-4,8-diamine

To a microwave vial were added ammonium formate (131 µl, 2664 µmol), 6-bromo-7-methyl-8-nitro-N-(3-(trifluoromethyl)phenyl)quinazolin-4-amine (569 mg, 1332 µmol), and palladium black (11.8 µl, 1332 µmol) in ethanol (10 mL). The reaction mixture was heated to 140° C. for 20 min under microwave conditions and taking care to monitor the pressure in the reaction vessel. On cooling the reaction mixture was filtered through celite and filtrate concentrated in vacuo to afford 7-methyl-N4-(3-(trifluoromethyl)phenyl)quinazoline-4,8-diamine (238 mg, 56.1% yield). MS (M+H)+ 319.

Example 337

Preparation of 7-methyl-N8-(3-(6-(methylamino)pyrimidin-4-yl)pyridin-2-yl)-N4-(3-(trifluoromethyl)phenyl)quinazoline-4,8-diamine A mixture of 7-methyl-N4-(3-(trifluoromethyl)phenyl)quinazoline-4,8-diamine (0.083 g, 0.26 mmol) and 6-(2-chloropyridin-3-yl)-N-methylpyrimidin-4-amine (0.058 g, 0.26 mmol) were placed in a clear microwave vial along with 3 ml of dioxane. While stirring, lithium bis(trimethylsilyl)amide in THF (1.6 ml, 1.6 mmol) was added dropwise with a syringe to the reaction. The vial was capped and heated in a Personal Chemistry SmithSynthesizer to 150° C. for 12 minutes. The reaction was diluted with water and ethyl acetate. The organic portion was washed (2×) with an aqueous saturated solution of sodium bicarbonate, then with water and then brine. The residue was purified by HPLC using a gradient of 5% ACN 0.1% TFA to 95% ACN 0.1% TFA in water 0.1% TFA. The pure fractions were neutralized with ammonium hydroxide and the volatiles were removed under reduced pressure. The solid that crashed out of the aqueous layer was filtered off, washed with water and dried in a vacuum oven at 45 degrees to give 7-methyl-N8-(3-(6-(methylamino)pyrimidin-4-yl)pyridin-2-yl)-N4-(3-(trifluoromethyl)phenyl)quinazoline-4,8-diamine as a light yellow solid. MS (M+H)+ 474.

Examples 338-343

The compounds of Examples 338-343 (see Table I) were prepared in a manner analogous to Example 337, utilizing various substituted phenyl-amino-methyl-quinazoline A-B rings with a pyrimidyl-pyridine C-D ring. These examples were synthesized using the general synthetic strategy described in Scheme 10 (Method I).

Example 344a

Preparation of 6-methyl-N5-(3-(pyrimidin-4-yl)pyridin-2-yl)isoquinoline-1,5-diamine A suspension of 1-chloro-6-methyl-N-(3-(pyrimidin-4-yl)pyridin-2-yl)isoquinolin-5-amine (0.562 g, 1.6 mmol) in ammonium hydroxide (20 ml, 554 mmol), split between to 2 20-mL microwave reaction vessels, was stirred at 150° C. for 2 hrs. The reaction mixture was diluted with DCM. The Aqueous was extracted 3×DCM. The combined organics were washed with Brine, dried with magnesium sulfate and concentrated under vacuum. The resulting residue was loaded on to silica and purified by column Chromatography. (ISCO 40.0 g, 1-8% MeOH in DCM, 50 min.) to give both 0.172 mgs starting material and 6-methyl-N5-(3-(pyrimidin-4-yl)pyridin-2-yl)isoquinoline-1,5-diamine. MS (M+H)+ 329.

Example 344

Preparation of 6-methyl-N1-(2-methyl-5-(trifluoromethyl)phenyl)-N5-(3-(pyrimidin-4-yl)pyridin-2-yl)isoquinoline-1,5-diamine To 6-methyl-N5-(3-(pyrimidin-4-yl)pyridin-2-yl)isoquinoline-1,5-diamine (0.040 g, 0.12 mmol), charged to a 5 mL microwave reaction vessel, 2-bromo-1-methyl-4-(trifluoromethyl)benzene (0.044 g, 0.18 mmol), 4,5-bis(diphenylphosphino)-9,9-dimethyl-9H-xanthene (0.016 g, 0.027 mmol), cesium carbonate (0.056 g, 0.17 mmol), and tris(dibenzylideneacetone)dipalladium (o) (0.011 g, 0.012 mmol) were added. The reagents were then suspended in dioxane (2.0 mL). The reaction mixture was stirred at 140° C. for 1 hrs. The reaction mixture was cooled and diluted with excess EtOAc, and partioned with aqueous sodium carbonate. The aqueous layer was back extracted 2× EtOAc. The combined organics were washed with brine, dried with magnesium sulfate and concentrated under vacuum. The resulting residue was loaded on to silica and purified by column Chromatography. (ISCO 40.0 g, 0.5-5% MeOH in DCM, 30 min.) to give 6-methyl-N1-(2-methyl-5-(trifluoromethyl)phenyl)-N5-(3-(pyrimidin-4-yl)pyridin-2-yl)isoquinoline-1,5-diamine as a solid after treatment with diethyl ether. MS (M+H)+ 487.

Example 345

Preparation of 6-(2-fluoropyridin-3-yl)-N-methylpyrimidin-4-amine

To an RBF, under a reflux condenser, was added 6-chloro-N-methylpyrimidin-4-amine (5.0 g, 35 mmol), 2-fluoropyridin-3-ylboronic acid (7.4 g, 52 mmol), potassium acetate (10 g, 104 mmol), 1-butanol (100 mL) and DI water (20 mL). The mixture was purged with Ar (vacuum/purge three times to remove oxygen), then PdCl2(P-t-Bu2Ph)2 (0.26 g, 0.42 mmol) was added. The reaction mixture was stirred in a 100° C. oil bath for 17 h. The reaction mixture was allowed to cool to room temperature and diluted with Et$_2$O (500 mL). The mixture was washed with water (3×200 mL), brine (200 mL), dried over Na$_2$SO$_4$, filtered and concentrated in vacuo to ~100 mL bright yellow butanol solution. The solution was azeotroped with hexane (3×500 mL). Upon the third azeotrope (volume ~90 mL) a white precipitate was observed. The suspended solid was collected by solution filtration and vacuum-dried to afford 2.48 g as a white solid. The filtrate was diluted with Et$_2$O (300 mL) and extracted with 1 N aq HCl (2×150 mL). The aqueous extract was basified with 5 N NaOH and extracted with Et$_2$O (2×150 mL). The organic extract was washed with saturated NaCl (100 mL), dried over Na$_2$SO$_4$, filtered, and concentrated in vacuo to afford 2.48 g as an off-white solid. Total yield of title compound: 6-(2-fluoropyridin-3-yl)-N-methylpyrimidin-4-amine (4.95 g, 70%). MS (M+H)+ 205.

Example 347

Preparation of 6-methyl-N5-(3-(6-(methylamino)pyrimidin-4-yl)pyridin-2-yl)-N1-(2-methylbenzo[d]thiazol-5-yl)isoquinoline-1,5-diamine Step 1

Alternative preparation to Example 5: To a round bottom flask fitted with reflux condenser was added 1-chloro-6-methyl-5-nitroisoquinoline (13.0 g, 50 mmol), and 2-methyl-5-benzothiazolamine (8.63 g, 52.5 mmol). Nitrogen atmosphere was applied, and the mixture was treated with isopropanol (111 mL). The reaction vessel contents were stirred to obtain a slurry. TFA (11.35 mL, 150 mmol) was then added slowly and the contents of the flask were heated to reflux. The reaction was held at reflux for 17 h, then removed from heat. The reaction mixture was filtered on a fritted funnel at room temperature. The solid was reslurried in refluxing isopropanol (222 mL) for 18 h. The slurry was then cooled to room temperature and filtered. The resulting yellow solid was then dried under vacuum at 55° C. overnight to 17.77 g 6-methyl-N1-(2-methylbenzo[d]thiazol-5-yl)isoquinoline-1,5-diamine hydrochloride (91% yield). MS (M+H)+ 351.

Step 2

Reduction of was 6-methyl-N1-(2-methylbenzo[d]thiazol-5-yl)isoquinoline-1,5-diamine hydrochloride was carried out in analogy to Example 6, using 5% Pd/C (wet) in MeOH under 45 psi H$_2$ to afford 6-methyl-N1-(2-methylbenzo[d]thiazol-5-yl)isoquinoline-1,5-diamine hydrochloride (92% yield). MS (M+H)+ 321.

Step 3

6-methyl-N1-(2-methylbenzo[d]thiazol-5-yl)isoquinoline-1,5-diamine hydrochloride (5.94 g, 16.6 mmol) and 6-(2-fluoropyridin-3-yl)-N-methylpyrimidin-4-amine (4.74 g, 23.2 mmol, 1.40 equiv.) were combined in a 350 mL screw-cap pressure tube and flushed with nitrogen. 1M LiHMDS in THF (102 mL) were added in two portions (2×51 mL) at room temperature. The pressure tube was sealed and placed immediately in a pre-heated (87° C.) sonicator bath. The reaction mixture was sonicated at 85° C. for 30 min., cooled to room temperature. The resulting thick suspension was diluted with THF (0.2 L) and quenched into a mixture of sat. aq. NH$_4$Cl (50 mL) and brine (100 mL). The organic layer was separated and concentrated in vacuo with silica (26 g). Column chromatography (CH$_2$Cl$_2$:THF 3:1)—two fractions were collected, the first contained starting material (0.5 L), fraction contained the title compound (2 L). The second fraction was concentrated in vacuo to dryness. The resulting foam was suspended in Et$_2$O (0.12 L) and sonicated until all the material was converted into a homogenous suspension of fine yellow precipitate. 6-Methyl-N5-(3-(6-(methylamino)pyrimidin-4-yl)pyridin-2-yl)-N1-(2-methylbenzo[d]thiazol-5-yl)isoquinoline-1,5-diamine was isolated by filtration as a light yellow powder (2.35 g, 28% yield). MS (M+H)+ 505.

Examples 349-354

The compounds of Examples 346, 349-353 (see Table II) were prepared in a manner analogous to Example 347, utilizing various substituted phenyl-amino-methyl-isoquinoline A-B rings with a biaryl C-D ring. These examples were synthesized using the general synthetic strategy described in Scheme 12 (Method K).

113

Example 354a

Preparation of 1-chloro-5-iodo-6-methylisoquinoline

5-Iodo-6-methylisoquinolin-1(2H)-one (2.00 g, 7.02 mmol) was treated with phosphorous oxychloride (6.54 ml, 70.2 mmol) and the mixture stirred at 100° C. for 4 hours. The mixture was cooled and the volatiles removed in vacuo. The residue was taken up in DCM and washed twice with cold water and then twice with saturated aqueous sodium bicarbonate. The organic was dried with sodium sulfate, loaded unto silica and purified by column chromatography on silica gel using 20 to 60% EA in hexanes to give 1-chloro-5-iodo-6-methylisoquinoline (2.00 g, 93.9% yield) as a tan solid. MS (M+H)+ 303.7.

Example 354b

Preparation of 5-iodo-6-methyl-N-(3-(trifluoromethyl)phenyl)isoquinolin-1-amine

To a solution of 1-chloro-5-iodo-6-methylisoquinoline (0.400 g, 1.32 mmol) in EPA (5.00 ml), charged to a 5 mL microwave reaction vessel, 3-(trifluoromethyl)aniline (0.329 ml, 2.64 mmol) was added. The reaction mixture was stirred at 140° C. for 20 min. The resulting ppt was collected by filtration and washed with excess IPA. The solid was dried under vacuum to give 5-iodo-6-methyl-N-(3-(trifluoromethyl)phenyl)isoquinolin-1-amine (0.282 g, 50.0% yield) as a pale solid. MS (M+H)+ 429.

Example 354

Preparation of 8-methyl-6-(6-methyl-1-(3-(trifluoromethyl)phenylamino)isoquinolin-5-yl)-2-(methylamino)pyrido[2,3-d]pyrimidin-7(8H)-one To a solution of 5-iodo-6-methyl-N-(3-(trifluoromethyl)phenyl)isoquinolin-1-amine (0.1680 g, 0.392 mmol) in 10:1 DMF:Water (1.5 ml), charged to a 5 mL microwave reaction vessel, 8-methyl-2-(methylamino)-6-(4,4,5,5-tetramethyl-1,3,2-dioxaborolan-2-yl)pyrido[2,3-d]pyrimidin-7(8H)-one (0.149 g, 0.471 mmol), dichlorobis(triphenyl-phosphine)palladium (ii) (0.0110 g, 0.0157 mmol), and sodium carbonate hydrate (0.102 g, 0.824 mmol) were added. The reaction mixture was stirred at 160° C. for 20 min. The reaction mixture was diluted with EtOAc and partoned with saturated sodium bicarbonate. The aqueous layer was extracted twice with EtOAc. The combined organics were washed with brine, dried over magnesium sulfate and concentrated under vacuum. The resulting residue was loaded on to silica and purified by silica gel chromatography (ISCO 2×12.0 g, 0-6% MeOH in DCM, 45 min.) and HPLC to give 8-methyl-6-(6-methyl-1-(3-(trifluoromethyl)phenylamino)isoquinolin-5-yl)-2-(methylamino)pyrido[2,3-d]pyrimidin-7(8H)-one (0.0381 g, 19.8% yield). MS (M+H)+ 491.

Examples 357-377

The compounds of Examples 354-374 (see Table I) were prepared in a manner analogous to Example 353, utilizing various substituted phenyl-amino-methyl-isoquinoline A-B rings with a fused C-D ring. These examples were synthesized using the general synthetic strategy described in Scheme 13 (Method L).

114

Example 378a

Preparation of 6-(1-(3,4-dimethoxybenzylamino)-6-methylisoquinolin-5-yl)-N-methylquinazolin-2-amine Dissolved 3,4-dimethoxybenzylamine (3.04 ml, 20.2 mmol) in NMP (15.0 mL) and added 6-(1-chloro-6-methylisoquinolin-5-yl)-N-methylquinazolin-2-amine (2.25 g, 6.72 mmol) as a solid in a sealed vessel and heated the reaction to 220° C. in the microwave 20 minutes. Dripped the reaction mixture into water and isolated the resulting precipitate. Air-dried the solid and redissolved in 2M NH3/MeOH. Concentrated in vacuo, redissolved wet slurry in EtOAc and dried the slurry over Na2SO4. Concentrated and loaded the crude material on a column, and purified the crude eluting with 20-100% EtOAc/hexanes. The pure fractions were combined and concentrated to afford 6-(1-(3,4-dimethoxybenzylamino)-6-methylisoquinolin-5-yl)-N-methylquinazolin-2-amine. MS (M+H)+ 466.

Example 378b

Preparation of 6-(1-amino-6-methylisoquinolin-5-yl)-N-methylquinazolin-2-amine

Suspended 6-(1-(3,4-dimethoxybenzylamino)-6-methylisoquinolin-5-yl)-N-methylquinazolin-2-amine (5.00 g, 10.7 mmol) in neat TFA (50 mL) and heated mixture to 55° C. for 2 hours. Removed TFA in vacuo and dissolved residue in dichloromethane and methanol (10:1). Washed organics with saturated aqueous sodium bicarbonate and loaded onto silica gel for purification via column chromatography (2-15% MeOH/DCM). Procedure afforded a white solid: 6-(1-amino-6-methylisoquinolin-5-yl)-N-methylquinazolin-2-amine. MS (M+H)+ 316.

Example 378

Preparation of 6-(1-(5-isopropoxypyridin-3-ylamino)-6-methylisoquinolin-5-yl)-N-methylquinazolin-2-amine To a solution 6-(1-amino-6-methylisoquinolin-5-yl)-N-methylquinazolin-2-amine (0.075 g, 0.24 mmol) in toluene (2.0 ml) charged to a 5-mL microwave reaction vessel, 3-bromo-5-isopropoxypyridine (0.051 g, 0.24 mmol), X-Phos (0.0091 g, 0.019 mmol), tris(dibenzylideneacetone) dipalladium (o) (0.0087 g, 0.0095 mmol), and sodium tert-butoxide (0.046 g, 0.48 mmol) were added and the reaction mixture heated to 160° C. The reaction mixture was stirred at 160° C. for 1 hrs. The reaction mixture was then diluted with EtOAc and partoned with saturated aqueous sodium bicarbonate. The aqueous layer was extracted with EtOAc twice. The combined organics were washed with brine, dried over magnesium sulfate and concentrated under vacuum. The resulting residue was purified by HPLC to give 6-(1-(5-isopropoxypyridin-3-ylamino)-6-methylisoquinolin-5-yl)-N-methylquinazolin-2-amine. MS (M+H)+ 451.

Example 382-383

The compounds of Examples 381-384 (see Table II) were prepared in a manner analogous to Example 381, utilizing various substituted phenyl-amino-methyl-isoquinoline A-B rings with a fused C-D ring. These examples were synthesized using the general synthetic strategy described in Scheme 14 (Method M).

Example 384

Preparation of 4-bromo-5-methylthiophene-2-carbaldehyde

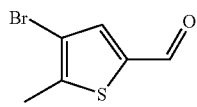

A solution of 5-methylthiophene-2-carbaldehyde (10 g, 79 mmol) in 30 ml of AcOH was added over a 7-hour period, with a syringe pump, to a stirring mixture of bromine (4.9 ml, 95 mmol) and 30 ml of AcOH, while the reaction was kept in the dark. The reaction was allowed to stir for 2 days and then poured slowly in 600 ml of 2M sodium carbonate. The mixture was stirred for 1 hour and extracted (3×) with ether. The organic layer was washed (2×) with an aqueous saturated solution of sodium bicarbonate, then with water and then brine. The organic layer was then dried with sodium sulfate, loaded unto silica and purified by column chromatography on silica gel using a gradient of 5 to 25% EtOAc in hexanes to give 4-bromo-5-methylthiophene-2-carbaldehyde (11 g, 68% yield) as yellow solid. MP 58° C. as reported in literature.

Example 385

Preparation of (E)-N-((4-bromo-5-methylthiophen-2-yl)methylene)-2,2-dimethoxyethanamine

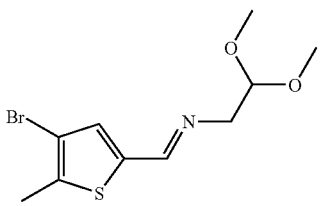

4-bromo-5-methylthiophene-2-carbaldehyde (11.00 g, 53.6 mmol) was treated with 2,2-dimethoxyethanamine (17.5 ml, 161 mmol) and the mixture stirred at 120° C. for 12 hours. The reaction was poured into water (50 ml) and stirred for 1 hour and extracted with ethyl acetate. The organic layer was washed (2×) with an aqueous saturated solution of sodium bicarbonate, then with water and then brine. The organic layer was then dried with sodium sulfate, concentrated under reduced pressure and placed under a vacuum line to give (E)-N-((4-bromo-5-methylthiophen-2-yl)methylene)-2,2-dimethoxyethanamine.

Example 386

Preparation of N-((4-bromo-5-methylthiophen-2-yl)methyl)-2,2-dimethoxyethanamine

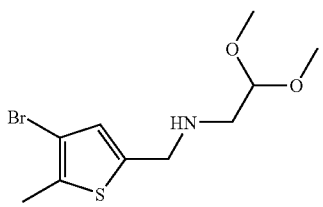

(E)-N-((4-bromo-5-methylthiophen-2-yl)methylene)-2,2-dimethoxyethanamine (15.00 g, 51.34 mmol) was taken up in EtOH (50 ml) and treated with sodium borohydride (1.942 g, 51.34 mmol) slowly (some fizzing observed). The reaction was stirred at reflux for 3 hours and at room temperature overnight. The reaction was then concentrated under reduced pressure and the residue was taken up in a mixture of ethyl acetate and water. The layer were separated and the organic layer washed (2×) with an aqueous saturated solution of sodium bicarbonate, then with water and then brine. The organic layer was dried with sodium sulfate and concentrated under reduced pressure to give N-((4-bromo-5-methylthiophen-2-yl)methyl)-2,2-dimethoxyethanamine as a brown oil. MS (M+1) 295.

Example 387

Preparation of N-((4-bromo-5-methylthiophen-2-yl)methyl)-N-(2,2-dimethoxyethyl)-4-methylbenzenesulfonamide

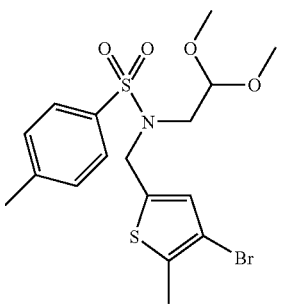

N-((4-bromo-5-methylthiophen-2-yl)methyl)-2,2-dimethoxyethanamine (14.5 g, 49 mmol) was dissolved in DCM (100 ml) and TEA (14 ml, 99 mmol) was added. The reaction was cooled to 0° C. with an ice bath and 4-tosyl chloride (8.5 ml, 59 mmol) was added portionwise. The reaction was allowed to warm up to RT and stirred overnight. The reaction was then diluted with DCM and water. The layers were separated and the organic layer was washed (2×) with an aqueous saturated solution of sodium bicarbonate, then with water and then brine. The organic layer was then dried with sodium sulfate purified by column chromatography on silica gel using a gradient of 30 to 70% EtOAc in hexanes to give N-((4-bromo-5-methylthiophen-2-yl)methyl)-N-(2,2-dimethoxyethyl)-4-methylbenzenesulfonamide as light brown oil.

Example 388

Preparation of 3-bromo-2-methylthieno[2,3-c]pyridine

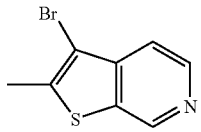

N-((4-bromo-5-methylthiophen-2-yl)methyl)-N-(2,2-dimethoxyethyl)-4-methylbenzenesulfonamide (20 g, 45 mmol) was dissolved in dioxane (70 ml) and treated with conc HCl (70 ml). The reaction was heated to reflux and stirring continued overnight. The reaction was cooled down to RT, then to 0° C. and rendered neutral with 2N NaOH. The mixture was extracted with ethyl acetate. The organic layer was washed (2×) with an aqueous saturated solution of sodium bicarbonate, then with water and then brine. The organic layer was then dried with sodium sulfate and purified by column chromatography on silica gel using a gradient of 20 to 60% EtOAc in hexanes to give 3-bromo-2-methylthieno[2,3-c]pyridine (6.2 g, 61% yield) as an yellow solid. MS (M+H)$^+$ 229

Example 389

Preparation of 3-bromo-2-methylthieno[2,3-c]pyridine-N-Oxide

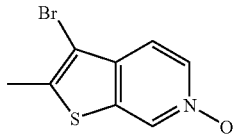

3-Bromo-2-methylthieno[2,3-c]pyridine (0.500 g, 2.19 mmol) was dissolved in DCM (10 ml) and cooled down to 0° C. m-Chloroperbenzoic acid (0.737 g, 3.29 mmol) was added to the reaction portionwise while stirring. After 4 hours, the reaction wad diluted with 1N NaOH (10 ml) and DCM (10 ml). The layers were separated and the organic layer was washed (2×) with an aqueous saturated solution of sodium bicarbonate, then with water and then brine. The organic layer was then dried with sodium sulfate, reduced in vacuo and dried to give the title compound as a yellow solid. MS (M+H)$^+$ 245

Example 390

Preparation of 3-bromo-7-chloro-2-methylthieno[2,3-c]pyridine

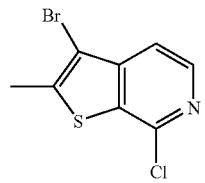

3-Bromo-2-methylthieno[2,3-c]pyridine-N-Oxide (0.500 g, 2.05 mmol) was dissolved in chloroform (10 mL) and treated with phosphorous oxychloride (0.955 ml, 10.2 mmol). The reaction was heated to 70° C. while stirring. After 3 hours, the volatiles were removed in vacuo and the residual phosphorous oxychloride was azeotroped with toluene. The resulting residue was taken up in DCM and washed (2×) with an aqueous saturated solution of sodium bicarbonate, then with water and then brine. The organic layer was then dried with sodium sulfate and purified by column chromatography on silica gel using a gradient of 20-60% EtOAc in hexanes to give 3-bromo-7-chloro-2-methylthieno[2,3-c]pyridine as a yellow solid. MS (M+H)$^+$ 263.

Example 391

Preparation of 3-bromo-N-(3-methoxy-4-(trifluoromethyl)phenyl)-2-methylthieno[2,3-c]pyridin-7-amine

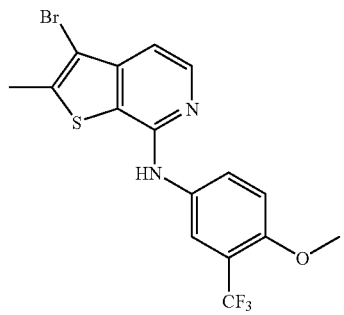

3-Bromo-7-chloro-2-methylthieno[2,3-c]pyridine (0.200 g, 0.762 mmol) and 4-methoxy-3-(trifluoromethyl)benzenamine (0.175 g, 0.914 mmol) were placed in a clear microwave vial along with 3 ml of dioxane. Lithiumbis(trimethylamide) amide 1M in tetrahydrofuran (0.762 ml, 0.762 mmol) was added dropwise to the reaction mixture while stirring. The vial was capped and heated in a Personal Chemistry SmithSynthesizer to 150° C. for 10 minutes. The reaction was diluted with EtOAc and water and the organic layer was washed (2×) with an aqueous saturated solution of sodium bicarbonate, then with water followed by brine. The organic layer was then dried with sodium sulfate and purified by column chromatography on silica gel using a gradient of 20 to 60% EtOAc in hexanes to give 3-bromo-N-(3-methoxy-4-(trifluoromethyl)phenyl)-2-methylthieno[2,3-c]pyridin-7-amine as a yellow solid. MS (M+H)+ 418.

Example 392

Preparation of 6-(7-(4-methoxy-3-(trifluoromethyl)phenylamino)-2-methylthieno[2,3-c]pyridin-3-yl)-N-methylquinazolin-2-amine 3-Bromo-N-(3-methoxy-5-(trifluoromethyl)phenyl)-2-methylthieno[2,3-c]pyridin-7-amine (0.230 g, 0.551 mmol), N-methyl-6-(4,4,5,5-tetramethyl-1,3,2-dioxaborolan-2-yl)quinazolin-2-amine (0.189 g, 0.661 mmol), dichlorobis(triphenyl-phosphine)palladium (II) (0.0193 g, 0.0276 mmol), sodium carbonate (0.117 g, 1.10 mmol) were all placed in a clear microwave vial along with 5 ml of 9:1 DMF:water. The vial was capped and heated in a Personal Chemistry SmithSynthesizer to 150° C. for 10 minutes. The reaction was diluted with water and extracted with EtAOc. The organic layer was washed (2×) with an aqueous saturated solution of sodium bicarbonate, then with water and then brine. The organic layer was then dried with sodium sulfate and purified by column chromatography on silica gel using a gradient of 50-100% EtOAc in hexanes. The pure fractions were reduced in vacuo and the residue triturated with ether to give 6-(7-(4-methoxy-3-(trifluoromethyl)phenylamino)-2-methylthieno[2,3-c]pyridin-3-yl)-N-methylquinazolin-2-amine as a yellow solid. MS (M+H)+ 496.

Example 393

N-methyl-6-(2-methyl-7-(3-(trifluoromethyl)phenylamino)thieno[2,3-c]pyridin-3-yl)quinazolin-2-amine The title compound was prepared in a manner analogous to that described in Example 393, Method N. MS (M+H)+ 466.

Example 394

Preparation of 5-iodo-6-methyl-1-(3-trifluoromethyl)phenoxy)isoquinoline

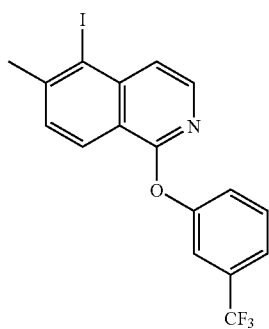

1-Chloro-5-iodo-6-methylisoquinoline (0.250 g, 0.824 mmol), 3-(trifluoromethyl)phenol (0.200 g, 1.24 mmol), cesium carbonate (0.590 g, 1.81 mmol) were all placed in a clear microwave vial along with 3 ml of DMSO. The vial was capped and heated in a Personal Chemistry SmithSynthesizer to 170° C. for 20 minutes. The reaction was diluted with water and ethyl acetate. The organic layer washed (2×) with an aqueous saturated solution of sodium bicarbonate, then with water and then brine. The organic layer was then dried with sodium sulfate and purified by column chromatography on silica gel using a gradient of 60-100% EtOAc in hexanes to give 5-iodo-6-methyl-1-(3-(trifluoromethyl)phenoxy)isoquinoline (0.260 g, 73.6% yield) as a white solid. MS (M+H)+ 430.

Example 395

Preparation of N-methyl-6-(6-methyl-1-(3-(trifluoromethyl)phenoxy)isoquinolin-5-yl)quinazolin-2-amine 5-Iodo-6-methyl-1-(3-(trifluoromethyl)phenoxy)isoquinoline (0.170 g, 0.396 mmol), N-methyl-6-(4,4,5,5-tetramethyl-1,3,2-dioxaborolan-2-yl)quinazolin-2-amine (0.124 g, 0.436 mmol), dichlorobis(triphenyl-phosphine)palladium (II) (0.0139 g, 0.0198 mmol), and sodium carbonate (0.0840 g, 0.792 mmol) were all placed in a clear microwave vial along with 5 ml of 9:1 DMF:water. The vial was capped and heated in a Personal Chemistry SmithSynthesizer to 150° C. for 10 minutes. The reaction was diluted with water and extracted with EtAOc. The organic layer was washed (2×) with an aqueous saturated solution of sodium bicarbonate, then with water and then brine. The organic layer was then dried with sodium sulfate and purified by column chromatography on silica gel using a gradient of 30-70% EtOAc in hexanes. The clean fractions were reduced in vacuo and the residue triturated with ether to give N-methyl-6-(6-methyl-1-(3-(trifluoromethyl)phenoxy)isoquinolin-5-yl)quinazolin-2-amine as a light yellow solid. MS (M+H)+ 461.

Example 396

7-iodo-6-methylbenzo[d]isothiazol-3-amine

2-Fluoro-3-iodo-4-methylbenzonitrile (2.50 g, 9.6 mmol) (ref WO2006094187), sulfur (0.34 g, 11 mmol), ammonium hydroxide 28-30% (10 ml) and 2-methoxyethanol (20 ml) were all taken into a clear high pressure glass vessel. The vessel was capped and the reaction was heated to 135° C. overnight. The reaction was allowed to cool down to RT and diluted with water and EtOAc. The organic layer was washed (2×) with an aqueous saturated solution of sodium bicarbonate, then with water and then brine. The organic layer was then dried with sodium sulfate and purified by column chromatography on silica gel using a gradient of 10-60% EtOAc in hexanes to give 7-iodo-6-methylbenzo[d]isothiazol-3-amine (0.400 g, 14% yield) as a yellow solid. MS (M+H)+ 291.

Example 397

Preparation of 6-(3-amino-6-methylbenzo[d]isothiazol-7-yl)-N-methylquinazolin-2-amine

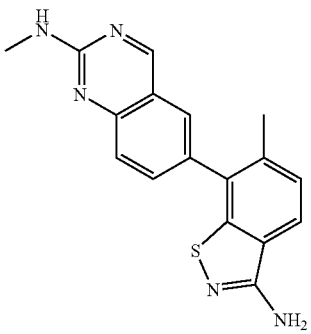

N-Methyl-6-(4,4,5,5-tetramethyl-1,3,2-dioxaborolan-2-yl)quinazolin-2-amine (0.42 g, 1.5 mmol), 7-iodo-6-methylbenzo[d]isothiazol-3-amine (0.39 g, 1.3 mmol), dichlorobis(triphenyl-phosphine)palladium (II) (0.047 g, 0.067 mmol) and sodium carbonate (0.14 g, 1.3 mmol) were all placed in a clear microwave vial along with 5 ml of 9:1 DMF:water. The vial was capped and heated in a Personal Chemistry SmithSynthesizer to 150° C. for 10 minutes. The reaction was diluted with water and extracted with EtAOc. The organic layer was washed (2×) with an aqueous saturated solution of sodium bicarbonate, then with water and then brine. The organic layer was then dried with sodium sulfate and purified by column chromatography on silica gel using a gradient of 50 to 100% EtOAc in hexanes. The clean fractions were triturated with warm ether and the solid collected by suction filtration and dried to give 6-(3-amino-6-methylbenzo[d]isothiazol-7-yl)-N-methylquinazolin-2-amine as a tan solid. MS (M+H)$^+$ 322.

Example 398

Preparation of N-methyl-6-(6-methyl-3-(3-(trifluoromethyl)phenylamino)benzo[d]isothiazol-7-yl)quinazolin-2-amine 6-(3-Amino-6-methylbenzo[d]isothiazol-7-yl)-N-methylquinazolin-2-amine (0.100 g, 0.31 mmol), 3-(trifluoromethyl)benzenamine (0.060 g, 0.37 mmol), tris(dibenzylideneacetone)dipalladium (o) (0.0085 g, 0.0093 mmol), X-phos (0.0089 g, 0.019 mmol) and sodium t-butoxide (0.042 g, 0.44 mmol) were all placed in a clear microwave vial along with 4 ml of toluene. The vial was capped and heated in a Personal Chemistry SmithSynthesizer to 150° C. for 10 minutes. The reaction was diluted with ethyl acetate and the organic layer was washed (2×) with an aqueous saturated solution of sodium bicarbonate, then with water and then brine. The organic layer was then dried with sodium sulfate and purified by column chromatography on silica gel using a gradient of 40-80% EtOAc in hexanes to give N-methyl-6-(6-methyl-3-(3-(trifluoromethyl)phenylamino)benzo[d]isothiazol-7-yl)quinazolin-2-amine as yellow solid. MS (M+H)$^+$ 466.

Example 399

6-(3-(4-methoxy-3-(trifluoromethyl)phenylamino)-6-methylbenzo[d]isothiazol-7-yl)-N-methylquinazolin-2-amine The title compound was prepared in an analogous manner to example 399, using Method P. MS (M+H)$^+$ 496.

Example 400

Preparation of 3-aminopyridin-2(1H)-one

3-Aminopyridin-2(1H)-one was synthesized according to the literature preparation found in *Chemical & Pharmaceutical Bulletin*, 24(8), 1813-21; 1976.

Example 401

Preparation of (E)-diethyl 2-((2-oxo-1,2-dihydropyridin-3-ylimino)methyl)malonate

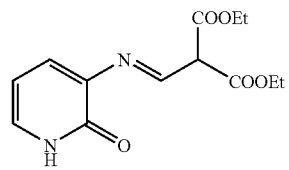

3-Aminopyridin-2(1H)-one (9.00 g, 81.7 mmol) was treated with diethyl ethoxymethylenemalonate (24.6 ml, 123 mmol) and heated to 100° C. After 3 hours, the reaction was cooled down and diluted with isopropyl alcohol. The solid that crashed out was collected by suction filtration and washed well with IPA and then ether to give diethyl 2-((2-oxo-1,2-dihydropyridin-3-ylamino)methylene)malonate (14.5 g, 63.3% yield) as a greenish solid. MS (M+H)$^+$ 281.

Example 402

Preparation of (E)-diethyl 2-((1-(4-methoxybenzyl)-2-oxo-1,2-dihydropyridin-3-ylimino)methyl)malonate

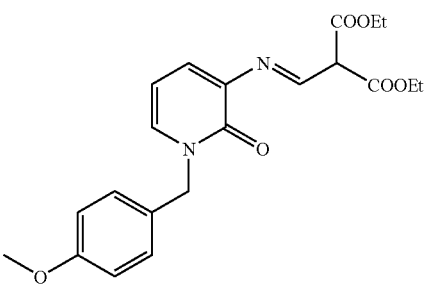

Diethyl 2-((2-oxo-1,2-dihydropyridin-3-ylamino)methylene)malonate (7.50 g, 26.8 mmol) was dissolved in DMF (30 ml) and treated with potassium carbonate (7.40 g, 53.5 mmol) and 4-methoxybenzyl chloride (5.45 ml, 40.1 mmol). The mixture was stirred at ambient temperature overnight. The reaction was diluted with water (150 ml) and the solid that crashed out was collected by suction filtration. The solid was washed with water and dried to give diethyl 2-((1-(4-methoxybenzyl)-2-oxo-1,2-dihydropyridin-3-ylamino)methylene)malonate (9.00 g, 84.0% yield) as a light green solid. MS (M+H)+ 401.

Example 403

Preparation of ethyl 7-(4-methoxybenzyl)-4-hydroxy-8-oxo-7,8-dihydro-1,7-naphthyridine-3-carboxylate

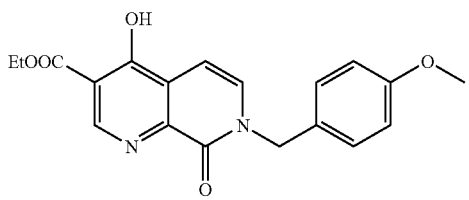

Dowtherm A (50 ml) was heated to 250° C. in a 500 ml a 3-neck rbf equipped with a temperature probe, a stir bar and a reflux condenser. Diethyl 2-((1-(4-methoxybenzyl)-2-oxo-1,2-dihydropyridin-3-ylamino)methylene)malonate (5.00 g, 12.5 mmol) was added in one portion. The mixture was stirred for 30 mins and then was rapidly cooled down using a stream of nitrogen. At around 140° C., a solid started to crash out. Once at RT, the mixture was diluted with hexanes (100 ml) and was allowed to stand overnight. The precipitate that formed was collected by suction filtration, washed with ether and dried to give ethyl 7-(4-methoxybenzyl)-4-hydroxy-8-oxo-7,8-dihydro-1,7-naphthyridine-3-carboxylate as a yellow solid. MS (M+H)+ 355.

Example 404

Preparation of 7-(4-methoxybenzyl)-4-hydroxy-3-(hydroxymethyl)-1,7-naphthyridin-8(7H)-one

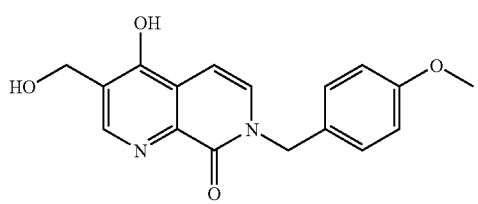

Ethyl 7-(4-methoxybenzyl)-4-hydroxy-8-oxo-7,8-dihydro-1,7-naphthyridine-3-carboxylate (4.00 g, 11 mmol) was suspended in anhydrous THF (60 ml) and the mixture was cooled down to −10° C. Lithium aluminum hydride 2M in THF (11 ml, 23 mmol) was added dropwise to the mixture. The cold bath was then removed and the reaction was stirred for two hours at room temperature. Sodium sulfate decahydrate (10 g) was added portionwise to the reaction. The mixture was stirred for 3 hours and then filtered. The cake collected in the filter funnel was extracted for 12 hours in a soxhlet apparatus in a 2:1 mixture of chloroform and methanol. The filtrate was directly loaded unto silica gel and purified by column chromatography on silica gel using a gradient of 0 to 10% methanol in DCM to give 7-(4-methoxybenzyl)-4-hydroxy-3-(hydroxymethyl)-1,7-naphthyridin-8(7H)-one (1.3 g, 37% yield) as light yellow solid. MS (M+H)+ 313.

Example 405

Preparation of 7-(4-methoxybenzyl)-4-chloro-3-(chloromethyl)-1,7-naphthyridin-8(7H)-one

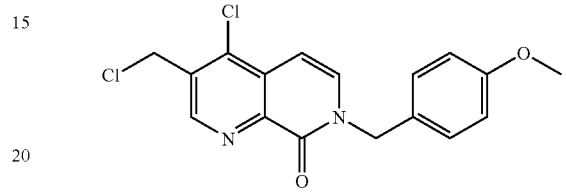

7-(4-methoxybenzyl)-4-hydroxy-3-(hydroxymethyl)-1,7-naphthyridin-8(7H)-one (1.1 g, 3.5 mmol) was suspended in chloroform and treated with phosphorous oxychloride (4.9 ml, 53 mmol) and the mixture was stirred at 85° C. After 3 hours, the reaction was cooled down to room temperature and the volatiles were removed under vacuum. Residual phosphorous oxychloride was azeotroped with toluene. The residue was dissolved in chloroform and washed with cold water (2×). The organic layer then washed (2×) with an aqueous saturated solution of sodium bicarbonate, then with water and then brine. The organic layer was then dried with sodium sulfate and purified by column chromatography on silica gel using a gradient of 0 to 5% methanol in DCM to give 7-(4-methoxybenzyl)-4-chloro-3-(chloromethyl)-1,7-naphthyridin-8(7H)-one as a yellow film. MS (M+H)+ 350.

Example 406

Preparation of 7-(4-methoxybenzyl)-4-chloro-3-methyl-1,7-naphthyridin-8(7H)-one

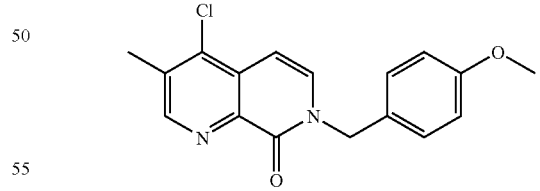

Raney Nickel 2800, slurry in H2O, active catalyst (2.5 g, 43 mmol) (wet weight) was rinsed off with ethanol and added to a suspension of 7-(4-methoxybenzyl)-4-chloro-3-(chloromethyl)-1,7-naphthyridin-8(7H)-one (1.00 g, 2.9 mmol) in 50 ml of EtOH. The reaction was stirred at RT for 30 min and then filtered off through a small pad of celite. The filtrate was concentrated under reduced pressure to give 7-(4-methoxybenzyl)-4-chloro-3-methyl-1,7-naphthyridin-8(7H)-one as a clear film. MS (M+H)+ 315.

Example 407

Preparation of 7-(4-methoxybenzyl)-3-methyl-4-(2-(methylamino)quinazolin-6-yl)-1,7-naphthyridin-8(7H)-one

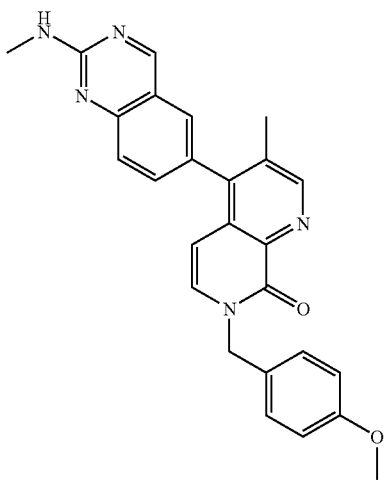

A mixture of 7-(4-methoxybenzyl)-4-chloro-3-methyl-1,7-naphthyridin-8(7H)-one (0.750 g, 2.38 mmol), N-methyl-6-(4,4,5,5-tetramethyl-1,3,2-dioxaborolan-2-yl)quinazolin-2-amine (0.815 g, 2.86 mmol), dichlorobis(triphenylphosphine)palladium (ii) (0.0836 g, 0.119 mmol) and sodium carbonate (0.758 g, 7.15 mmol) was placed in a clear microwave vial along with 10 ml of a combination of 7:3:2 DME:H$_2$O:EtOH. The vial was capped and heated in a Personal Chemistry SmithSynthesizer to 145° C. for 10 minutes. The reaction was diluted with DCM:MeOH (2:1) and the insoluble were filtered off. The filtrate was loaded directly on silica gel and purified by column chromatography on silica gel using a gradient of 0 to 10% MeOH in DCM to give 7-(4-methoxybenzyl)-3-methyl-4-(2-(methylamino)quinazolin-6-yl)-1,7-naphthyridin-8(7H)-one (0.940 g, 90.2% yield) as a yellow solid. MS (M+H)$^+$ 438.

Example 408

3-methyl-4-(2-(methylamino)quinazolin-6-yl)-1,7-naphthyridin-8(7H)-one 7-(4-Methoxybenzyl)-3-methyl-4-(2-(methylamino)quinazolin-6-yl)-1,7-naphthyridin-8(7H)-one (0.900 g, 2.06 mmol) was taken in a clear microwave vial and treated with 14 ml of TFA and 1 ml of conc HCl. The vial was capped and heated in a Personal Chemistry SmithSynthesizer to 175° C. for 45 minutes. The volatiles were evaporated under reduced pressure and residual TFA/water was azeotroped with toluene. The residue was taken up in DCM/2M MeOH and loaded unto silica. The residue was purified by column chromatography on silica gel using a gradient of 3 to 12% MeOH in DCM to give 3-methyl-4-(2-(methylamino)quinazolin-6-yl)-1,7-naphthyridin-8(7H)-one as a yellow solid. MS (M+H)$^+$ 318.

Example 409

6-(8-chloro-3-methyl-1,7-naphthyridin-4-yl)-N-methylquinazolin-2-amine

A mixture of 3-methyl-4-(2-(methylamino)quinazolin-6-yl)-1,7-naphthyridin-8(7H)-one (0.400 g, 1.26 mmol) and phosphorous oxychloride (5.00 ml, 1.26 mmol) was heated to 100° C. After 3 hours, the volatiles were removed under vacuum. Residual phosphorous oxychloride was azeotroped with toluene. The resulting residue was dissolved in chloroform and washed with cold water. The organic layer was then washed (2×) with an aqueous saturated solution of sodium bicarbonate, then with water and then brine. The organic layer was then dried with sodium sulfate and purified by column chromatography on silica gel using a gradient of 50 to 100% EtOAc in hexanes to give 6-(8-chloro-3-methyl-1,7-naphthyridin-4-yl)-N-methylquinazolin-2-amine as a yellow solid. MS (M+H)$^+$ 336.

Examples 410-412

The compounds of Examples 411-412 (see Table II) were prepared from 6-(8-chloro-3-methyl-1,7-naphthyridin-4-yl)-N-methylquinazolin-2-amine in a manner analogous to Example 24, utilizing various substituted aryl-amino-methylamino naphthyridine A-B rings with a quinazoline C-D ring. These examples were synthesized using the general synthetic strategy described in schemes 3 (Method B) and 18 (Method Q) herein.

Examples 413a

Preparation of 5-hydroxy-6-methylisoquinolin-1(2H)-one

5-Amino-6-methylisoquinolin-1(2H)-one (1.00 g, 5.74 mmol) was dissolved in 75% sulfuric acid (18.2 ml). Mixture cooled to 0° C. and treated with a solution of sodium nitrite (0.416 g, 6.03 mmol) in concentrated sulfuric acid (2.28 ml). After the mixture had been stirred for 1 hour at this temperature, water (36.0 ml) was added and the mixture warmed to 65° C. overnight. The mixture was then diluted with 150 mL water. The resulting precipitate was filtered and washed with an additional portion of water and Et2O. A brown solid was collected: 5-hydroxy-6-methylisoquinolin-1(2H)-one (0.860 g, 85.5% yield). MS (M+H)+ 176.

Example 413b

Preparation of 6-methyl-5-(3-(2-(methylamino)pyrimidin-4-yl)pyridin-2-yloxy)isoquinolin-1(2H)-one DMSO (65 mL) was added to a vial containing 5-hydroxy-6-methylisoquinolin-1(2H)-one (5.50 g, 31.4 mmol) and 4-(2-chloropyridin-3-yl)-N-methylpyrimidin-2-amine (6.93 g, 31.4 mmol). Cesium carbonate (30.7 g, 94.2 mmol) was added to the vial, and the vial was sealed and heated to 130° C. for 16 hours. The vial was allowed to cool to ambient temperature and the mixture was diluted with water (~1 L) and neutralized with AcOH. The precipitate was filtered to afford 6-methyl-5-(3-(2-(methylamino)pyrimidin-4-yl)pyridin-2-yloxy)isoquinolin-1(2H)-one. MS (M+H)+ 360.

Example 413c

Preparation of 4-(2-(1-chloro-6-methylisoquinolin-5-yloxy)pyridin-3-yl)-N-methylpyrimidin-2-amine 6-Methyl-5-(3-(2-(methylamino)pyrimidin-4-yl)pyridin-2-yloxy)isoquinolin-1(2H)-one (6.00 g, 16.7 mmol) was suspended in POCl$_3$ (100 mL) and the mixture was heated to 100° C. for 3 hours. Excess POCl$_3$ was removed in vacuo and the residue was azeotroped twice with toluene. The residue was dissolved in MeOH/DCM and saturated aqueous sodium bicarbonate solution. The aqueous layer was back-extracted twice with MeOH/DCM. Combined organics were reduced to ⅓ volume in vacuo and loaded onto a silica plug (~30 g in a fritted funnel). The plug was washed thoroughly with EtOAc and concentrated to afford 6.2 g of ~85% pure material. Trituration in EtOAc yielded 1.60 g of a tan powder. Silica gel chromatography of the residue from the organic layer using 15-75% EtOAc/hexanes afforded another 1.35 g. The combined materials amounted to 2.95 g of the title compound. MS (M+H)+ 378.

Example 413

Preparation of 6-methyl-5-(3-(2-(methylamino)pyrimidin-4-yl)pyridin-2-yloxy)-N-(3-(trifluoromethoxy)phenyl)isoquinolin-1-amine 4-(2-(1-Chloro-6-methylisoquinolin-5-yloxy)pyridin-3-yl)-N-methylpyrimidin-2-amine (0.150 g, 0.40 mmol) was suspended in dioxane (1.00 mL) to which mixture was added 3-(trifluoromethoxy)aniline (0.12 ml, 0.79 mmol). 4N HCl in dioxane (1.00 mL) was added and the mixture was stirred. The vessel was sealed and heated to 170° C. in microwave for 15 minutes. The reaction mixture was treated with 2M ammonia in methanol and concentrated directly onto silica gel. The material was chromatographed eluting with a gradient of EtOAc/hexanes (15-100%) followed by trituration of the pure material in EtOAc to afforded 6-methyl-5-(3-(2-(methylamino)pyrimidin-4-yl)pyridin-2-yloxy)-N-(3-(trifluoromethoxy)phenyl)isoquinolin-1-amine. MS (M+H)+ 519.

Examples 415-423

The compounds of Examples 415-423 (see Table II) were prepared in a manner analogous to Example 413, utilizing various substituted aryl-amino-methyl-hydroxy isoquinoline A-B rings with a biaryl C-D ring. These examples were synthesized using the general synthetic strategy described in schemes 19 and 20 (Method R) and the ultimate coupling methods described in examples 24 and 68.

Example 424

Preparation of N-tert-butyl-4-methylbenzamide

To a solution of p-toluoyl chloride (34.2 ml, 259 mmol) in DCM (250 ml), charged to a 500 mL round bottom, t-butylamine (57.3 ml, 543 mmol) was added slowly at 0° C. The reaction mixture was stirred at 0° C. for 45 min. The reaction mixture was then partioned between additional DCM and water. The organic layer was then washed with water 2 and brine. The organic layer was then dried over magnesium sulfate and concentrated under vacuum to give a white solid N-tert-butyl-4-methylbenzamide (47.07 g, 95.1% yield). MS (M+H)+ 192.

Example 425

Preparation of 2-tert-butyl-3-hydroxy-5-methylisoindolin-1-one

To a solution of N-tert-butyl-4-methylbenzamide (9.02 g, 47.2 mmol) in THF (132 ml), charged to a 250 mL round bottom, sec-butyl lithium, 1.4 m in cyclohexane (74.1 ml, 104 mmol) was added at −78° C. The reaction mixture was stirred at −78° C. for 30 min, then warmed to 0° C. for 45 min, before cooling back to −78° C. Then N,N-dimethylformamide (12.0 ml, 156 mmol) was added. The reaction mixture was stirred at −78° C. for 30 min, then allowed to warm to 23° C. The reaction mixture was diluted with water and extracted with EtOAc 3×. The combined organics were washed with brine, dried over magnesium sulfate and concentrated under vacuum to give 2-tert-butyl-3-hydroxy-5-methylisoindolin-1-one (10.6 g, 100% yield). MS (M+H)+ 220.

Example 426

Preparation of 6-methylphthalazin-1(2H)-one

To a solution of 2-tert-butyl-3-hydroxy-5-methylisoindolin-1-one (10.54 g, 48.1 mmol) in AcOH (250 ml) charged to a 500 mL round bottom and stirred at 80° C., hydrazine hydrate (3.51 ml, 72.1 mmol) was added. The reaction mixture was stirred at 80° C. for 90 min. The reaction mixture was then cooled and diluted with water and extracted with 4 L DCM. The organics were washed with brine, dried over magnesium sulfate and concentrated under vacuum to give 6-methylphthalazin-1(2H)-one. MS (M+H)+ 161.

Example 427

Preparation of 6-methyl-5-nitrophthalazin-1(2H)-one

To a solution of 6-methylphthalazin-1(2H)-one (12.100 g, 75.5 mmol) in sulfuric acid (100 ml) charged to a 500 mL round bottom heated to 80° C., potassium nitrate (11.5 g, 113 mmol) was added. The reaction mixture was stirred at 80° C. for 15 min and then cooled to room temperature. The reaction mixture was poured over ~000 mL of ice water, forming a white precipitate. This precipitate was filtered and to afford a solid (18 g). The resulting material contained the title compound, but contaminated with ~10% di-nitration product. This solid was stirred in 600 mL MeOH and filtered once again and 6-methyl-5-nitrophthalazin-1(2H)-one was collected as a white powder. MS (M+H)+ 206.

Example 428

Preparation of 5-amino-6-methylphthalazin-1(2H)-one

To a suspension of 6-methyl-5-nitrophthalazin-1(2H)-one (9.446 g, 46 mmol) in EtOH (1000 ml) charged to a 2000 mL round bottom flask, palladium, 10 wt. % on activated carbon (0.490 g, 0.46 mmol) was added. The reaction mixture was stirred at 50° C. for 6 days under $H_2$ (1 atm). When complete, the reaction mixture was filtered through a small pad of celite, washing with excess EtOH and some DMF. The liquid was then concentrated under vacuum to give 5-amino-6-methylphthalazin-1(2H)-one (7.99 g, 99% yield) as a yellow solid. MS (M+H)+ 176.

Example 429

Preparation of 5-iodo-6-methylphthalazin-1(2H)-one

To a solution of 5-amino-6-methylphthalazin-1(2H)-one (7.57 g, 43 mmol) in conc. aqueous HCl (250 ml) charged to a 500 mL round bottom, sodium nitrite (3.6 g, 52 mmol) in 50 mL water was added at 0° C. The mixture was then allowed to stir for 90 min at that temperature. Then, KI (22 g, 130 mmol) in water (50 ml) was added. The reaction mixture was stirred at 70° C. for 2 hrs, forming a dark precipitate on initial addition of iodide. Upon cooling to ambient temperature, the dark ppt was collected by filtration and stirred in a solution of saturated sodium sulfite, forming a light yellow precipitate. This precipitate was collected by filtration and washed with excess water. The light yellow solid was dried in a vacuum oven overnight to give 5-iodo-6-methylphthalazin-1(2H)-one (8.5 g, 69% yield. MS (M+H)+ 287.

Example 430

Preparation of 1-Chloro-5-iodo-6-methylphthalazine

A suspension of 5-iodo-6-methylphthalazin-1(2H)-one (8.51 g, 29.7 mmol) in phosphorous oxychloride (200 ml, 2146 mmol), charged to a 500 mL was stirred at 108° C. (reflux) for 90 min. The POCl₃ was then removed under vacuum, and the resulting residue was azeotroped 2× with toluene. The resulting residue was dissolved in a mixture of DCM and MeOH and water. The layers were separated the aqueous layer was washed with DCM 3×. The combined organics were washed with saturated aqueous sodium carbonate and brine. The organic layer was then dried over magnesium sulfate, and loaded on to silica. 1-Chloro-5-iodo-6-methylphthalazine (5.604 g, 61.9% yield) was obtained by column chromatography (ISCO 330 g 15%-60% EtOAc in Hex 60 min) as a yellow solid. MS (M+H)+ 305.

Example 431

Preparation of 1-(3-(5-iodo-6-methylphthalazin-1-ylamino)phenyl)ethanone

To a solution of 1-chloro-5-iodo-6-methylphthalazine (0.380 g, 1.25 mmol) in IPA (3.0 ml), charged to a 5 mL microwave reaction vessel, 3'-aminoacetophenone (0.253 g, 1.87 mmol) was added. The reaction mixture was stirred at 160° C. for 15 min. The reaction mixture was diluted with excess DCM and saturated aqueous sodium bicarbonate. The organic layer was washed with brine, dried over magnesium sulfate and concentrated under vacuum. The resulting residue was loaded on to silica and purified by column chromatography. (ISCO 40.0 g, 10-70% EtOAc in Hex., 25 min.) to give 1-(3-(5-iodo-6-methylphthalazin-1-ylamino)phenyl)ethanone (0.122 g, 24.2% yield). MS (M+H)+ 404.

Example 432

Preparation of 1-(3-(6-methyl-5-(2-(methylamino)quinazolin-6-yl)phthalazin-1-ylamino)phenyl)ethanone To a solution of 1-(3-(5-iodo-6-methylphthalazin-1-ylamino)phenyl)ethanone (0.122 g, 0.30 mmol) in 10:1 DMF:H2O (3.0 ml) charged to a 5-mL microwave reaction vessel, N-methyl-6-(4,4,5,5-tetramethyl-1,3,2-dioxaborolan-2-yl)quinazolin-2-amine (0.13 g, 0.45 mmol) and sodium carbonate hydrate (0.075 g, 0.61 mmol) were added. The reaction mixture was stirred for 5 min, sparging with N₂. Then, dichlorobis(triphenyl-phosphine)palladium (ii) (0.021 g, 0.030 mmol) was added. The reaction mixture was heated to 140° C. and stirred at that temperature for 15 min.

The reaction mixture was diluted with DCM and saturated aqueous sodium bicarbonate. The organic layer was washed with brine, dried over magnesium sulfate and concentrated under vacuum. The resulting residue was loaded on to silica and purified by column chromatography. (ISCO 40.0 g, 10-75% EtOAc in Hex., 25 min.) to give 1-(3-(6-methyl-5-(2-(methylamino)quinazolin-6-yl)phthalazin-1-ylamino)phenyl)ethanone (0.056 g, 43% yield). MS (M+H)+ 435.

Example 433

Preparation of 1-(3-(6-methyl-5-(2-(methylamino)quinazolin-6-yl)phthalazin-1-ylamino)phenyl)propan-2-ol To a solution of 2-(3-(6-methyl-5-(2-(methylamino)quinazolin-6-yl)phthalazin-1-ylamino)phenyl)ethanone (0.056 g, 0.13 mmol)n THF (2.0 ml), charged to a 50 mL round bottom, methylmagnesium bromide, 1.4 m solution in toluene/tetrahydrofuran (75:25) (0.19 ml, 0.27 mmol) was added at 0° C. The reaction mixture was stirred for 2 h. The reaction mixture was diluted with water and extracted with DCM. The combined organics were washed with brine, dried over magnesium sulfate and concentrated under vacuum. The resulting residue was loaded on to silica and purified by column Chromatography. (ISCO 12.0 g, 1-7% MeOH in DCM, 25 min.) to give 2-(3-(6-methyl-5-(2-(methylamino)quinazolin-6-yl)phthalazin-1-ylamino)phenyl)propan-2-ol. MS (M+H)+ 451.

Examples 434-438

The compounds of Examples 434-438 (see Table II) were prepared in a manner analogous to Examples 424-433, utilizing various substituted aryl-amino-methyl-amino phthalizine A-B rings with a fused C-D ring. These examples were synthesized using the general synthetic strategy described in scheme 21 (Method S).

The following compounds in Tables 3-8 are additional representative examples of Formulas I, II, IIa, III and IIIa, as provided by the present invention.

TABLE 3

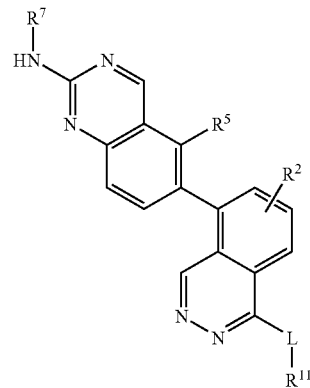

| Ex. No. | R² | R⁵ | R⁷ | L | R¹¹ |
|---|---|---|---|---|---|
| 439 | 6-CH₃— | H | H | —NH— | 3-CF₃-phenyl |
| 440 | 7-CH₃— | H | H | —NH— | 3-dimethylamino-phenyl |
| 441 | 8-CH₃— | H | H | —NH— | 3-CN-phenyl |
| 442 | 6-F— | H | —CH₃— | —C(O)NH— | 5-(3-t-butyl-1-methylpyrazole) |
| 443 | 7-Cl— | H | —CH₃— | —C(O)NH— | 6-(1-acetyl-6,6-dimethyl-2,3-dihydroindole |
| 444 | 8-Br— | H | —CH₃— | —C(O)NH— | 3-isopropoxy-phenyl |
| 445 | 6-CH₃— | H | H | —NH— | 1-(4-CF₃-1-pyridine) |

TABLE 3-continued

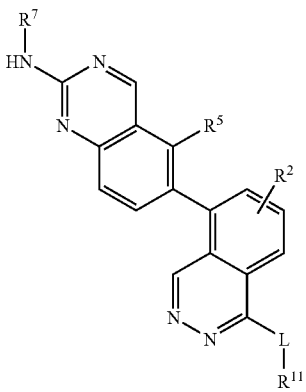

| Ex. No. | R² | R⁵ | R⁷ | L | R¹¹ |
|---|---|---|---|---|---|
| 446 | 7-CH₃— | H | H | —NH— | 5-(2-methyl-1,3-benzothiazole) |
| 447 | 8-CH₃— | H | H | —NH— | 5-(2,3-dihydroindene) |
| 448 | 6-F— | H | —CH₃— | —NH— | 3-trifluoromethoxy-phenyl |
| 449 | 7-Cl— | H | —CH₃— | —NH— | 2-(3-dimethylamino-propyl)-methylamino-5-CF₃-phenyl |

TABLE 3-continued

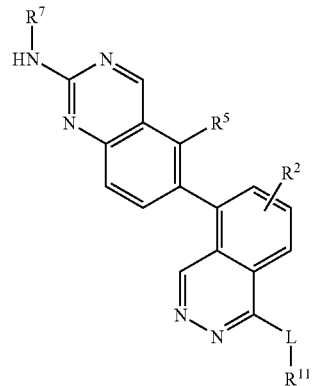

| Ex. No. | R² | R⁵ | R⁷ | L | R¹¹ |
|---|---|---|---|---|---|
| 450 | 8-Br— | H | —CH₃— | —NH— | 2-dimethylamino-5-CF₃-phenyl |
| 451 | 6-CH₃— | H | H | | 6-(1-acetyl-6,6-dimethyl-2,3-dihydroindole |
| 452 | 7-CH₃— | H | H | —NH— | 2-(3-dimethylamino-propyl)-methylamino-5-CF₃-phenyl |
| 453 | 8-CH₃— | H | H | —C(O)— | 3-isopropoxy-phenyl |

TABLE 4

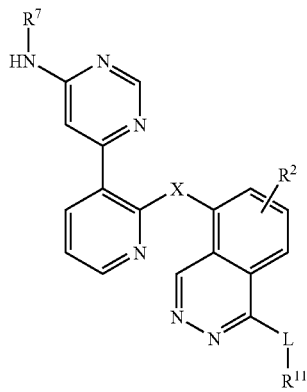

| Ex. No. | R² | X | R⁷ | L | R¹¹ |
|---|---|---|---|---|---|
| 454 | 6-CH₃— | —NH— | H | —NH— | 3-CF₃-phenyl |
| 455 | 7-CH₃— | —NH— | H | —NH— | 3-dimethylamino-phenyl |
| 456 | 8-CH₃— | —NH— | H | —NH— | 3-CN-phenyl |
| 457 | 6-F— | —O— | —CH₃— | —C(O)NH— | 5-(3-t-butyl-1-methylpyrazole) |
| 458 | 7-Cl— | —O— | —CH₃— | —C(O)NH— | 6-(1-acetyl-6,6-dimethyl-2,3-dihydroindole |
| 459 | 8-Br— | —O— | —CH₃— | —C(O)NH— | 3-isopropoxy-phenyl |
| 460 | 6-CH₃— | —NH— | H | —NH— | 1-(4-CF₃-1-pyridine) |
| 461 | 7-CH₃— | —NH— | H | —NH— | 5-(2-methyl-1,3-benzothiazole) |
| 462 | 8-CH₃— | —NH— | H | —NH— | 5-(2,3-dihydroindene) |
| 463 | 6-F— | —NH— | —CH₃— | —NH— | 3-trifluoromethoxy-phenyl |
| 464 | 7-Cl— | —NH— | —CH₃— | —NH— | 2-(3-dimethylaminopropyl)-methylamino-5-CF₃-phenyl |
| 465 | 8-Br— | —NH— | —CH₃— | —NH— | 2-dimethylamino-5-CF₃-phenyl |

TABLE 4-continued

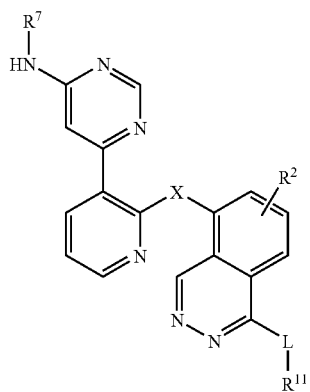

| Ex. No. | R² | X | R⁷ | L | R¹¹ |
|---|---|---|---|---|---|
| 466 | 6-CH₃— | —O— | H | —NH— | 6-(1-acetyl-6,6-dimethyl-2,3-dihydroindole |
| 467 | 7-CH₃— | —O— | H | —NH— | 2-(3-dimethylaminopropyl)-methylamino-5-CF₃-phenyl |
| 468 | 8-CH₃— | —O— | H | —C(O)— | 3-isopropoxy-phenyl |

TABLE 5

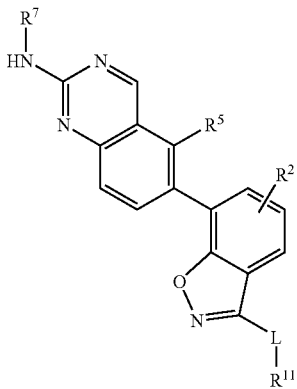

| Ex. No. | R² | R⁵ | R⁷ | L | R¹¹ |
|---|---|---|---|---|---|
| 469 | 6-CH₃— | H | H | —NH— | 3-CF₃-phenyl |
| 470 | 7-CH₃— | H | H | —NH— | 3-dimethylamino-phenyl |
| 471 | 8-CH₃— | H | H | —NH— | 3-CN-phenyl |
| 472 | 6-F— | H | —CH₃ | —C(O)NH— | 5-(3-t-butyl-1-methylpyrazole) |
| 473 | 7-Cl— | H | —CH₃ | —C(O)NH— | 6-(1-acetyl-6,6-dimethyl-2,3-dihydroindole |
| 474 | 8-Br— | H | —CH₃ | —C(O)NH— | 3-isopropoxy-phenyl |
| 475 | 6-CH₃— | H | H | —NH— | 1-(4-CF₃-1-pyridine) |
| 476 | 7-CH₃— | H | H | —NH— | 5-(2-methyl-1,3-benzothiazole) |
| 477 | 8-CH₃— | H | H | —NH— | 5-(2,3-dihydroindene) |
| 478 | 6-F— | H | —CH₃ | —NH— | 3-trifluoromethoxy-phenyl |

TABLE 5-continued

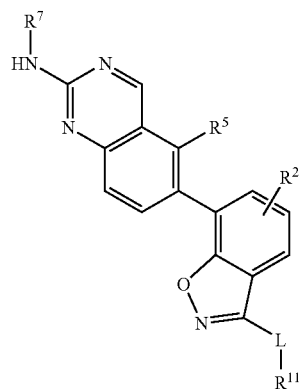

| Ex. No. | R² | R⁵ | R⁷ | L | R¹¹ |
|---|---|---|---|---|---|
| 479 | 7-Cl— | H | —CH₃ | —NH— | 2-(3-dimethylamino-propyl)methylamino-5-CF₃-phenyl |
| 480 | 8-Br— | H | —CH₃ | —NH— | 2-dimethylamino-5-CF₃-phenyl |
| 481 | 6-CH₃— | H | H | —NH— | 6-(1-acetyl-6,6-dimethyl-2,3-dihydroindole |
| 482 | 7-CH₃— | H | H | —NH— | 2-(3-dimethylamino-propyl)methylamino-5-CF₃-phenyl |
| 483 | 8-CH₃— | H | H | —C(O)— | 3-isopropoxy-phenyl |

TABLE 6

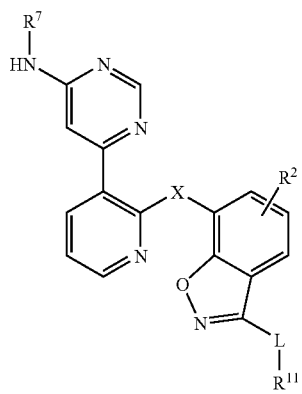

| Ex. No. | R² | X | R⁷ | L | R¹¹ |
|---|---|---|---|---|---|
| 484 | 6-CH₃— | —NH— | H | —NH— | 3-CF₃-phenyl |
| 485 | 7-CH₃— | —NH— | H | —NH— | 3-dimethylamino-phenyl |
| 486 | 8-CH₃— | —NH— | H | —NH— | 3-CN-phenyl |
| 487 | 6-F— | —O— | —CH₃ | —C(O)NH— | 5-(3-t-butyl-1-methylpyrazole) |
| 488 | 7-Cl— | —O— | —CH₃ | —C(O)NH— | 6-(1-acetyl-6,6-dimethyl-2,3-dihydroindole |
| 489 | 8-Br— | —O— | —CH₃ | —C(O)NH— | 3-isopropoxy-phenyl |
| 490 | 6-CH₃— | —NH— | H | —NH— | 1-(4-CF₃-1-pyridine) |
| 491 | 7-CH₃— | —NH— | H | —NH— | 5-(2-methyl-1,3-benzothiazole) |
| 492 | 8-CH₃— | —NH— | H | —NH— | 5-(2,3-dihydroindene) |
| 493 | 6-F— | —NH— | —CH₃ | —NH— | 3-trifluoromethoxy-phenyl |
| 494 | 7-Cl— | —NH— | —CH₃ | —NH— | 2-(3-dimethylaminopropyl-methylamino-5-CF₃-phenyl |
| 495 | 8-Br— | —NH— | —CH₃ | —NH— | 2-dimethylamino-5-CF₃-phenyl |
| 496 | 6-CH₃— | —O— | H | —NH— | 6-(1-acetyl-6,6-dimethyl-2,3-dihydroindole |
| 497 | 7-CH₃— | —O— | H | —NH— | 2-(3-dimethylaminopropyl)-methylamino-5-CF₃-phenyl |
| 498 | 8-CH₃— | —O— | H | —C(O)— | 3-isopropoxy-phenyl |

TABLE 7

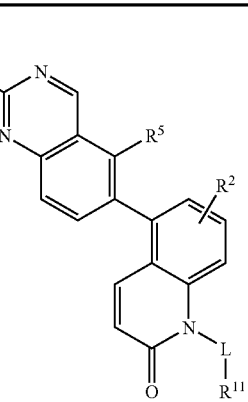

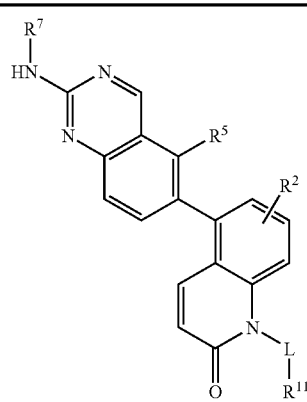

| Ex. No. | R² | R⁵ | R⁷ | L | R¹¹ |
|---|---|---|---|---|---|
| 499 | 6-CH₃— | H | H | —NH— | 3-CF₃-phenyl |
| 500 | 7-CH₃— | H | H | —NH— | 3-dimethylamino-phenyl |
| 501 | 8-CH₃— | H | H | —NH— | 3-CN-phenyl |
| 502 | 6-F— | H | —CH₃ | —C(O)NH— | 5-(3-t-butyl-1-methylpyrazole) |
| 503 | 7-Cl— | H | —CH₃ | —C(O)NH— | 6-(1-acetyl-6,6-dimethyl-2,3-dihydroindole |
| 504 | 8-Br— | H | —CH₃ | —C(O)NH— | 3-isopropoxy-phenyl |
| 505 | 6-CH₃— | H | H | —NH— | 1-(4-CF₃-1-pyridine) |

TABLE 7-continued

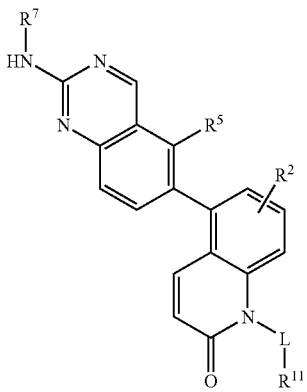

| Ex. No. | R² | R⁵ | R⁷ | L | R¹¹ |
|---|---|---|---|---|---|
| 506 | 7-CH₃— | H | H | —NH— | 5-(2-methyl-1,3-benzothiazole) |
| 507 | 8-CH₃— | H | H | —NH— | 5-(2,3-dihydroindene) |
| 508 | 6-F— | H | —CH₃— | —NH— | 3-trifluoromethoxy-phenyl |
| 509 | 7-Cl— | H | —CH₃— | —NH— | 2-(3-dimethylamino-propyl)-methylamino-5-CF₃-phenyl |
| 510 | 8-Br— | H | —CH₃— | —NH— | 2-dimethylamino-5-CF₃-phenyl |
| 511 | 6-CH₃— | H | H | | 6-(1-acetyl-6,6-dimethyl-2,3-dihydroindole |
| 512 | 7-CH₃— | H | H | —NH— | 2-(3-dimethylamino-propyl)-methylamino-5-CF₃-phenyl |
| 513 | 8-CH₃— | H | H | —C(O)— | 3-isopropoxy-phenyl |

TABLE 8

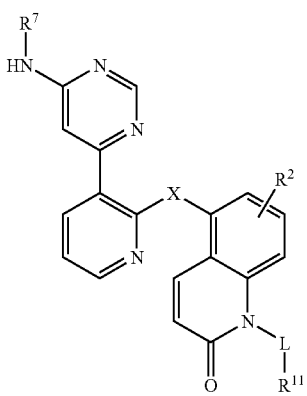

| Ex. No. | R² | R⁵ | R⁷ | L | R¹¹ |
|---|---|---|---|---|---|
| 514 | 6-CH₃— | H | H | —NH— | 3-CF₃-phenyl |
| 515 | 7-CH₃— | H | H | —NH— | 3-dimethylamino-phenyl |
| 516 | 6-F— | H | —CH₃— | —C(O)NH— | 5-(3-t-butyl-1-methylpyrazole) |
| 518 | 7-Cl— | H | —CH₃— | —C(O)NH— | 6-(1-acetyl-6,6-dimethyl-2,3-dihydroindole |

TABLE 8-continued

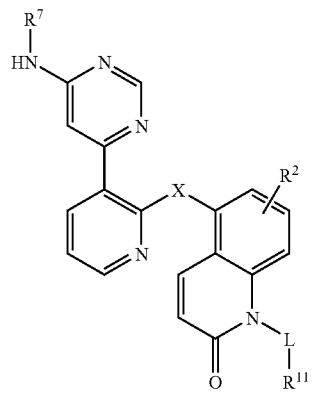

| Ex. No. | R² | R⁵ | R⁷ | L | R¹¹ |
|---|---|---|---|---|---|
| 519 | 8-Br— | H | —CH₃— | —C(O)NH— | 3-isopropoxy-phenyl |
| 520 | 6-CH₃— | H | H | —NH— | 1-(4-CF₃-1-pyridine) |
| 521 | 7-CH₃— | H | H | —NH— | 5-(2-methyl-1,3-benzothiazole) |
| 521 | 8-CH₃— | H | H | —NH— | 5-(2,3-dihydroindene) |
| 522 | 6-F— | H | —CH₃— | —NH— | 3-trifluoromethoxy-phenyl |
| 523 | 7-Cl— | H | —CH₃— | —NH— | 2-(3-dimethylamino-propyl)-methylamino-5-CF₃-phenyl |
| 524 | 8-Br— | H | —CH₃— | —NH— | 2-dimethylamino-5-CF₃-phenyl |
| 525 | 6-CH₃— | H | H | | 6-(1-acetyl-6,6-dimethyl-2,3-dihydroindole |
| 526 | 7-CH₃— | H | H | —NH— | 2-(3-dimethylamino-propyl)-methylamino-5-CF₃-phenyl |
| 527 | 8-CH₃— | H | H | —C(O)— | 3-isopropoxy-phenyl |

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be present in the end-products. The specialist knows, or can easily establish, which protecting groups are suitable with the reactions described herein.

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For example, the $R^2$ substituent is drawn unattached to any specific atom of ring Z', and therefore each of the n number of $R^2$ substituents may be attached to any atom of Z'.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I, II, IIa, III and IIIa) vary with structural change, in general, activity possessed by compounds of Formulas I, II, IIa, III and IIIa may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit kinase activity and, in particular, were found to inhibit raf kinase enzymes.

Biological Evaluation

The following assays can be employed to determine the degree of activity of a compound as a raf protein kinase inhibitor. Compounds described herein have been tested in one or more of these assays, and have shown activity. Representative compounds of the invention were tested and found to exhibit $IC_{50}$ values of at least <10 µM in any one of the described assays, thereby demonstrating and confirming the utility of the compounds of the invention as Raf kinase inhibitors and in the prophylaxis and treatment of Raf kinase mediated diseases, including, without limitation, cell-proliferative disorders and cancer.

B-raf-Homogenous Time Resolved Flourescent (HTRF) Kinase Assay

A Homogeneous Time Resolved Fluorescence (HTRF) kinase assay was established to assay the ability of compounds to inhibit human mutant Braf kinase activity on the substrate MEK1. The assay begins when 1 uL of a 50× compound dose curve in DMSO is added to 60 pM of recombinant HuBraf V600E in a final volume of 40 ul kinase reaction buffer. After a 60-minute incubation at room temperature, the kinase reaction is initiated with the addition of 10 ul substrate mix, resulting in a final concentration of 10 uM ATP (Km=~20 uM), 100 nM His-Avitag-MEK1 (Δ32-51,D190N kinase dead) (Km~200 nM) in a final reaction volume of 50 ul. The final concentration of the kinase reaction buffer is 50 mM Tris-HCL pH 7.5, 10 mM $MgCl_2$, 0.5% glucose, 0.5 mM DTT, 0.01% BSA.

The kinase reaction proceeds for 60 minutes at room temperature until the reaction is quenched by the addition of 10 ul Stop/Detection buffer composed of kinase reaction buffer with the addition of Tween-20 (for a final concentration 0.1%), Hexokinase (0.01 unit), Streptavidin-Allophycocyanin (final 10 nM), and Europium labeled anti-Phospho-MEK1/2 (ser217/221 from Cell Signaling Technology.) antibody (final 300 pM).

The detection reaction proceeds for one hour and is read on a RubyStar (BMG Labtech) counter. IC50s for the test compounds are generated using Excel-XLfit software.

The following exemplary compounds were found to have $IC_{50}$'s for the inhibition of B-raf as measured by the HTRF assay of less than or equal to 5 uM: Examples 7-19, 24-41, 50-58, 63-65, 68-73, 78-81, 86, 87-105, 107-185, 187-331, 337-344, 346, 349-354, 357-378, 381-383, 392-393, 395, 398, 399, 410-413, 415-424 and 433-438.

The following exemplary compounds were found to have $IC_{50}$'s for the inhibition of B-raf as measured by the HTRF assay of less than or equal to 1 uM: Examples 7-19, 24-41, 50-58, 63-65, 68, 70-73, 78-81, 87-105, 107-185, 187-196, 198, 201-207, 209-324, 326-331, 337-344, 346, 349-353, 357-358, 360-378, 381-383, 392-393, 395, 398, 399, 410, 412-413, 415-424, 433-434 and 437-438.

The following exemplary compounds were found to have $IC_{50}$'s for the inhibition of B-raf as measured by the HTRF assay of less than or equal to 500 nM: Examples 7-19, 24-41, 50-58, 63-65, 68, 70, 71, 73, 78-81, 87-105, 107-168, 170-181, 183-185, 187-196, 198, 201-207, 209-233, 235-324, 326-331, 337-344, 346, 349-353, 357-358, 360-363, 365-378, 381-383, 392-393, 395, 398, 399, 412-413, 415-420, 422-424, 433-434 and 437-438.

The following exemplary compounds were found to have $IC_{50}$'s for the inhibition of B-raf as measured by the HTRF assay of less than or equal to 250 nM: Examples 7-19, 24-41, 50-58, 63-65, 68, 71, 73, 78-81, 87-105, 107-168, 170-181, 183-185, 187-196, 198, 201-202, 204, 206-207, 209-212, 214-227, 229-233, 235-266, 268-313, 316-318, 320-324, 326-331, 337-344, 349-350, 352,357-358, 360, 361, 365-378, 381-383, 392-393, 395, 398, 399, 412-413, 415-420, 422-424, 433-434 and 437-438.

B-Raf Cell-Based Assay

A cell-based assay was optimized to assay the ability of compounds to inhibit Braf activity in a whole cell context.

A375 cells, a human melanoma cell line having the V600E mutant Braf is used in this assay. These cells exhibit constitutive Braf kinase activity which signals through phospho-MEK1/2 resulting in high levels of phospho-ERK1/2 (MAPK). The cell-based assay quantifies the ratio of phospho-ERK1/2 to total ERK1/2 and can thereby assay the cellular inhibition of Braf kinase activity.

A375 cells are plated into 96 well plates and grown to confluence. The cells are then changed into starve media (DMEM/0.1% BSA) for 60 minutes. Compounds in DMSO dose curves are then diluted in starve media and added to cells. DMSO with no compound is used in one column to determine a 'High' (no inhibition) reading, and 10 uM of a potent Braf inhibitor (a control compound) is used in another column to determine a 'Low' (complete inhibition) reading. After a 60 minute incubation the cells are fixed for 20 minutes at room temperature in 4% formaldehyde with 0.1% Triton X-100, protease and phosphatase inhibitors in PBS. The cells are washed four times in PBS then blocked for 60 minutes using a one to one mix of Odyssey blocking buffer (Li-Cor Biosciences, Inc) and PBS. Primary antibodies (rabbit anti-phospho p42/p44 MAPK (P-ERK1/2) from Cell Signaling Technology and mouse anti-ERK2 from Santa Cruz Biotechnology) are diluted in blocking buffer, added to the cells and incubated overnight at 4° C. The cells are then washed four times in PBS/0.1% Tween-20. Secondary antibodies (anti-mouse IRDye 800CW from Rockland, Inc and anti-rabbit AlexaFlour680 from Molecular Probes) are diluted in blocking buffer/0.5% Tween and incubated on cells for 60 minutes. After 4 washes in PBS/0.1% Tween-20 the microplate is scanned on an Odyssey Infrared Imager (Li-Cor Bioscience) which can read the signal given by the two secondary antibodies on their respective channels. The ratio of P-ERK/total ERK is determined and IC50s generated using Excel-XLfit software.

The following exemplary compounds were found to have $IC_{50}$'s for the inhibition of B-raf as measured by the above-described cell-based assay of less than or equal to 5 uM: Examples 7-19, 24-41, 50-56, 63-65, 68-73, 78-81, 86, 87-105, 107-161, 163-185, 187-331, 337-343, 346, 349, 352, 354, 357-378, 381-383, 392-393, 395, 398, 399, 410-413, 415-424 and 433-438.

The following exemplary compounds were found to have $IC_{50}$'s for the inhibition of B-raf as measured by the above-described cell-based assay of less than or equal to 1 uM: Examples 7-19, 24-41, 50-58, 63-65, 68, 70-73, 78-81, 87-99, 103, 107-113, 115-127, 129-140, 142-148, 150-161, 163, 165-166, 168-185, 187-193, 195-196, 198-204, 206-207, 209-216, 218-239, 241-250, 253-321, 323-331, 337-340, 343, 345, 347-348, 354-355, 357-358, 360-367, 369-378, 381-383, 392, 395, 398, 399, 410, 412-413, 416-424 and 438.

The following exemplary compounds were found to have $IC_{50}$'s for the inhibition of B-raf as measured by the above-described cell-based assay of less than or equal to 500 nM: Examples 7-19, 24-41, 50-58, 63-65, 68, 70-73, 78-81, 87-99, 103, 107-113, 115-127, 129-133, 135-140, 142-148, 150-161, 163, 165-166, 168-185, 187-189, 191-193, 196, 198-204, 206-207, 209-216, 218-239, 241-250, 253-271, 173-321, 323-331, 337-340, 343, 345, 347-348, 354-355, 357-358, 360-367, 369-378, 381-382, 392, 395, 398, 399, 410, 412-413, 416-424 and 438.

Indications

Accordingly, compounds of the invention are useful for, but not limited to, the prevention or treatment of Raf kinase-mediated diseases and disorders including, cancer and the RAS-RAF-MEK-ERK cell signaling pathway related diseases. In one embodiment of the invention, there is provided a method of modulating a Raf kinase enzyme in a subject, the method comprising administering to the subject an effective dosage amount of a compound of any of Formulas I, II, IIa, III and IIIa. In another embodiment, the raf kinase is a mutant version of the naturally occurring raf protein, such as the V600E mutant protein.

Raf-mediated disorders involve various cancers. In one embodiment, the invention provides a method of treating a raf-mediated condition selected from the group consisting of melanoma, solid tumor, ovarian cancer, pancreatic cancer, lung cancer, colon cancer and thyroid cancer. In another embodiment, the invention provides a method of treating a solid carcinoma of the lung, pancreas, thyroid, bladder or colon in a subject, the method comprising administering to the subject an effective dosage amount of a compound according to any of Formulas I, II, IIa, III and IIIa.

Treatment of Raf-mediated disease may be accomplished in combination with other oncological therapies. In one embodiment, the invention provides a method wherein administering the effective amount of the compound of Formula I, II, IIa, III and IIIa to the subject comprises administering the compound in combination with one or more compounds selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof.

Cancers which may be treated with compounds of the invention include, without limitation, carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Other therapeutic agents such as those described below may be employed with the inventive compounds in the present methods. In the methods of the present invention, such other therapeutic agent(s) may be administered prior to, simultaneously with or following the administration of the compound(s) of the present invention.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition or medicament comprising the compound, to a subject (i.e., an animal, preferably a mammal, most preferably a human) which may be in need of preventative treatment, such as, for example, for pain, inflammation, cancer and the like. Treatment also encompasses prophylactic administration of a compound of the invention, or a pharmaceutical salt thereof, or a pharmaceutical composition or medicament of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. In yet another embodiment, there I provided a method of manufacturing a medicament having therein a compound of Formulas I, II, IIa, III and IIIa, comprising combining the compound with a pharmaceutically acceptable carrier. The pharmaceutical composition, or medicament (used herein synonymously with composition) of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer such as with radiation therapy or with cytostatic or cytotoxic agents.

If formulated as a fixed dose, such combination products employ the compounds of this invention within the accepted dosage ranges. Compounds of Formulas I-IV may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or intravenous (IV) administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula II:

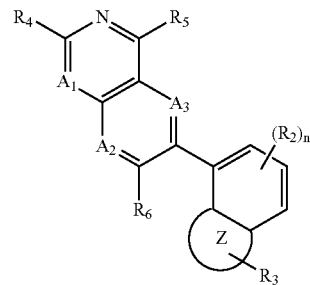

or a pharmaceutically acceptable salt thereof, wherein Z is

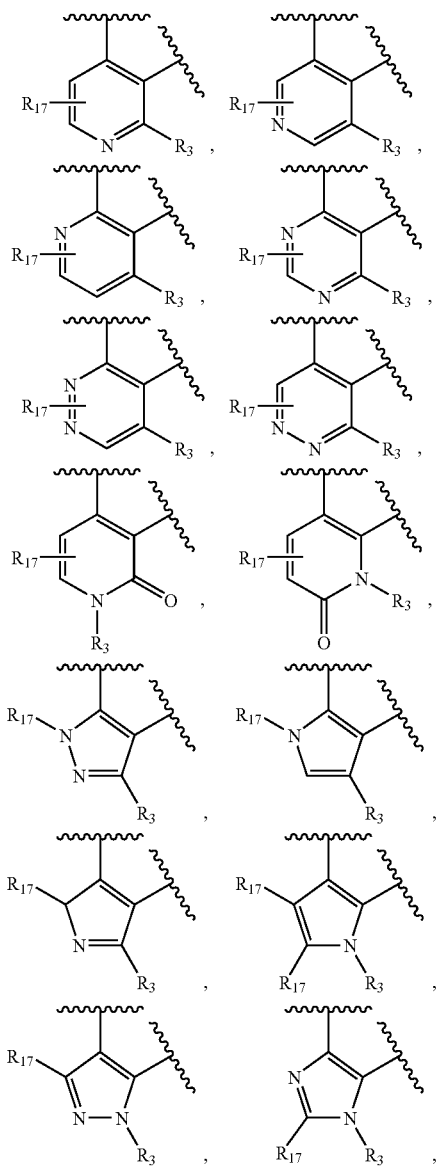

-continued

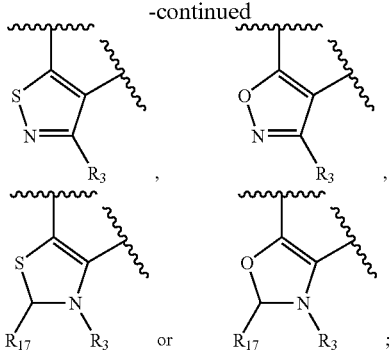

$A^1$ is N;

each of $A^2$ and $A^3$ is, independently, $CR^6$, wherein each $R^6$, independently, is H;

each $R^2$ is, independently, halo, haloalkyl, $NO_2$, CN, $NR^7R^7$, $NR^7R^8$, $OR^7$, $SR^7$, $C(O)R^7$ or $C_{1-4}$-alkyl, wherein the $C_{1-4}$-alkyl is optionally substituted with 1-3 substituents of Cl, Br, F, $CF_3$, CN, OH, $NO_2$ or $NH_2$;

$R^3$ is $NR^{10}R^{10}$, $NR^{10}R^{11}$, $SR^{10}$, $OR^{11}$, $SR^{11}$, $C(O)R^{10}$, $C(S)R^{10}$, $C(O)R^{11}$ or $C(S)R^{11}$;

$R^4$ is halo, haloalkyl, $NO_2$, CN, $R^7$, $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^5$ is H, F, Cl, CN, $OR^7$, $SR^7$, $NR^7R^7$, $NR^7R^8$, $C(O)R^7$ or $C_{1-4}$-alkyl;

$R^6$ is H;

each $R^7$ is, independently, H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$ or $R^9$;

$R^8$ is a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{10})$, $NR^{12}(COOR^{12})$, $OC(O)NR^{10}R^{12}$, $OC(O)NR^{12}R^{12}$, $S(O)_2R^{11}$, $S(O)^2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$,

S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{15}$ or R$^{16}$;

R$^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, each of which is optionally substituted independently with 1-5 substituents of R$^{16}$;

R$^{16}$ is halo, haloalkyl, CN, OH, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

R$^{17}$ is H, halo, haloalkyl, CN, OH, NO$_2$, NH$_2$, acetyl, methyl, methoxyl, ethyl, ethoxyl, propyl, propoxyl, isopropyl, cyclopropyl, butyl, isobutyl, sec-butyl, tert-butyl, methylamine, dimethylamine, ethylamine, diethylamine, propylamine, isopropylamine, dipropylamine, diisopropylamine, butylamine, benzyl or phenyl; and n is an integer selected from 0, 1, 2 and 3.

2. The compound of claim 1, or a pharmaceutically acceptable salt thereof, wherein R$^4$ is H, halo, haloalkyl, NO$_2$, CN, C$_{1-10}$-alkyl, NR$^7$R$^7$, NR$^7$R$^8$, OR$^7$, SR$^7$, OR$^8$, SR$^8$, C(O)R$^7$ or C(O)R$^8$; and R$^5$ is H, F, CN, —OCH$_3$, —SCH$_3$, —NHCH$_3$, —OCF$_3$ or C(O)CH$_3$.

3. The compound of claim 1 wherein Z is

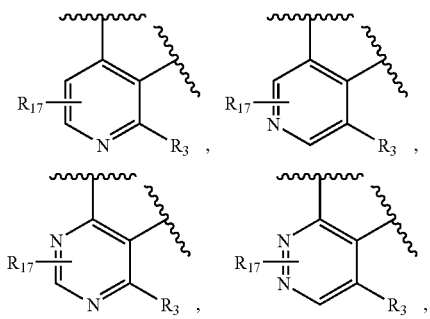

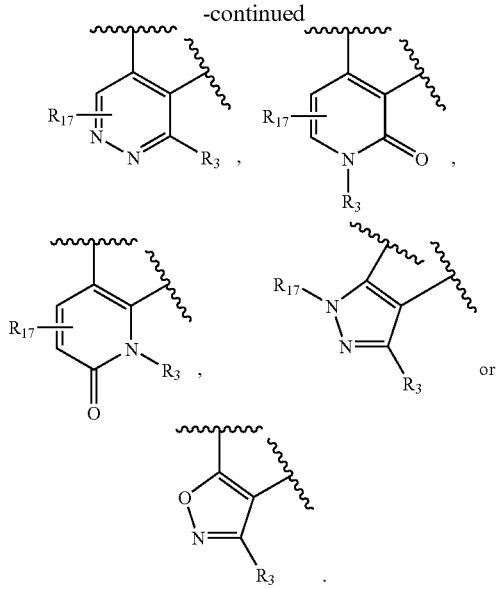

4. The compound of claim 3, or a pharmaceutically acceptable salt thereof, wherein each R$^2$ is, independently, F, CF$_3$, NO$_2$, CH$_3$, CN, —OCH$_3$, —SCH$_3$, —NHCH$_3$, —OCF$_3$ or C(O)CH$_3$.

5. The compound of claim 4, or a pharmaceutically acceptable salt thereof, wherein R$^3$ is NR$^{10}$R$^{11}$;

R$^{10}$ is H or C$_{1-6}$-alkyl; and

R$^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of R$^{12}$, R$^{13}$, R$^{14}$ or R$^{16}$.

6. The compound of claim 5, or a pharmaceutically acceptable salt thereof, having a Formula IIa:

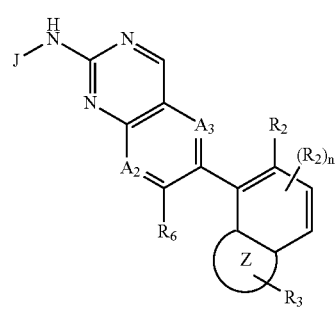

IIa wherein J is H, acetyl, C$_{1-10}$-alkyl, C$_{2-10}$-alkenyl, C$_{2-10}$-alkynyl, C$_{3-10}$-cycloalkyl, C$_{4-10}$-cycloalkenyl or a saturated or partially or fully unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl, and n is 0 or 1.

7. The compound of claim 6, or a pharmaceutically acceptable salt thereof, wherein J is H or $C_{1-10}$-alkyl optionally substituted with 1-3 substituents of $R^9$;

Z is $R^3$ is $NR^{10}R^{11}$;

each $R^9$ is, independently, halo, haloalkyl, CN, OH, $NO_2$, $NH_2$, acetyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H or $CH_3$; and $R^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, iso-quinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of $R^{12}$, $R^{13}$, $R^{14}$ or $R^{16}$.

8. A compound, or a pharmaceutically acceptable salt thereof, selected from:

N-methyl-6-(6-methyl-1((3-(trifluoromethyl)phenyl)amino)-5-isoquinolinyl)-2-quinazolinamine;

N-methyl-6-(6-methyl-1-((3-((1-methylethyl)oxy)phenyl)amino)-5-isoquinolinyl)-2-quinazolinamine;

N-methyl-6-(6-methyl-1-((3-(1-methylethyl)phenyl)amino)-5-isoquinolinyl)-2-quinazolinamine;

6-(1-((5-(1,1-dimethylethyl)-3-isoxazolyl)amino)-6-methyl-5-isoquinolinyl)-N-methyl-2-quinazolinamine;

6-(1-((3-(1,1-dimethylethyl)phenyl)amino)-6-methyl-5-isoquinolinyl)-N-methyl-2-quinazolinamine;

6-(1-((3-chlorophenyl)amino)-6-methyl-5-isoquinolinyl)-N-methyl-2-quinazolinamine;

3-((6-methyl-5-(2-(methylamino)-6-quinazolinyl)-1-isoquinolinyl)amino)benzonitrile;

6-(1-((3-(1,1-dimethylethyl)-1-methyl-1H-pyrazol-5-yl)amino)-6-methyl-5-isoquinolinyl)-N-methyl-2-quinazolinamine;

N-methyl-6-(6-methyl-1-((3-((trifluoromethyl)oxy)phenyl)amino)-5-isoquinolinyl)-2-quinazolinamine;

6-(1-((1-acetyl-3,3-dimethyl-2,3-dihydro-1H-indol-6-yl)amino)-6-methyl-5-isoquinolinyl)-N-methyl-2-quinazolinamine;

N-methyl-6-(6-methyl-1-((4-(trifluoromethyl)-2-pyridinyl)amino)-5-isoquinolinyl)-2-quinazolinamine;

N-methyl-6-(6-methyl-1-((4-(methyloxy)-3-(trifluoromethyl)phenyl)amino)-5-isoquinolinyl)-2-quinazolinamine;

6-(1-((5-cyclopropyl-1,3,4-thiadiazol-2-yl)amino)-6-methyl-5-isoquinolinyl)-N-methyl-2-quinazolinamine;

6-(1-(1H-indazol-5-ylamino)-6-methyl-5-isoquinolinyl)-N-methyl-2-quinazolinamine;

6-(1-(2,3-dihydro-1H-inden-5-ylamino)-6-methyl-5-isoquinolinyl)-N-methyl-2-quinazolinamine;

N-methyl-6-(6-methyl-1-((2-methyl-1,3-benzothiazol-5-yl)amino)-5-isoquinolinyl)-2-quinazolinamine;

6-(1-((4-fluoro-3-((1-methylethyl)oxy)phenyl)amino)-6-methyl-5-isoquinolinyl)-N-methyl-2-quinazolinamine;

N-methyl-6-(6-methyl-1-((5-(trifluoromethyl)-3-pyridinyl)amino)-5-isoquinolinyl)-2-quinazolinamine;

6-(4-(2,3-dihydro-1H-inden-5-ylamino)-7-methylquinazolin-8-yl)-N-methylquinazolin-2-amine;

$N^2,7'$-dimethyl-$N^{4'}$-(3-((trifluoromethyl)oxy)phenyl)-6,8'-biquinazoline-2,4'-diamine;

$N^2,7'$-dimethyl-$N^{4'}$-(3-(trifluoromethyl)phenyl)-6,8'-biquinazoline-2,4'-diamine;

$N^2,7'$-dimethyl-$N^{4'}$-(4-(methyloxy)-3-(trifluoromethyl)phenyl)-6,8'-biquinazoline-2,4'-diamine;

$N^{4'}$-(3-(1,1-dimethylethyl)-1-methyl-1H-pyrazol-5-yl)-$N^2,7'$-dimethyl-6,8'-biquinazoline-2,4'-diamine;

$N^{4'}$-(1-acetyl-3,3-dimethyl-2,3-dihydro-1H-indol-6-yl)-$N^2,7'$-dimethyl-6,8'-biquinazoline-2,4'-diamine;

N⁴'-(4-chloro-3-(trifluoromethyl)phenyl)-N²,7'-dimethyl-6,8'-biquinazoline-2,4'-diamine;
N²,7'-dimethyl-N⁴'-(5-(trifluoromethyl)-3-pyridinyl)-6,8'-biquinazoline-2,4'-diamine;
N⁴'-(4-(1,1-dimethylethyl)cyclohexyl)-N²,7'-dimethyl-6,8'-biquinazoline-2,4'-diamine;
N²,7'-dimethyl-N⁴'-(2-methyl-1,3-benzothiazol-5-yl)-6,8'-biquinazoline-2,4'-diamine;
6-(1,6-dimethyl-3-((3-(trifluoromethyl)phenyl)amino)-1H-indazol-7-yl)-N-methyl-2-quinazolinamine;
6-(1,6-dimethyl-3-((4-(methyloxy)-3-(trifluoromethyl)phenyl)amino)-1H-indazol-7-yl)-N-methyl-2-quinazolinamine;
6-(1,6-dimethyl-3-((3-((trifluoromethyl)oxy)phenyl)amino)-1H-indazol-7-yl)-N-methyl-2-quinazolinamine;
N-methyl-6-(6-methyl-3-((3-((1-methylethyl)oxy)phenyl)amino)-1H-indazol-7-yl)-2-quinazolinamine;
6-(1-((3,3-dimethyl-2,3-dihydro-1H-indol-6-yl)amino)-6-methyl-5-isoquinolinyl)-N-methyl-2-quinazolinamine; and
6-(2,7-dimethyl-4-(3-(trifluoromethoxy)phenylamino)quinazolin-8-yl)-N-methylquinazolin-2-amine.

9. A pharmaceutical composition comprising a pharmaceutically acceptable carrier and a compound according to claim 1.

10. A pharmaceutical composition comprising a pharmaceutically acceptable carrier and a compound according to claim 7.

11. A pharmaceutical composition comprising a pharmaceutically acceptable carrier and a compound according to claim 8.

12. A compound having a Formula IIa:

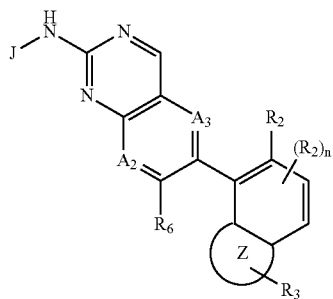

or a pharmaceutically acceptable salt thereof, wherein
each of $A^2$ and $A^3$ is, independently, $CR^6$, wherein each $R^6$, independently, is H;
J is H, haloalkyl, CN, —C(O)CH₃, $C_{1-10}$-alkyl, $C_{2-10}$-alkenyl, $C_{2-10}$-alkynyl, $C_{3-10}$-cycloalkyl, $C_{4-10}$-cycloalkenyl or a saturated or partially or fully unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl and ring of said ring system is optionally substituted independently with 1-5 substituents of halo, haloalkyl, CN, NO₂, NH₂, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;
each $R^2$ is, independently, halo, haloalkyl, NO₂, CN, —NCH₃, —OCH₃, —SCH₃, —C(O)CH₃, or $C_{1-4}$-alkyl, wherein the $C_{1-4}$-alkyl is optionally substituted with 1-3 substituents of Cl, Br, F, CF₃, CN, OH, NO₂ or NH₂;
$R^3$ is $NR^{10}R^{10}$ or $NR^{10}R^{11}$;
$R^6$ is H;
$R^{10}$ is H or CH₃;
$R^{11}$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, cyclopropyl, cyclobutyl, azetidinyl, cyclopentyl and cyclohexyl, each of which is optionally substituted independently with 1-5 substituents of $R^{12}$, $R^{13}$, $R^{14}$ or $R^{16}$;
alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;
$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;
$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$; $S(O)_2R^{14}$; $S(O)_2R^{15}S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;
$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;
$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;
$R^{16}$ halo, haloalkyl, CN, OH, NO₂, NH₂, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

Z is

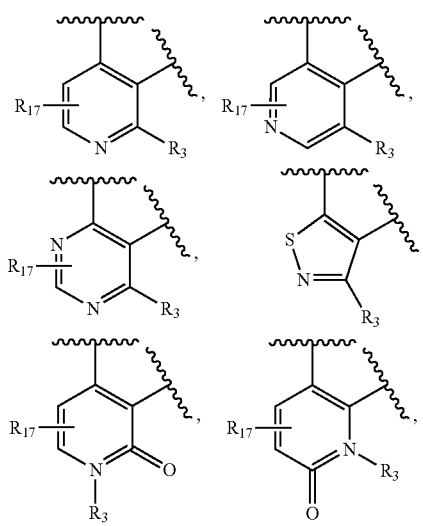

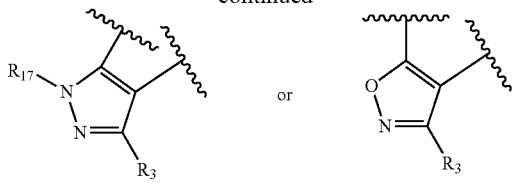

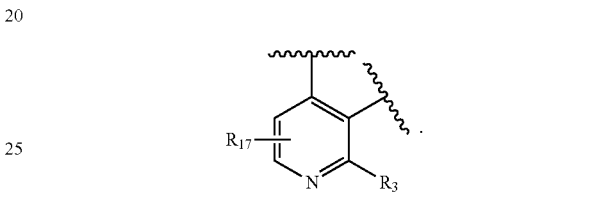

wherein $R^{17}$ is H, halo, haloalkyl, CN, OH, $NO_2$, $NH_2$, acetyl, methyl, methoxyl, ethyl, ethoxyl, propyl, propoxyl, isopropyl, cyclopropyl, butyl, isobutyl, sec-butyl, tert-butyl, methylamine, dimethylamine, ethylamine, diethylamine, propylamine, isopropylamine, dipropylamine, diisopropylamine, butylamine, benzyl or phenyl; and n is an integer selected from 0, 1 or 2.

13. The compound of claim 12, or a pharmaceutically acceptable salt thereof, wherein J is H or $C_{1-10}$-alkyl, and Z is 14. A pharmaceutical composition comprising a pharmaceutically acceptable carrier and a compound according to claim 12.

* * * * *